(12) United States Patent
Robertson et al.

(10) Patent No.: US 8,951,272 B2
(45) Date of Patent: Feb. 10, 2015

(54) SEAL ARRANGEMENTS FOR ULTRASONICALLY POWERED SURGICAL INSTRUMENTS

(75) Inventors: Galen C. Robertson, Cincinnati, OH (US); Kevin L. Houser, Springboro, OH (US); Mark A. Neurohr, Newport, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 592 days.

(21) Appl. No.: 12/703,866

(22) Filed: Feb. 11, 2010

(65) Prior Publication Data
US 2011/0196398 A1     Aug. 11, 2011

(51) Int. Cl.
*A61B 17/32*     (2006.01)

(52) U.S. Cl.
CPC ... *A61B 17/320068* (2013.01); *A61B 17/32002* (2013.01); *A61B 2017/320088* (2013.01)
USPC ...................................... 606/169

(58) Field of Classification Search
USPC ......... 606/159, 160, 170, 171, 175, 176, 178, 606/179, 180; 604/22, 24, 23; 277/644, 277/626, 647, 567
See application file for complete search history.

(56) References Cited

U.S. PATENT DOCUMENTS

| | | | |
|---|---|---|---|
| 969,528 A | 9/1910 | Disbrow | |
| 1,570,025 A | 1/1926 | Young | |
| 2,704,333 A | 3/1955 | Calosi et al. | |
| 2,736,960 A | 3/1956 | Armstrong | |
| 2,849,788 A | 9/1958 | Creek | |
| RE25,033 E | 8/1961 | Balamuth et al. | |
| 3,015,961 A | 1/1962 | Roney | |
| 3,082,805 A | 3/1963 | Royce | |
| 3,513,848 A | 5/1970 | Winston et al. | |
| 3,526,219 A | 9/1970 | Balamuth | |
| 3,614,484 A | 10/1971 | Shoh | |
| 3,636,943 A | 1/1972 | Balamuth | |
| 3,776,238 A | 12/1973 | Peyman et al. | |
| 3,805,787 A | 4/1974 | Banko | |
| 3,830,098 A | 8/1974 | Antonevich | |
| 3,854,737 A * | 12/1974 | Gilliam, Sr. | 277/566 |
| 3,862,630 A | 1/1975 | Balamuth | |
| 3,900,823 A | 8/1975 | Sokal et al. | |
| 3,918,442 A | 11/1975 | Nikolaev et al. | |
| 3,946,738 A | 3/1976 | Newton et al. | |
| 3,955,859 A | 5/1976 | Stella et al. | |

(Continued)

FOREIGN PATENT DOCUMENTS

| CN | 1634601 A | 7/2005 |
|---|---|---|
| CN | 1640365 A | 7/2005 |

(Continued)

OTHER PUBLICATIONS

International Search Report for PCT/US2011/024190, Sep. 12, 2011 (7 pages).

(Continued)

*Primary Examiner* — Tuan V Nguyen

(57) ABSTRACT

In one general aspect, various embodiments are directed to ultrasonic surgical instruments that may be used in aqueous environments. The instruments may include cutting a member that is supported within a hollow sheath. Various seal arrangements are disclosed for establishing a substantially fluid-tight seal between the cutting member and the sheath.

8 Claims, 44 Drawing Sheets

(56) References Cited

U.S. PATENT DOCUMENTS

| | | |
|---|---|---|
| 3,956,826 A | 5/1976 | Perdreaux, Jr. |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,444 A | 5/1980 | Bonnell et al. |
| 4,306,570 A | 12/1981 | Matthews |
| 4,445,063 A | 4/1984 | Smith |
| 4,491,132 A | 1/1985 | Aikins |
| 4,494,759 A | 1/1985 | Kieffer |
| 4,504,264 A | 3/1985 | Kelman |
| 4,512,344 A | 4/1985 | Barber |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,646,738 A | 3/1987 | Trott |
| 4,649,919 A | 3/1987 | Thimsen et al. |
| 4,674,502 A | 6/1987 | Imonti |
| 4,708,127 A | 11/1987 | Abdelghani |
| 4,712,722 A | 12/1987 | Hood et al. |
| 4,819,635 A | 4/1989 | Shapiro |
| 4,827,911 A | 5/1989 | Broadwin et al. |
| 4,832,683 A | 5/1989 | Idemoto et al. |
| 4,838,853 A | 6/1989 | Parisi |
| 4,844,064 A | 7/1989 | Thimsen et al. |
| 4,850,354 A | 7/1989 | McGurk-Burleson et al. |
| 4,865,159 A | 9/1989 | Jamison |
| 4,867,157 A | 9/1989 | McGurk-Burleson et al. |
| 4,881,550 A | 11/1989 | Kothe |
| 4,896,009 A | 1/1990 | Pawlowski |
| 4,903,696 A | 2/1990 | Stasz et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,026,387 A | 6/1991 | Thomas |
| 5,084,052 A | 1/1992 | Jacobs |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| 5,162,044 A | 11/1992 | Gahn et al. |
| 5,163,537 A * | 11/1992 | Radev .................... 180/65.1 |
| 5,167,725 A | 12/1992 | Clark et al. |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grezeszykowski |
| 5,188,102 A | 2/1993 | Idemoto et al. |
| 5,213,569 A | 5/1993 | Davis |
| 5,221,282 A | 6/1993 | Wuchinich |
| 5,226,909 A | 7/1993 | Evans et al. |
| 5,226,910 A | 7/1993 | Kajiyama et al. |
| 5,241,236 A | 8/1993 | Sasaki et al. |
| 5,242,460 A | 9/1993 | Klein et al. |
| 5,257,988 A | 11/1993 | L'Esperance, Jr. |
| 5,261,922 A | 11/1993 | Hood |
| 5,263,957 A | 11/1993 | Davison |
| 5,275,609 A | 1/1994 | Pingleton et al. |
| 5,282,800 A | 2/1994 | Foshee et al. |
| 5,285,795 A | 2/1994 | Ryan et al. |
| 5,304,115 A | 4/1994 | Pflueger et al. |
| D347,474 S | 5/1994 | Olson |
| 5,312,425 A | 5/1994 | Evans et al. |
| 5,322,055 A | 6/1994 | Davison et al. |
| 5,324,299 A | 6/1994 | Davison et al. |
| 5,326,342 A | 7/1994 | Pflueger et al. |
| 5,344,420 A | 9/1994 | Hilal et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,366,466 A | 11/1994 | Christian et al. |
| 5,371,429 A | 12/1994 | Manna |
| D354,564 S | 1/1995 | Medema |
| 5,381,067 A | 1/1995 | Greenstein et al. |
| 5,387,215 A | 2/1995 | Fisher |
| 5,403,312 A | 4/1995 | Yates et al. |
| 5,403,334 A | 4/1995 | Evans et al. |
| 5,411,481 A | 5/1995 | Allen et al. |
| 5,419,761 A | 5/1995 | Narayanan et al. |
| 5,421,829 A | 6/1995 | Olichney et al. |
| 5,423,844 A | 6/1995 | Miller |
| 5,438,997 A | 8/1995 | Sieben et al. |
| 5,445,639 A | 8/1995 | Kuslich et al. |
| 5,449,370 A | 9/1995 | Vaitekunas |
| 5,471,988 A | 12/1995 | Fujio et al. |
| 5,483,501 A | 1/1996 | Park et al. |
| 5,486,162 A | 1/1996 | Brumbach |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,540,693 A | 7/1996 | Fisher |
| 5,562,609 A | 10/1996 | Brumbach |
| 5,562,610 A | 10/1996 | Brumbach |
| 5,577,654 A | 11/1996 | Bishop |
| 5,591,187 A | 1/1997 | Dekel |
| 5,601,601 A | 2/1997 | Tal et al. |
| 5,603,773 A | 2/1997 | Campbell |
| 5,607,436 A | 3/1997 | Pratt et al. |
| 5,618,492 A | 4/1997 | Auten et al. |
| 5,620,447 A | 4/1997 | Smith et al. |
| 5,628,760 A | 5/1997 | Knoepfler |
| 5,630,420 A | 5/1997 | Vaitekunas |
| D381,077 S | 7/1997 | Hunt |
| 5,651,780 A | 7/1997 | Jackson et al. |
| 5,653,713 A | 8/1997 | Michelson |
| 5,669,922 A | 9/1997 | Hood |
| 5,674,235 A | 10/1997 | Parisi |
| 5,690,269 A | 11/1997 | Bolanos et al. |
| 5,694,936 A | 12/1997 | Fujimoto et al. |
| 5,713,896 A | 2/1998 | Nardella |
| 5,730,752 A | 3/1998 | Alden et al. |
| 5,733,074 A | 3/1998 | Stöck et al. |
| 5,741,226 A | 4/1998 | Strukel et al. |
| 5,792,135 A | 8/1998 | Madhani et al. |
| 5,792,165 A | 8/1998 | Klieman et al. |
| 5,808,396 A | 9/1998 | Boukhny |
| 5,810,859 A | 9/1998 | DiMatteo et al. |
| 5,817,084 A | 10/1998 | Jensen |
| 5,817,119 A | 10/1998 | Klieman et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,957 A | 11/1998 | Schulz et al. |
| 5,843,109 A | 12/1998 | Mehta et al. |
| 5,851,212 A | 12/1998 | Zirps et al. |
| 5,873,882 A | 2/1999 | Straub et al. |
| 5,878,193 A | 3/1999 | Wang et al. |
| 5,879,364 A | 3/1999 | Bromfield et al. |
| 5,883,615 A | 3/1999 | Fago et al. |
| 5,893,835 A | 4/1999 | Witt et al. |
| 5,897,523 A | 4/1999 | Wright et al. |
| 5,897,569 A | 4/1999 | Kellogg et al. |
| 5,904,681 A | 5/1999 | West, Jr. |
| 5,906,627 A | 5/1999 | Spaulding |
| 5,906,628 A | 5/1999 | Miyawaki et al. |
| 5,911,699 A | 6/1999 | Anis et al. |
| 5,916,229 A | 6/1999 | Evans |
| 5,935,143 A | 8/1999 | Hood |
| 5,935,144 A * | 8/1999 | Estabrook .................... 606/169 |
| 5,938,633 A | 8/1999 | Beaupre |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |

(56) References Cited

U.S. PATENT DOCUMENTS

| | | |
|---|---|---|
| 5,968,060 A | 10/1999 | Kellogg |
| D416,089 S | 11/1999 | Barton et al. |
| 5,980,510 A | 11/1999 | Tsonton et al. |
| 5,980,546 A | 11/1999 | Hood |
| 5,989,274 A | 11/1999 | Davison et al. |
| 5,989,275 A | 11/1999 | Estabrook et al. |
| 5,993,972 A | 11/1999 | Reich et al. |
| 6,024,741 A | 2/2000 | Williamson, IV et al. |
| 6,027,515 A | 2/2000 | Cimino |
| 6,033,375 A | 3/2000 | Brumbach |
| 6,036,707 A | 3/2000 | Spaulding |
| 6,050,943 A | 4/2000 | Slayton et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,099,542 A | 8/2000 | Cohn et al. |
| 6,109,500 A | 8/2000 | Alli et al. |
| 6,110,127 A * | 8/2000 | Suzuki .......................... 600/565 |
| 6,113,594 A | 9/2000 | Savage |
| 6,117,152 A | 9/2000 | Huitema |
| 6,126,629 A | 10/2000 | Perkins |
| 6,129,735 A | 10/2000 | Okada et al. |
| 6,132,368 A | 10/2000 | Cooper |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,147,560 A | 11/2000 | Erhage et al. |
| 6,152,902 A | 11/2000 | Christian et al. |
| 6,159,160 A | 12/2000 | Hsei et al. |
| 6,159,175 A | 12/2000 | Strukel et al. |
| 6,165,150 A | 12/2000 | Banko |
| 6,179,853 B1 | 1/2001 | Sachse et al. |
| 6,204,592 B1 | 3/2001 | Hur |
| 6,206,844 B1 | 3/2001 | Reichel et al. |
| 6,210,403 B1 | 4/2001 | Klicek |
| 6,214,023 B1 | 4/2001 | Whipple et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,252,110 B1 | 6/2001 | Uemura et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,340,352 B1 | 1/2002 | Okada et al. |
| 6,352,532 B1 | 3/2002 | Kramer et al. |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,387,109 B1 | 5/2002 | Davison et al. |
| 6,388,657 B1 | 5/2002 | Natoli |
| 6,391,042 B1 | 5/2002 | Cimino |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,511,493 B1 | 1/2003 | Moutafis et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,561,983 B2 | 5/2003 | Cronin et al. |
| 6,572,563 B2 | 6/2003 | Ouchi |
| 6,572,632 B2 | 6/2003 | Zisterer et al. |
| 6,575,969 B1 | 6/2003 | Rittman, III et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,610,059 B1 | 8/2003 | West, Jr. |
| 6,616,450 B2 | 9/2003 | Mossle et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,633,234 B2 | 10/2003 | Wiener et al. |
| 6,656,132 B1 | 12/2003 | Ouchi |
| 6,656,177 B2 | 12/2003 | Truckai et al. |
| 6,662,127 B2 | 12/2003 | Wiener et al. |
| 6,663,941 B2 | 12/2003 | Brown et al. |
| 6,669,690 B1 | 12/2003 | Okada et al. |
| 6,669,710 B2 | 12/2003 | Moutafis et al. |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,899 B2 | 1/2004 | Wiener et al. |
| 6,682,544 B2 | 1/2004 | Mastri et al. |
| 6,689,145 B2 | 2/2004 | Lee et al. |
| 6,689,146 B1 | 2/2004 | Himes |
| 6,716,215 B1 | 4/2004 | David et al. |
| 6,731,047 B2 | 5/2004 | Kauf et al. |
| 6,733,506 B1 | 5/2004 | McDevitt et al. |
| 6,743,245 B2 | 6/2004 | Lobdell |
| 6,762,535 B2 | 7/2004 | Take et al. |
| 6,770,072 B1 | 8/2004 | Truckai et al. |
| 6,773,443 B2 | 8/2004 | Truwit et al. |
| 6,773,444 B2 | 8/2004 | Messerly |
| 6,783,524 B2 | 8/2004 | Anderson et al. |
| 6,786,382 B1 | 9/2004 | Hoffman |
| 6,786,383 B2 | 9/2004 | Stegelmann |
| 6,790,216 B1 | 9/2004 | Ishikawa |
| 6,802,843 B2 | 10/2004 | Truckai et al. |
| 6,827,712 B2 | 12/2004 | Tovey et al. |
| 6,828,712 B2 | 12/2004 | Battaglin et al. |
| 6,863,676 B2 | 3/2005 | Lee et al. |
| 6,869,439 B2 | 3/2005 | White et al. |
| 6,875,220 B2 | 4/2005 | Du et al. |
| 6,887,209 B2 | 5/2005 | Kadziauskas et al. |
| 6,899,685 B2 | 5/2005 | Kermode et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,923,804 B2 | 8/2005 | Eggers et al. |
| 6,926,716 B2 | 8/2005 | Baker et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,677 B2 | 9/2005 | Nita et al. |

(56) References Cited

U.S. PATENT DOCUMENTS

| | | |
|---|---|---|
| 6,945,981 B2 | 9/2005 | Donofrio et al. |
| D511,145 S | 11/2005 | Donofrio et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,984,220 B2 | 1/2006 | Wuchinich |
| 7,001,335 B2 | 2/2006 | Adachi et al. |
| 7,011,657 B2 | 3/2006 | Truckai et al. |
| 7,033,357 B2 | 4/2006 | Baxter et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,066,893 B2 | 6/2006 | Hibner et al. |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,371 B2 | 9/2006 | Dycus et al. |
| 7,101,378 B2 | 9/2006 | Salameh et al. |
| 7,108,695 B2 | 9/2006 | Witt et al. |
| 7,112,201 B2 | 9/2006 | Truckai et al. |
| D531,311 S | 10/2006 | Guerra et al. |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,135,018 B2 | 11/2006 | Ryan et al. |
| 7,135,030 B2 | 11/2006 | Schwemberger et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,299 B2 | 1/2007 | Baily |
| 7,163,548 B2 | 1/2007 | Stulen et al. |
| 7,169,146 B2 | 1/2007 | Truckai et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,204,820 B2 | 4/2007 | Akahoshi |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,273,483 B2 | 9/2007 | Wiener et al. |
| 7,285,895 B2 | 10/2007 | Beaupré |
| 7,303,531 B2 | 12/2007 | Lee et al. |
| 7,309,849 B2 | 12/2007 | Truckai et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |
| 7,331,410 B2 | 2/2008 | Yong et al. |
| 7,335,165 B2 | 2/2008 | Truwit et al. |
| 7,353,068 B2 | 4/2008 | Tanaka et al. |
| 7,354,440 B2 | 4/2008 | Truckai et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| D576,725 S | 9/2008 | Shumer et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,494,468 B2 | 2/2009 | Rabiner et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,549,564 B2 | 6/2009 | Boudreaux |
| 7,559,450 B2 | 7/2009 | Wales et al. |
| 7,567,012 B2 | 7/2009 | Namikawa |
| 7,578,820 B2 | 8/2009 | Moore et al. |
| 7,654,431 B2 | 2/2010 | Hueil et al. |
| 7,665,647 B2 | 2/2010 | Shelton, IV et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,686,770 B2 | 3/2010 | Cohen |
| 7,691,098 B2 | 4/2010 | Wallace et al. |
| 7,699,846 B2 | 4/2010 | Ryan |
| 7,713,202 B2 | 5/2010 | Boukhny et al. |
| 7,714,481 B2 | 5/2010 | Sakai |
| D618,797 S | 6/2010 | Price et al. |
| 7,738,969 B2 | 6/2010 | Bleich |
| 7,740,594 B2 | 6/2010 | Hibner |
| 7,751,115 B2 | 7/2010 | Song |
| 7,770,774 B2 | 8/2010 | Mastri et al. |
| 7,770,775 B2 | 8/2010 | Shelton, IV et al. |
| 7,771,444 B2 | 8/2010 | Patel et al. |
| 7,780,054 B2 | 8/2010 | Wales |
| 7,780,659 B2 | 8/2010 | Okada et al. |
| 7,784,662 B2 | 8/2010 | Wales et al. |
| 7,798,386 B2 | 9/2010 | Schall et al. |
| 7,803,152 B2 | 9/2010 | Honda et al. |
| 7,806,891 B2 | 10/2010 | Nowlin et al. |
| 7,810,693 B2 | 10/2010 | Broehl et al. |
| 7,819,819 B2 | 10/2010 | Quick et al. |
| 7,824,401 B2 | 11/2010 | Manzo et al. |
| 7,837,699 B2 | 11/2010 | Yamada et al. |
| 7,846,155 B2 | 12/2010 | Houser et al. |
| 7,854,735 B2 | 12/2010 | Houser et al. |
| D631,155 S | 1/2011 | Peine et al. |
| 7,861,906 B2 | 1/2011 | Doll et al. |
| 7,876,030 B2 | 1/2011 | Taki et al. |
| D631,965 S | 2/2011 | Price et al. |
| 7,892,606 B2 | 2/2011 | Thies et al. |
| 7,901,423 B2 | 3/2011 | Stulen et al. |
| 7,905,881 B2 | 3/2011 | Masuda et al. |
| 7,922,651 B2 | 4/2011 | Yamada et al. |
| 7,959,050 B2 | 6/2011 | Smith et al. |
| 7,959,626 B2 | 6/2011 | Hong et al. |
| 7,976,544 B2 | 7/2011 | McClurken et al. |
| 7,981,050 B2 | 7/2011 | Ritchart et al. |
| 7,998,157 B2 | 8/2011 | Culp et al. |
| 8,038,693 B2 | 10/2011 | Allen |
| 8,061,014 B2 | 11/2011 | Smith et al. |
| 8,070,762 B2 | 12/2011 | Escudero et al. |
| 8,089,197 B2 | 1/2012 | Rinner et al. |
| 8,097,012 B2 | 1/2012 | Kagarise |
| 8,157,145 B2 | 4/2012 | Shelton, IV et al. |
| 8,177,800 B2 | 5/2012 | Spitz et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,502 B2 | 6/2012 | Smith et al. |
| 8,236,020 B2 | 8/2012 | Smith et al. |
| 8,253,303 B2 | 8/2012 | Giordano et al. |
| 8,273,087 B2 | 9/2012 | Kimura et al. |
| 8,287,485 B2 | 10/2012 | Kimura et al. |
| 8,323,302 B2 * | 12/2012 | Robertson et al. ............ 606/169 |
| 8,333,778 B2 | 12/2012 | Smith et al. |

(56) References Cited

U.S. PATENT DOCUMENTS

| | | | |
|---|---|---|---|
| 8,333,779 B2 | 12/2012 | Smith et al. | |
| 8,334,468 B2 | 12/2012 | Palmer et al. | |
| 8,338,726 B2 | 12/2012 | Palmer et al. | |
| 8,357,103 B2 | 1/2013 | Mark et al. | |
| 8,372,101 B2 | 2/2013 | Smith et al. | |
| 8,377,059 B2 | 2/2013 | Deville et al. | |
| 8,377,085 B2 | 2/2013 | Smith et al. | |
| 8,418,349 B2 | 4/2013 | Smith et al. | |
| 8,419,759 B2 * | 4/2013 | Dietz | 606/169 |
| 8,439,939 B2 | 5/2013 | Deville et al. | |
| 8,535,340 B2 | 9/2013 | Allen | |
| 8,535,341 B2 | 9/2013 | Allen | |
| 2001/0025183 A1 | 9/2001 | Shahidi et al. | |
| 2001/0025184 A1 | 9/2001 | Messerly | |
| 2001/0031950 A1 | 10/2001 | Ryan | |
| 2001/0039419 A1 | 11/2001 | Francischelli et al. | |
| 2002/0002377 A1 | 1/2002 | Cimino | |
| 2002/0019649 A1 | 2/2002 | Sikora et al. | |
| 2002/0022836 A1 | 2/2002 | Goble et al. | |
| 2002/0029055 A1 | 3/2002 | Bonutti | |
| 2002/0049551 A1 | 4/2002 | Friedman et al. | |
| 2002/0052617 A1 | 5/2002 | Anis et al. | |
| 2002/0077550 A1 | 6/2002 | Rabiner et al. | |
| 2002/0156466 A1 | 10/2002 | Sakurai et al. | |
| 2002/0156493 A1 | 10/2002 | Houser et al. | |
| 2003/0036705 A1 | 2/2003 | Hare et al. | |
| 2003/0050572 A1 | 3/2003 | Brautigam et al. | |
| 2003/0055443 A1 | 3/2003 | Spotnitz | |
| 2003/0204199 A1 | 10/2003 | Novak et al. | |
| 2003/0212332 A1 | 11/2003 | Fenton et al. | |
| 2003/0212422 A1 | 11/2003 | Fenton et al. | |
| 2003/0229344 A1 | 12/2003 | Dycus et al. | |
| 2004/0030254 A1 | 2/2004 | Babaev | |
| 2004/0047485 A1 | 3/2004 | Sherrit et al. | |
| 2004/0054364 A1 | 3/2004 | Aranyi et al. | |
| 2004/0092921 A1 | 5/2004 | Kadziauskas et al. | |
| 2004/0092992 A1 | 5/2004 | Adams et al. | |
| 2004/0097919 A1 | 5/2004 | Wellman et al. | |
| 2004/0097996 A1 | 5/2004 | Rabiner et al. | |
| 2004/0176686 A1 | 9/2004 | Hare et al. | |
| 2004/0199193 A1 | 10/2004 | Hayashi et al. | |
| 2004/0204728 A1 | 10/2004 | Haefner | |
| 2004/0243157 A1 | 12/2004 | Connor et al. | |
| 2004/0260300 A1 | 12/2004 | Gorensek et al. | |
| 2005/0021065 A1 | 1/2005 | Yamada et al. | |
| 2005/0033337 A1 | 2/2005 | Muir et al. | |
| 2005/0049546 A1 | 3/2005 | Messerly et al. | |
| 2005/0070800 A1 | 3/2005 | Takahashi | |
| 2005/0096683 A1 | 5/2005 | Ellins et al. | |
| 2005/0143769 A1 | 6/2005 | White et al. | |
| 2005/0149108 A1 | 7/2005 | Cox | |
| 2005/0165345 A1 | 7/2005 | Laufer et al. | |
| 2005/0177184 A1 | 8/2005 | Easley | |
| 2005/0182339 A1 | 8/2005 | Lee et al. | |
| 2005/0192610 A1 | 9/2005 | Houser et al. | |
| 2005/0209620 A1 | 9/2005 | Du et al. | |
| 2005/0261581 A1 | 11/2005 | Hughes et al. | |
| 2005/0261588 A1 | 11/2005 | Makin et al. | |
| 2005/0273090 A1 | 12/2005 | Nieman et al. | |
| 2005/0288659 A1 | 12/2005 | Kimura et al. | |
| 2006/0030797 A1 | 2/2006 | Zhou et al. | |
| 2006/0063130 A1 | 3/2006 | Hayman et al. | |
| 2006/0066181 A1 | 3/2006 | Bromfield et al. | |
| 2006/0079876 A1 | 4/2006 | Houser et al. | |
| 2006/0079878 A1 | 4/2006 | Houser | |
| 2006/0084963 A1 | 4/2006 | Messerly | |
| 2006/0095046 A1 | 5/2006 | Trieu et al. | |
| 2006/0190034 A1 | 8/2006 | Nishizawa et al. | |
| 2006/0206115 A1 | 9/2006 | Schomer et al. | |
| 2006/0211943 A1 | 9/2006 | Beaupre | |
| 2006/0235306 A1 | 10/2006 | Cotter et al. | |
| 2006/0253050 A1 | 11/2006 | Yoshimine et al. | |
| 2006/0264809 A1 | 11/2006 | Hansmann et al. | |
| 2007/0016235 A1 | 1/2007 | Tanaka et al. | |
| 2007/0016236 A1 | 1/2007 | Beaupre | |
| 2007/0055228 A1 | 3/2007 | Berg et al. | |
| 2007/0056596 A1 | 3/2007 | Fanney et al. | |
| 2007/0060915 A1 | 3/2007 | Kucklick | |
| 2007/0060935 A1 | 3/2007 | Schwardt et al. | |
| 2007/0063618 A1 | 3/2007 | Bromfield | |
| 2007/0106158 A1 * | 5/2007 | Madan et al. | 600/459 |
| 2007/0106317 A1 | 5/2007 | Shelton, IV et al. | |
| 2007/0129716 A1 | 6/2007 | Daw et al. | |
| 2007/0130771 A1 | 6/2007 | Ehlert et al. | |
| 2007/0131034 A1 | 6/2007 | Ehlert et al. | |
| 2007/0149881 A1 | 6/2007 | Rabin | |
| 2007/0162050 A1 | 7/2007 | Sartor | |
| 2007/0173872 A1 | 7/2007 | Neuenfeldt | |
| 2007/0185380 A1 | 8/2007 | Kucklick | |
| 2007/0219481 A1 | 9/2007 | Babaev | |
| 2007/0239028 A1 | 10/2007 | Houser et al. | |
| 2007/0249941 A1 | 10/2007 | Salehi et al. | |
| 2007/0260234 A1 | 11/2007 | McCullagh et al. | |
| 2007/0265560 A1 | 11/2007 | Soltani et al. | |
| 2007/0275348 A1 | 11/2007 | Lemon | |
| 2007/0282335 A1 | 12/2007 | Young et al. | |
| 2007/0287933 A1 | 12/2007 | Phan et al. | |
| 2008/0009848 A1 | 1/2008 | Paraschiv et al. | |
| 2008/0051812 A1 | 2/2008 | Schmitz et al. | |
| 2008/0058585 A1 | 3/2008 | Novak et al. | |
| 2008/0058775 A1 | 3/2008 | Darian et al. | |
| 2008/0058845 A1 | 3/2008 | Shimizu et al. | |
| 2008/0082039 A1 | 4/2008 | Babaev | |
| 2008/0082098 A1 | 4/2008 | Tanaka et al. | |
| 2008/0171938 A1 | 7/2008 | Masuda et al. | |
| 2008/0172051 A1 | 7/2008 | Masuda et al. | |
| 2008/0177268 A1 | 7/2008 | Daum et al. | |
| 2008/0188878 A1 | 8/2008 | Young | |
| 2008/0200940 A1 | 8/2008 | Eichmann et al. | |
| 2008/0208231 A1 | 8/2008 | Ota et al. | |
| 2008/0234708 A1 | 9/2008 | Houser et al. | |
| 2008/0234709 A1 | 9/2008 | Houser | |
| 2008/0234710 A1 | 9/2008 | Neurohr et al. | |
| 2008/0234711 A1 | 9/2008 | Houser et al. | |
| 2008/0243106 A1 | 10/2008 | Coe et al. | |
| 2008/0245371 A1 | 10/2008 | Gruber | |
| 2008/0249553 A1 | 10/2008 | Gruber et al. | |
| 2008/0262490 A1 | 10/2008 | Williams | |
| 2008/0281200 A1 | 11/2008 | Voic et al. | |
| 2008/0287948 A1 | 11/2008 | Newton et al. | |
| 2009/0030311 A1 | 1/2009 | Stulen et al. | |
| 2009/0030351 A1 | 1/2009 | Wiener et al. | |
| 2009/0030437 A1 | 1/2009 | Houser et al. | |
| 2009/0030438 A1 | 1/2009 | Stulen | |
| 2009/0030439 A1 | 1/2009 | Stulen | |
| 2009/0036911 A1 | 2/2009 | Stulen | |
| 2009/0036912 A1 | 2/2009 | Wiener et al. | |
| 2009/0036913 A1 | 2/2009 | Wiener et al. | |
| 2009/0036914 A1 | 2/2009 | Houser | |
| 2009/0048537 A1 | 2/2009 | Lydon et al. | |
| 2009/0054886 A1 | 2/2009 | Yachi et al. | |
| 2009/0054894 A1 | 2/2009 | Yachi | |
| 2009/0076506 A1 | 3/2009 | Baker | |
| 2009/0082716 A1 | 3/2009 | Akahoshi | |
| 2009/0105750 A1 | 4/2009 | Price et al. | |
| 2009/0118802 A1 | 5/2009 | Mioduski et al. | |
| 2009/0138006 A1 | 5/2009 | Bales et al. | |
| 2009/0143795 A1 | 6/2009 | Robertson | |
| 2009/0143797 A1 | 6/2009 | Smith et al. | |
| 2009/0143798 A1 | 6/2009 | Smith et al. | |
| 2009/0143799 A1 | 6/2009 | Smith et al. | |
| 2009/0143800 A1 | 6/2009 | Deville et al. | |
| 2009/0143801 A1 | 6/2009 | Deville et al. | |
| 2009/0143802 A1 | 6/2009 | Deville et al. | |
| 2009/0143803 A1 | 6/2009 | Palmer et al. | |
| 2009/0143804 A1 | 6/2009 | Palmer et al. | |
| 2009/0143805 A1 | 6/2009 | Palmer et al. | |
| 2009/0143806 A1 | 6/2009 | Witt et al. | |
| 2009/0149801 A1 | 6/2009 | Crandall et al. | |
| 2009/0270853 A1 | 10/2009 | Yachi et al. | |
| 2009/0270899 A1 | 10/2009 | Carusillo et al. | |
| 2009/0318945 A1 | 12/2009 | Yoshimine et al. | |
| 2009/0327715 A1 | 12/2009 | Smith et al. | |
| 2010/0004668 A1 | 1/2010 | Smith et al. | |

(56) References Cited

U.S. PATENT DOCUMENTS

| | | |
|---|---|---|
| 2010/0004669 A1 | 1/2010 | Smith et al. |
| 2010/0016785 A1 | 1/2010 | Takuma |
| 2010/0030248 A1 | 2/2010 | Palmer et al. |
| 2010/0036370 A1 | 2/2010 | Mirel et al. |
| 2010/0036405 A1 | 2/2010 | Giordano et al. |
| 2010/0069940 A1 | 3/2010 | Miller et al. |
| 2010/0158307 A1 | 6/2010 | Kubota et al. |
| 2010/0179577 A1 | 7/2010 | Houser |
| 2010/0187283 A1 | 7/2010 | Crainich et al. |
| 2010/0193567 A1 | 8/2010 | Scheib et al. |
| 2010/0228264 A1 | 9/2010 | Robinson et al. |
| 2010/0234906 A1 | 9/2010 | Koh |
| 2010/0268211 A1 | 10/2010 | Manwaring et al. |
| 2010/0280407 A1 | 11/2010 | Polster |
| 2010/0298743 A1 | 11/2010 | Nield et al. |
| 2010/0298851 A1 | 11/2010 | Nield |
| 2010/0331869 A1 | 12/2010 | Voegele et al. |
| 2010/0331870 A1 | 12/2010 | Wan et al. |
| 2010/0331871 A1 | 12/2010 | Nield et al. |
| 2010/0331872 A1 | 12/2010 | Houser et al. |
| 2011/0009850 A1 | 1/2011 | Main et al. |
| 2011/0015627 A1 | 1/2011 | DiNardo et al. |
| 2011/0015631 A1 | 1/2011 | Wiener et al. |
| 2011/0015660 A1 | 1/2011 | Wiener et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0087256 A1 | 4/2011 | Wiener et al. |
| 2011/0125175 A1 | 5/2011 | Stulen et al. |
| 2011/0196286 A1 | 8/2011 | Robertson et al. |
| 2011/0196287 A1 | 8/2011 | Robertson et al. |
| 2011/0196399 A1 | 8/2011 | Robertson et al. |
| 2011/0196400 A1 | 8/2011 | Robertson et al. |
| 2011/0196401 A1 | 8/2011 | Robertson et al. |
| 2011/0196402 A1 | 8/2011 | Robertson et al. |
| 2011/0196403 A1 | 8/2011 | Robertson et al. |
| 2011/0196404 A1 | 8/2011 | Dietz et al. |
| 2011/0196405 A1 | 8/2011 | Dietz |
| 2011/0270126 A1 | 11/2011 | Gunday et al. |
| 2011/0288452 A1 | 11/2011 | Houser et al. |
| 2012/0029546 A1 | 2/2012 | Robertson |
| 2012/0059289 A1 | 3/2012 | Nield et al. |
| 2012/0078139 A1 | 3/2012 | Aldridge et al. |
| 2012/0078247 A1 | 3/2012 | Worrell et al. |
| 2012/0083783 A1 | 4/2012 | Davison et al. |
| 2012/0083784 A1 | 4/2012 | Davison et al. |
| 2012/0132450 A1 | 5/2012 | Timm et al. |
| 2012/0138660 A1 | 6/2012 | Shelton, IV |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0203257 A1 | 8/2012 | Stulen et al. |
| 2012/0205421 A1 | 8/2012 | Shelton, IV |
| 2012/0210223 A1 | 8/2012 | Eppolito |
| 2012/0211546 A1 | 8/2012 | Shelton, IV |
| 2012/0259353 A1 | 10/2012 | Houser et al. |
| 2012/0265196 A1 | 10/2012 | Turner et al. |
| 2012/0269676 A1 | 10/2012 | Houser et al. |
| 2012/0289984 A1 | 11/2012 | Houser et al. |
| 2012/0310262 A1 | 12/2012 | Messerly et al. |
| 2012/0310263 A1 | 12/2012 | Messerly et al. |
| 2012/0310264 A1 | 12/2012 | Messerly et al. |
| 2012/0323265 A1 | 12/2012 | Stulen |
| 2013/0012970 A1 | 1/2013 | Houser |
| 2013/0245659 A1 | 9/2013 | Robertson et al. |
| 2013/0345733 A1 | 12/2013 | Robertson et al. |

FOREIGN PATENT DOCUMENTS

| | | |
|---|---|---|
| CN | 1694649 A | 11/2005 |
| CN | 1922563 A | 2/2007 |
| CN | 1951333 A | 4/2007 |
| CN | 101040799 A | 9/2007 |
| EP | 0171967 A2 | 2/1986 |
| EP | 0443256 A1 | 8/1991 |
| EP | 0456470 A1 | 11/1991 |
| EP | 0482195 B1 | 4/1992 |
| EP | 0482195 B1 | 1/1996 |
| EP | 0612570 B1 | 6/1997 |
| EP | 0908148 B1 | 1/2002 |
| EP | 0908155 B1 | 6/2003 |
| EP | 1199044 B1 | 12/2005 |
| EP | 1199043 B1 | 3/2006 |
| EP | 1433425 B1 | 6/2006 |
| EP | 1844720 A1 | 10/2007 |
| EP | 1862133 A1 | 12/2007 |
| EP | 1199045 B1 | 6/2008 |
| EP | 1974771 A1 | 10/2008 |
| EP | 1498082 B1 | 12/2008 |
| EP | 1832259 B1 | 6/2009 |
| EP | 2074959 A1 | 7/2009 |
| EP | 2298154 A2 | 3/2011 |
| GB | 2032221 A | 4/1980 |
| GB | 2379878 B | 11/2004 |
| GB | 2447767 B | 8/2011 |
| JP | 62-2292153 A | 12/1987 |
| JP | 63-315049 A | 12/1988 |
| JP | 02-71510 U | 5/1990 |
| JP | 04-25707 U | 2/1992 |
| JP | 4-30508 U | 3/1992 |
| JP | 6-104503 A | 4/1994 |
| JP | 6-507081 A | 8/1994 |
| JP | H 7-508910 A | 10/1995 |
| JP | 7-308323 A | 11/1995 |
| JP | 8-24266 A | 1/1996 |
| JP | 8-275951 A | 10/1996 |
| JP | H 09-503146 A | 3/1997 |
| JP | 10-295700 A | 11/1998 |
| JP | 11-253451 A | 9/1999 |
| JP | 2000-041991 A | 2/2000 |
| JP | 2000-070279 A | 3/2000 |
| JP | 2001-309925 A | 11/2001 |
| JP | 2002-186901 A | 7/2002 |
| JP | 2002-263579 A | 9/2002 |
| JP | 2003-510158 A | 3/2003 |
| JP | 2003-126110 A | 5/2003 |
| JP | 2003-310627 A | 5/2003 |
| JP | 2003-339730 A | 12/2003 |
| JP | 2005027026 A | 1/2005 |
| JP | 2005-066316 A | 3/2005 |
| JP | 2005-074088 A | 3/2005 |
| JP | 2005-534451 A | 11/2005 |
| JP | 2006-158525 A | 6/2006 |
| JP | 2006217716 A | 8/2006 |
| JP | 2008-508065 A | 3/2008 |
| JP | 2008-119250 A | 5/2008 |
| JP | 2009-511206 A | 3/2009 |
| JP | 2009-236177 | 10/2009 |
| WO | WO 92/22259 A2 | 12/1992 |
| WO | WO 93/14708 A1 | 8/1993 |
| WO | WO 94/21183 | 9/1994 |
| WO | WO 95/09572 A1 | 4/1995 |
| WO | WO 98/26739 A1 | 6/1998 |
| WO | WO 98/37815 A1 | 9/1998 |
| WO | WO 01/54590 A1 | 8/2001 |
| WO | WO 01/95810 A2 | 12/2001 |
| WO | WO 2004/037095 A2 | 5/2004 |
| WO | WO 2005/122917 A1 | 12/2005 |
| WO | WO 2006/012797 A1 | 2/2006 |
| WO | WO 2006/042210 A2 | 4/2006 |
| WO | WO 2006/058223 A2 | 6/2006 |
| WO | WO 2006/063199 A2 | 6/2006 |
| WO | WO 2006/083988 A1 | 8/2006 |
| WO | WO 2006/129465 A1 | 12/2006 |
| WO | WO 2007/008710 A2 | 1/2007 |
| WO | WO 2007/047531 A2 | 4/2007 |

(56) References Cited

FOREIGN PATENT DOCUMENTS

| WO | WO 2007/143665 A2 | 12/2007 |
| WO | WO 2008/016886 A2 | 2/2008 |
| WO | WO 2008/042021 A1 | 4/2008 |
| WO | WO 2008/130793 A1 | 10/2008 |
| WO | WO 2009/018406 A2 | 2/2009 |
| WO | WO 2009/027065 A1 | 3/2009 |
| WO | WO 2011/144911 A1 | 11/2011 |

OTHER PUBLICATIONS

Campbell et al, "Thermai Imaging in Surgery," p. 19-3, in *Medical Infrared Imaging*, N. A. Diakides and J. D. Bronzino, Eds. (2008).
U.S. Appl. No. 13/195,352, filed Aug. 1, 2011.
U.S. Appl. No. 29/402,697, filed Sep. 26, 2011.
U.S. Appl. No. 29/402,699, filed Sep. 26, 2011.
U.S. Appl. No. 29/402,700, filed Sep. 26, 2011.
U.S. Appl. No. 29/402,701, filed Sep. 26, 2011.
U.S. Appl. No. 13/270,459, filed Oct. 11, 2011.
U.S. Appl. No. 13/251,766, filed Oct. 3, 2011.
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
U.S. Appl. No. 12/703,860, filed Feb. 11, 2010.
U.S. Appl. No. 12/703,864, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.
U.S. Appl. No. 12/703,899, filed Feb. 11, 2010.
*Technology Overview*, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
U.S. Appl. No. 12/896,351, filed Oct. 1, 2010.
U.S. Appl. No. 12/896,479, filed Oct. 1, 2010.
U.S. Appl. No. 12/896,360, filed Oct. 1, 2010.
U.S. Appl. No. 12/896,345, filed Oct. 1, 2010.
U.S. Appl. No. 12/896,384, filed Oct. 1, 2010.
U.S. Appl. No. 12/896,467, filed Oct. 1, 2010.
U.S. Appl. No. 12/896,451, filed Oct. 1, 2010.
U.S. Appl. No. 12/896,470, filed Oct. 1, 2010.
U.S. Appl. No. 12/896,411, filed Oct. 1, 2010.
U.S. Appl. No. 12/896,420, filed Oct. 1, 2010.
Incropera et al., Fundamentals of Heat and Mass Transfer, Wiley, New York (1990).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in *Medical Infrared Imaging*, N. A. Diakides and J. D. Bronzino, Eds. (2008).
U.S. Appl. No. 29/404,676, filed Oct. 24, 2011.
U.S. Appl. No. 13/294,576, filed Nov. 11, 2011.
U.S. Appl. No. 13/448,175, filed Apr. 16, 2012.
U.S. Appl. No. 13/151,181, filed Jun. 2, 2011.
U.S. Appl. No. 13/369,561, filed Feb. 9, 2012.
U.S. Appl. No. 13/369,569, filed Feb. 9, 2012.
U.S. Appl. No. 13/369,578, filed Feb. 9, 2012.
U.S. Appl. No. 13/369,584, filed Feb. 9, 2012.
U.S. Appl. No. 13/369,588, filed Feb. 9, 2012.
U.S. Appl. No. 13/369,594, filed Feb. 9, 2012.
U.S. Appl. No. 13/369,601, filed Feb. 9, 2012.
U.S. Appl. No. 13/369,609, filed Feb. 9, 2012.
U.S. Appl. No. 13/369,629, filed Feb. 9, 2012.
U.S. Appl. No. 13/369,666, filed Feb. 9, 2012.
U.S. Appl. No. 13/545,292, filed Jul. 10, 2012.
U.S. Appl. No. 13/584,020, filed Aug. 13, 2012.
U.S. Appl. No. 13/584,445, filed Aug. 13, 2012.
U.S. Appl. No. 13/584,878, filed Aug. 14, 2012.
U.S. Appl. No. 13/585,124, filed Aug. 14, 2012.
U.S. Appl. No. 13/585,292, filed Aug. 14, 2012.
International Preliminary Report on Patentability for PCT/US2011/024190, Aug. 14, 2012 (8 pages).
U.S. Appl. No. 13/751,680, filed Jan. 28, 2013.
U.S. Appl. No. 14/076,472, filed Nov. 11, 2013.

\* cited by examiner

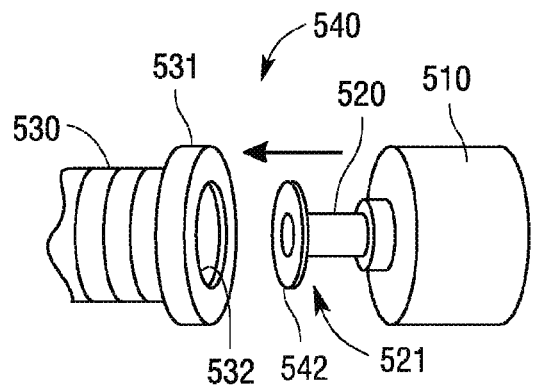
*Fig.11*
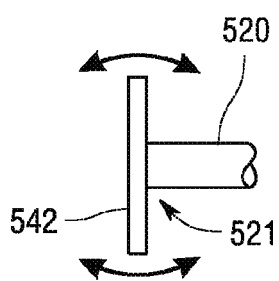 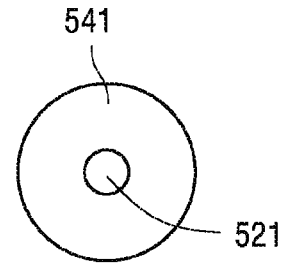
*Fig.12*     *Fig.13*
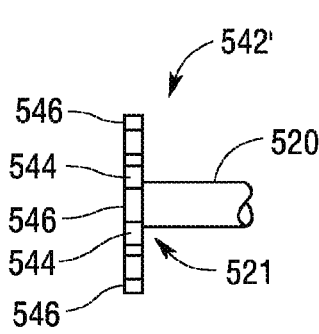 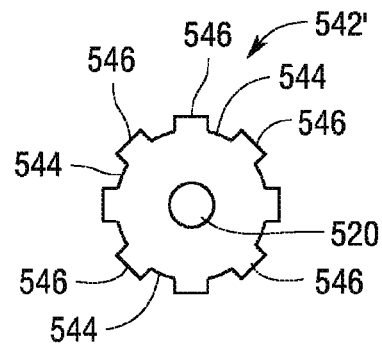
*Fig.14*     *Fig.15*

SEAL ARRANGEMENTS FOR ULTRASONICALLY POWERED SURGICAL INSTRUMENTS

BACKGROUND

The present disclosure generally relates to ultrasonic surgical systems and, more particularly, to ultrasonic systems that allow surgeons to perform cutting and coagulation of tissue.

Over the years, a variety of different types of non-ultrasonically powered cutters and shaving devices for performing surgical procedures have been developed. Some of these devices employ a rotary cutting instrument and other devices employ a reciprocating cutting member. For example, shavers are widely used in arthroscopic surgery. These devices generally consist of a power supply, a handpiece, and a single-use end effector. The end effector commonly has an inner and outer tube. The inner tube rotates relative to the outer tube and will cut tissue with its sharpened edges. The inner tube can rotate continuously or oscillate. In addition, such device may employ a suction channel that travels through the interior of the inner tube. For example, U.S. Pat. No. 4,850,354 to McGurk-Burleson, et al., discloses a non-ultrasonically powered surgical cutting instrument that comprises a rotary cutter for cutting material with a shearing action. It employs an inner cutting member which is rotatable within an outer tube.

U.S. Pat. No. 3,776,238 to Peyman et al. discloses an ophthalmic instrument in which tissue is cut by a chopping action set-up by the sharp end of an inner tube moving against the inner surface of the end of an outer tube. U.S. Pat. No. 5,226,910 to Kajiyama et al. discloses another surgical cutting instrument that has an inner member which moves relative to an outer member to cut tissue entering through an aperture in the outer member.

U.S. Pat. No. 4,922,902 to Wuchinich et al. discloses a method and apparatus for endoscopic removal of tissue utilizing an ultrasonic aspirator. The device uses an ultrasonic probe which disintegrates compliant tissue and aspirates it through a narrow orifice. U.S. Pat. No. 4,634,420 to Spinosa et al. discloses an apparatus and method for removing tissue from an animal and includes an elongated instrument having a needle or probe, which is vibrated at an ultrasonic frequency in the lateral direction. The ultrasonic movement of the needle breaks-up the tissue into fragments. Pieces of tissue can be removed from the area of treatment by aspiration through a conduit in the needle. U.S. Pat. No. 3,805,787 to Banko discloses yet another ultrasonic instrument that has a probe that is shielded to narrow the beam of ultrasonic energy radiated from the tip of the probe. In one embodiment the shield extends past the free-end of the probe to prevent the probe from coming into contact with the tissue. U.S. Pat. No. 5,213,569 to Davis discloses a phaco-emulsification needle which focuses the ultrasonic energy. The focusing surfaces can be beveled, curved or faceted. U.S. Pat. No. 6,984,220 to Wuchinich and U.S. Patent Publication No. US 2005/0177184 to Easley disclose ultrasonic tissue dissection systems that provide combined longitudinal and torsional motion through the use of longitudinal-torsional resonators. U.S. Patent Publication No. US 2006/0030797 A1 to Zhou et al. discloses an orthopedic surgical device that has a driving motor for driving an ultrasound transducer and horn. An adapter is provided between the driving motor and transducer for supplying ultrasonic energy signals to the transducer.

While the use of ultrasonically powered surgical instruments provide several advantages over traditional mechanically powered saws, drills, and other instruments, temperature rise in bone and adjacent tissue due to frictional heating at the bone/tissue interface can still be a significant problem. Current arthroscopic surgical tools include punches, reciprocating shavers and radio frequency (RF) devices. Mechanical devices such as punches and shavers create minimal tissue damage, but can sometimes leave behind ragged cut lines, which are undesirable. RF devices can create smoother cut lines and also ablate large volumes of soft tissue; however, they tend to create more tissue damage than mechanical means. Thus, device which could provide increased cutting precision while forming smooth cutting surfaces without creating excessive tissue damage would be desirable.

Arthroscopic surgery involves performing surgery in the joint space. To perform the surgery, the joints are commonly filled with pressurized saline for distention and visualization. Ultrasonic instruments which may be used in such surgeries must withstand the fluid pressure without leaking. However, conventional ultrasonic instruments generally experience significant forces during use. Current seals on ultrasonic devices are generally not robust enough to withstand this environment without leaking.

It would be desirable to provide an ultrasonic surgical instrument that overcomes some of the deficiencies of current instruments. The ultrasonic surgical instruments described herein overcome many of those deficiencies.

It would also be desirable to provide more robust sealing arrangements for ultrasonic surgical instruments used to cut and coagulate in the aqueous environment of arthroscopic surgery.

The foregoing discussion is intended only to illustrate some of the shortcomings present in the field of various embodiments of the invention at the time, and should not be taken as a disavowal of claim scope.

SUMMARY

In connection with one general aspect, there is provided an ultrasonic surgical instrument that includes a housing that operably supports an ultrasonic transducer assembly. A blade may be coupled to the ultrasonic transducer assembly and a hollow sheath may be coupled to the housing and extend axially around a portion of the blade. The instrument may further include a seal assembly for establishing a seal between a portion of the blade and the hollow sheath. In various embodiments, the seal assembly may comprise a first annular seal portion that is attached to the blade. Two axial seal portions may extend axially beyond the first annular seal portion in opposite axial directions from the first annular seal portion. The axial seal portions may be oriented in flexible sealing contact with corresponding portions of an inner wall of the hollow sheath.

In connection with another general aspect, there is provided an ultrasonic surgical instrument that includes a housing that operably supports an ultrasonic transducer assembly. A blade may be coupled to the ultrasonic transducer assembly and have an annular seal on a portion thereof. The instrument may further include a hollow sheath that comprises a first sheath segment and a second sheath segment that is attachable to the first sheath segment to form a substantially hollow lumen for receiving the portion of the blade therein. The first sheath segment and the second sheath segment may be configured relative to each other to form an annular groove within the hollow tube for sealingly receiving the annular seal therein when the first sheath segment and the second sheath segment are attached together and the portion of the blade is received within the hollow lumen.

In connection with still another general aspect, there is provided an ultrasonic surgical instrument that includes a housing that supports an ultrasonic transducer assembly therein. A blade may be coupled to the ultrasonic transducer assembly and a hollow sheath may be coupled to the housing and extend axially around a portion of the blade. The instrument may further include a seal assembly for establishing a seal between a portion of the blade and the hollow sheath. In various embodiments, the seal assembly may comprise an annular seal that is attached to the blade and a first annular ring member that protrudes from an inner wall of the hollow sheath adjacent a proximal end of the annular seal.

In connection with another general aspect, there is provided an ultrasonic surgical instrument that may include a housing that supports an ultrasonic transducer assembly therein. A blade may be coupled to the ultrasonic transducer assembly. A hollow sheath may be coupled to the housing and extend axially around a portion of the blade. The instrument may further include an annular seal that is attached to a portion of the blade. The annular seal may have an outer diameter that is greater than an inner diameter of the hollow sheath and further have a proximal side and a distal side such that when the portion of said blade is installed in the hollow sheath, a portion of the proximal side is in sealing engagement with an inner wall of the hollow sheath.

In connection with yet another general aspect, there is provided a method of creating a substantially fluid-tight seal between a blade of an ultrasonic surgical instrument and a hollow sheath of the instrument. Various forms of the method may include installing a seal on the cutting member wherein the seal has an annular groove therein and forming a portion of the hollow sheath into said annular groove in the seal.

FIGURES

The features of various non-limiting embodiments are set forth with particularity in the appended claims. The various non-limiting embodiments, however, both as to organization and methods of operation, together with further objects and advantages thereof, may best be understood by reference to the following description, taken in conjunction with the accompanying drawings as follows.

FIG. 11 is a partial exploded assembly view of a non-limiting coupling assembly embodiment for coupling a motor to a transducer assembly;

FIG. 12 is a side view of a thin plate member and drive shaft arrangement of a non-limiting coupling assembly embodiment;

FIG. 13 is an end view of the non-limiting thin plate member embodiment of FIG. 12;

FIG. 14 is a side view of a non-limiting thin plate member and drive shaft arrangement of another non-limiting coupling assembly embodiment;

FIG. 15 is an end view of the non-limiting thin plate member embodiment of FIG. 14;

DESCRIPTION

Figure 1:
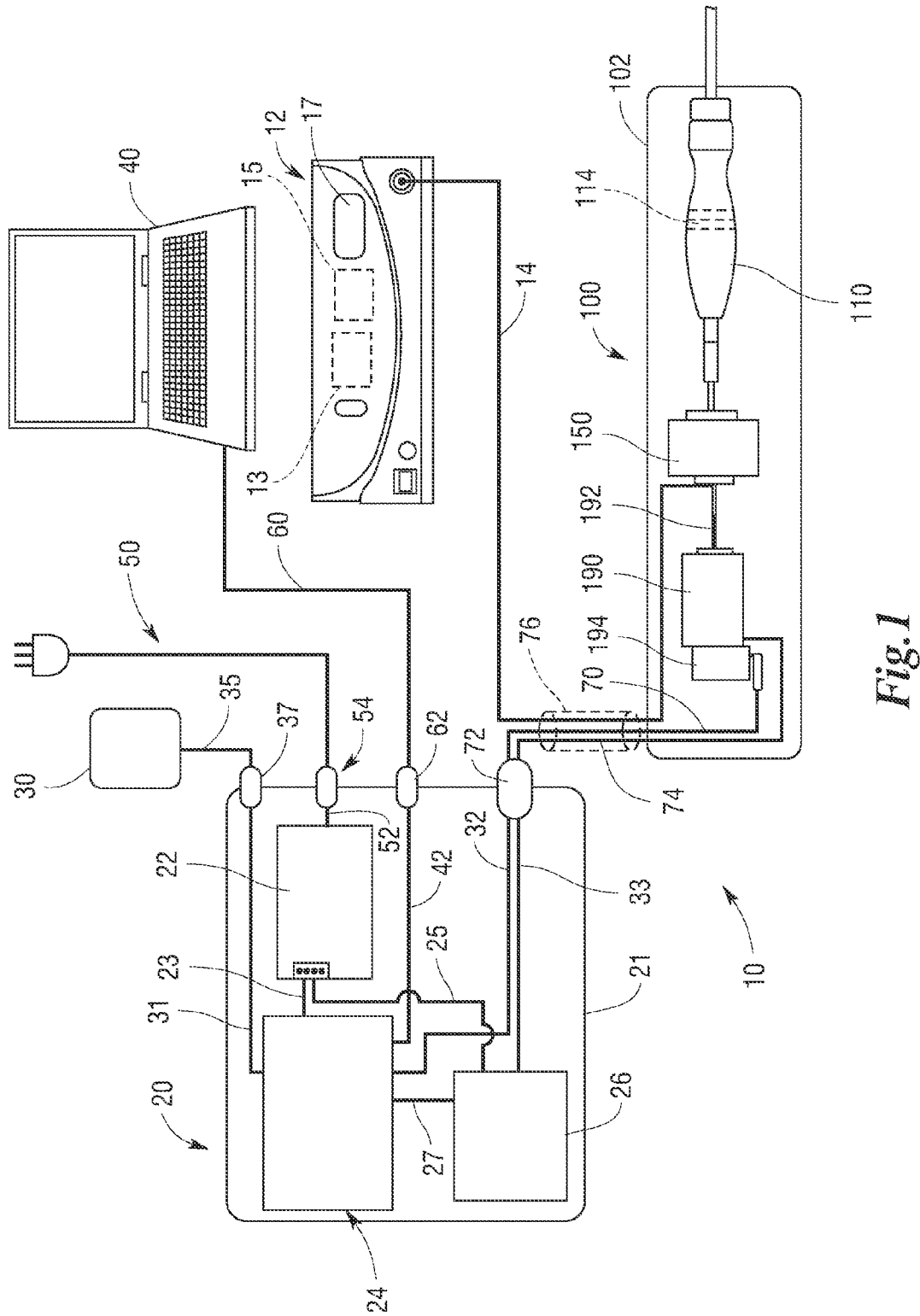
FIG. 1 is a schematic view of a non-limiting embodiment of a surgical control system.

The owner of the present application also owns the following U.S. patent applications that were filed on even date herewith and which are herein incorporated by reference in their respective entireties:

U.S. patent application Ser. No. 12/703,860, now U.S. Pat. No. 8,531,064, entitled ULTRASONICALLY POWERED SURGICAL INSTRUMENTS WITH ROTATING CUTTING IMPLEMENT;

U.S. patent application Ser. No. 12/703,864, now U.S. Pat. No. 8,323,302, entitled METHODS OF USING ULTRASONICALLY POWERED SURGICAL INSTRUMENTS WITH ROTATABLE CUTTING IMPLEMENTS;

U.S. patent application Ser. No. 12/703,870, now U.S. Patent Application Publication No. 2011-0196399 A1, entitled ULTRASONIC SURGICAL INSTRUMENTS WITH ROTATABLE BLADE AND HOLLOW SHEATH ARRANGEMENTS;

U.S. patent application Ser. No. 12/703,875, now U.S. Pat. No. 8,469,981, entitled ROTATABLE CUTTING IMPLEMENT ARRANGEMENTS FOR ULTRASONIC SURGICAL INSTRUMENTS;

U.S. patent application Ser. No. 12/703,877, now U.S. Pat. No. 8,382,782, entitled ULTRASONIC SURGICAL INSTRUMENTS WITH PARTIALLY ROTATING BLADE AND FIXED PAD ARRANGEMENT;

U.S. patent application Ser. No. 12/703,879, now U.S. Pat. No. 8,486,096, entitled DUAL PURPOSE SURGICAL INSTRUMENT FOR CUTTING AND COAGULATING TISSUE;

U.S. patent application Ser. No. 12/703,885, now U.S. Pat. No. 8,579,828, entitled OUTER SHEATH AND BLADE ARRANGEMENTS FOR ULTRASONIC SURGICAL INSTRUMENTS;

U.S. patent application Ser. No. 12/703,893, now U.S. Patent Application Publication No. 2011-0196404 A1, entitled ULTRASONIC SURGICAL INSTRUMENTS WITH MOVING CUTTING IMPLEMENT; and U.S. patent application Ser. No. 12/703,899, now U.S. Pat. No. 8,419,759, entitled ULTRASONIC SURGICAL INSTRUMENT WITH COMB-LIKE TISSUE TRIMMING DEVICE.

Various embodiments are directed to apparatuses, systems, and methods for the treatment of tissue Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

Various embodiments are directed to improved ultrasonic surgical systems and instruments configured for effecting tissue dissecting, cutting, and/or coagulation during surgical procedures as well as the cutting implements and sealing features employed thereby. In one embodiment, an ultrasonic surgical instrument apparatus is configured for use in open surgical procedures, but has applications in other types of surgery, such as laparoscopic, endoscopic, and robotic-assisted procedures. Versatile use is facilitated by selective use of ultrasonic energy and the selective rotation of the cutting/coagulation implement.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

Surgical Systems

FIG. 1 illustrates in schematic form one non-limiting embodiment of a surgical system 10. The surgical system 10 may include a ultrasonic generator 12 and an ultrasonic surgical instrument assembly 100 that may include a "self-contained" ultrasonic instrument 110. As will be discussed in further detail below, the ultrasonic generator 12 may be connected by a cable 14 to an ultrasonic transducer assembly 114 of the self-contained ultrasonic instrument 110 by a slip ring assembly 150 located in a housing portion 102 of the surgical instrument assembly 100. In one embodiment, the system 10 further includes a motor control system 20 that includes a power supply 22 that is coupled to a control module 24 by cable 23 to supply, for example, 24VDC thereto. The motor control module 24 may comprise a control module manufactured by National Instruments of Austin, Texas under Model No. NI cRIO-9073. However, other motor control modules may be employed. The power supply 22 may comprise a power supply manufactured by National Instruments. However, other power supplies may be successfully employed. The power supply 22 may be further coupled to a motor drive 26 by cable 25 to also supply 24VDC thereto. The motor drive 26 may comprise a motor drive manufactured by National Instruments. Control module 24 may also be coupled to the motor drive 26 by cable 27 for supplying power thereto. A conventional foot pedal 30 or other control switch arrangement may be attached to the control module 24 by a cable 31. As will be discussed in further detail below, the ultrasonic surgical instrument 100 may include a motor 190 that has an encoder 194 associated therewith. The motor 190 may comprise a motor manufactured by National Instruments under Model No. CTP12ELF10MAA00. The encoder 194 may comprise an encoder manufactured by U.S. Digital of Vancouver, Washington under Model No. E2-500-197-I-D-D-B. However, other motors and encoders may be used. The encoder 194 may be coupled to the motor control module 24 by an encoder cable 32 and the motor 190 may be coupled to the motor drive 26 by cable 33. The surgical system 10 may also include a computer 40 that may communicate by Ethernet cable 42 with the motor control module 24.

As can also be seen in FIG. 1, in various embodiments, the motor control system 20 is housed in an enclosure 21. To facilitate easy portability of the system, various components may be attached to the motor control system 20 by removable cable connectors. For example, foot pedal switch 30 may be attached to a detachable cable connector 37 by cable 35 to facilitate quick attachment of the foot pedal to the control system 20. A/C power may be supplied to the power supply 22 by a conventional plug/cable 50 that is attached to a detachable cable connector 54 that is attached to cable 52. The computer 40 may have a cable 60 that is attached to detachable cable connector 62 that is coupled to cable 42. The encoder 194 may have an encoder cable 70 that is attached to a detachable connector 72. Likewise, the motor 190 may have a cable 74 that is attached to the detachable connector 72. The detachable connector 72 may be attached to the control module 24 by cable 32 and the connector 72 may be attached to the motor drive 26 by cable 33. Thus, cable connector 72 serves to couple the encoder 194 to the control module 24 and the motor 190 to the motor drive 26. The cables 70 and 74 may be housed in a common sheath 76.

Figure 1A:
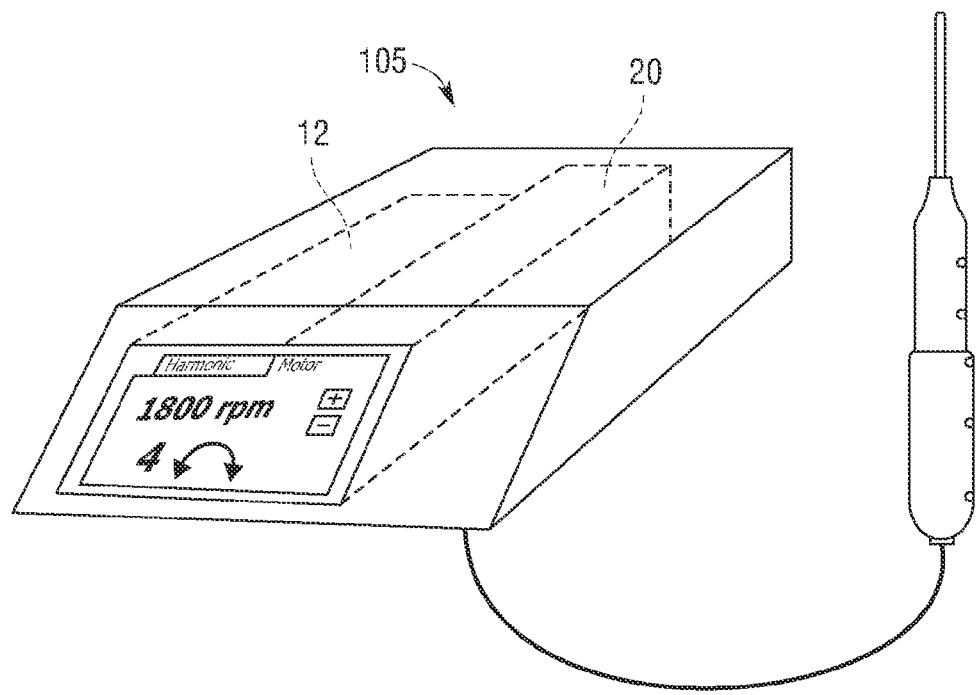
FIG. 1A is a perspective view of a non-limiting embodiment of control system enclosure.
Figure 1B:
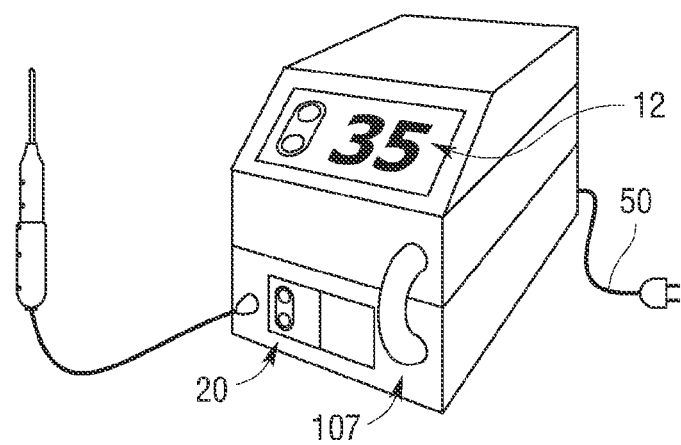
FIG. 1B is a perspective view of another non-limiting embodiment of a control system enclosure arrangement.

In an alternative embodiment, the ultrasonic generator 12 and the control system 20 may be housed in the same enclosure 105. See FIG. 1A. In yet another embodiment, the ultrasonic generator 12 may electrically communicate with the motor control system 20 by a jumper cable 107. Such arrangement may share a data link as well as a common means for supplying power (cord 50). See FIG. 1B.

In various embodiments, the ultrasonic generator 12 may include an ultrasonic generator module 13 and a signal generator module 15. See FIG. 1. The ultrasonic generator module 13 and/or the signal generator module 15 each may be integrated with the ultrasonic generator 12 or may be provided as a separate circuit module electrically coupled to the ultrasonic generator 12 (shown in phantom to illustrate this option). In one embodiment, the signal generator module 15 may be formed integrally with the ultrasonic generator module 13. The ultrasonic generator 12 may comprise an input device 17 located on a front panel of the generator 12 console. The input device 17 may comprise any suitable device that generates signals suitable for programming the operation of the generator 12 in a known manner. Still with reference to FIG. 1, the cable 14 may comprise multiple electrical conductors for the application of electrical energy to positive (+) and negative (−) electrodes of an ultrasonic transducer assembly 114 as will be discussed in further detail below.

Various forms of ultrasonic generators, ultrasonic generator modules and signal generator modules are known. For example, such devices are disclosed in commonly owned U.S. patent application Ser. No. 12/503,770, entitled Rotating Transducer Mount For Ultrasonic Surgical Instruments, filed Jul. 15, 2007, which is herein incorporated by reference in its entirety. Other such devices are disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting a Loose Blade in a Handle Connected to an Ultrasonic Surgical System); U.S. Pat. No. 6,626,926 (Method for Driving an Ultrasonic System to Improve Acquisition of Blade Resonance Frequency at Startup); U.S. Pat. No. 6,633,234 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,621 (Output Displacement Control Using Phase Margin in an Ultrasonic Surgical Handle); U.S. Pat. No. 6,679,899 (Method for Detecting Transverse Vibrations in an Ultrasonic Handle); U.S. Pat. No. 6,908,472 (Apparatus and Method for Altering Generator Functions in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

Surgical Instruments

Figure 2:
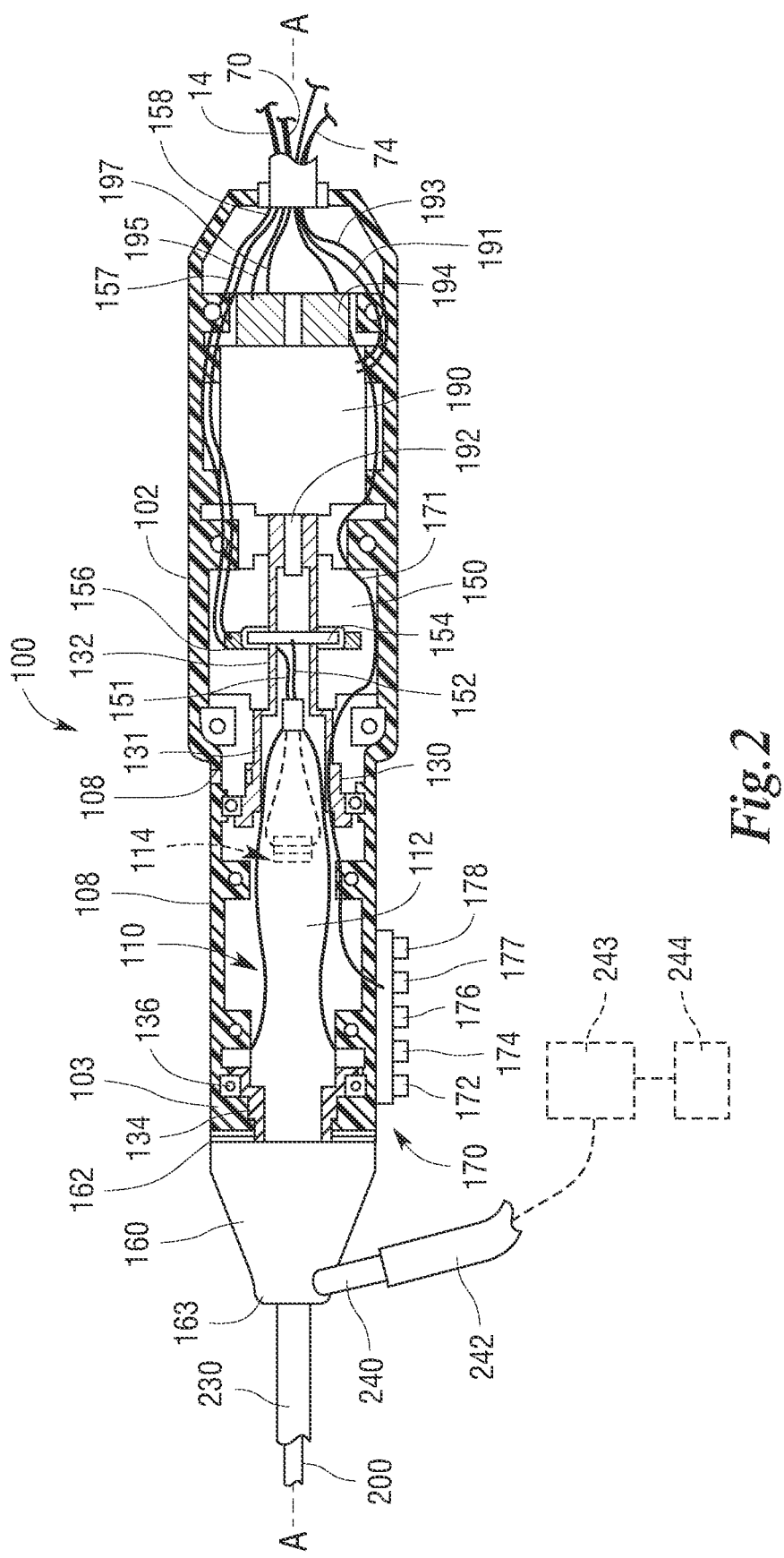
FIG. 2 is a cross-sectional view of a non-limiting embodiment of a handpiece.

As can be seen in FIG. 2, an ultrasonic surgical instrument handpiece 100 may comprise a housing 102 that houses the motor 190, the encoder 194, the slip ring assembly 150 and the self-contained ultrasonic surgical instrument 110. The housing 102 may be provided in two or more parts that are attached together by fasteners such as screws, snap features, etc. and may be fabricated from, for example, polycarbonate material. The motor 190 may comprise, for example, a stepper motor manufactured by National Instruments under Model No. CTP12ELF10MAA00. However other motors may be employed to effectuate, for example, "gross" rotational motion of the self-contained ultrasonic surgical instrument 110 relative to the housing 102 on the order of 1-6000 rpm. The encoder 194 converts the mechanical rotation of the motor shaft 192 into electrical pulses that provide speed and other motor control information to the control module 24.

Figure 3:
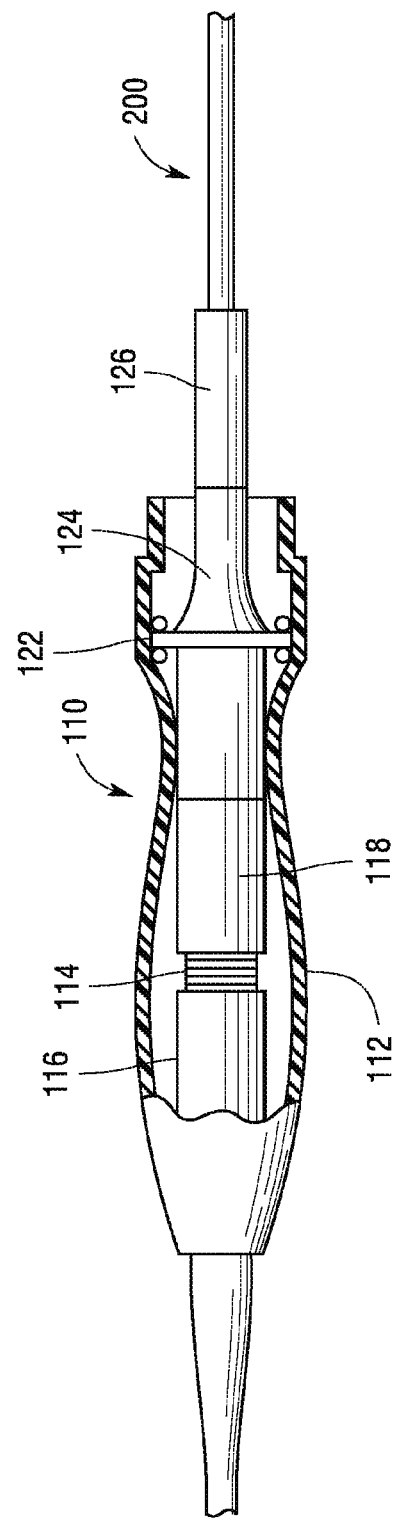
FIG. 3 is a partial cross-sectional view of an ultrasonic surgical handpiece that may be employed with various non-limiting embodiments.

The self-contained ultrasonic surgical instrument 110 may comprise a surgical instrument that is manufactured and sold by Ethicon Endo-Surgery under Model No. HP054. However, other ultrasonic instruments may be successfully employed. It will be understood that the term "self-contained" as used herein means that the ultrasonic surgical instrument may be effectively used as an ultrasonic surgical instrument on its own, apart from use with the surgical instrument 100. As illustrated in more detail in FIG. 3, the ultrasonic surgical instrument 110 includes a housing 112 that supports a piezo-electric ultrasonic transducer assembly 114 for converting electrical energy to mechanical energy that results in longitudinal vibrational motion of the ends of the transducer assembly 114. The ultrasonic transducer assembly 114 may comprise a stack of ceramic piezoelectric elements with a motion null point located at some point along the stack. The ultrasonic transducer assembly 114 may be mounted between two cylinders 116 and 118. In addition, a cylinder 120 may be attached to cylinder 118, which in turn is mounted to the housing at another motion null point 122. A horn 124 may also be attached at the null point on one side and to a coupler 126 on the other side. A blade 200 may be fixed to the coupler 126. As a result, the blade 200 will vibrate in the longitudinal direction at an ultrasonic frequency rate with the ultrasonic transducer assembly 114. The ends of the ultrasonic transducer assembly 114 achieve maximum motion with a portion of the stack constituting a motionless node, when the ultrasonic transducer assembly 114 is driven at maximum current at the transducer's resonant frequency. However, the current providing the maximum motion will vary with each instrument and is a value stored in the non-volatile memory of the instrument so the system can use it.

The parts of the ultrasonic instrument 110 may be designed such that the combination will oscillate at the same resonant frequency. In particular, the elements may be tuned such that the resulting length of each such element is one-half wavelength or a multiple thereof. Longitudinal back and forth motion is amplified as the diameter closer to the blade 200 of the acoustical mounting horn 124 decreases. Thus, the horn 124 as well as the blade/coupler may be shaped and dimensioned so as to amplify blade motion and provide ultrasonic vibration in resonance with the rest of the acoustic system, which produces the maximum back and forth motion of the end of the acoustical mounting horn 124 close to the blade 200. A motion from 20 to 25 microns at the ultrasonic transducer assembly 114 may be amplified by the horn 124 into blade movement of about 40 to 100 microns.

When power is applied to the ultrasonic instrument 110 by operation of the foot pedal 30 or other switch arrangement, the control system 20 may, for example, cause the blade 200 to vibrate longitudinally at approximately 55.5 kHz, and the amount of longitudinal movement will vary proportionately with the amount of driving power (current) applied, as adjustably selected by the user. When relatively high cutting power is applied, the blade 200 may be designed to move longitudinally in the range of about 40 to 100 microns at the ultrasonic vibrational rate. Such ultrasonic vibration of the blade 200 will generate heat as the blade contacts tissue, i.e., the acceleration of the blade 200 through the tissue converts the mechanical energy of the moving blade 200 to thermal energy in a very narrow and localized area. This localized heat creates a narrow zone of coagulation, which will reduce or eliminate bleeding in small vessels, such as those less than one millimeter in diameter. The cutting efficiency of the blade 200, as well as the degree of hemostasis, will vary with the level of driving power applied, the cutting rate or force applied by the surgeon to the blade, the nature of the tissue type and the vascularity of the tissue.

As can be seen in FIG. 2, the ultrasonic instrument 110 is supported within the housing 102 by a tailpiece drive adapter 130 and a distal handpiece adapter 134. The tailpiece drive adapter 130 is rotatably supported within housing 102 by a proximal bearing 132 and is non-rotatably coupled to the output shaft 192 of the motor 190. See FIG. 2. The tailpiece drive adapter 130 may be pressed onto the housing 112 of the ultrasonic instrument 110 or, for example, be attached to the housing 112 by setscrews or adhesive. The distal handpiece adapter 134 may be pressed onto a distal end 113 of the handpiece housing 112 or be otherwise attached thereto by set screws or adhesive. The distal handpiece adapter 134 is rotatably supported in the housing 102 by a distal bearing 136 that is mounted within housing 102.

When power is applied to motor 190, motor 190 applies a "gross rotational motion" to the handpiece 110 to cause the ultrasonic surgical instrument 110 and blade 200 to rotate about central axis A-A. As used herein, the term "gross rotational motion" is to be distinguished from that "torsional ultrasonic motion" that may be achieved when employing a non-homogeneous formed ultrasonic blade. The term "gross rotational motion" instead encompasses rotational motion that is not solely generated by operation of the ultrasonic transducer assembly 114.

To provide the ultrasonic instrument 110 with power from the ultrasonic generator 12, a slip ring assembly 150 may be employed. As can be seen in FIG. 2, conductors 151, 152 are coupled to the ultrasonic transducer assembly 114 and extend through a hollow stem portion 132 of the tail piece drive adapter 130. The hollow stem portion 132 is attached to the drive shaft 192 of the motor 190 and is free to rotate within the slip ring assembly 150. A first inner contact 154 is attached to the hollow stem portion 132 for rotational travel therewith about axis A-A. The first inner contact 154 is positioned for rotational contact with a fixed outer contact 156 within the slip ring assembly 150. The contacts 154, 156 may be provided in the form of concentrically arranged rings. Conductors 157, 158 are coupled to the fixed outer contact 156 and form generator cable 14. Conductors 191 and 193 are attached to the motor and form motor cable 74 and conductors 195, 197 are attached to encoder 194 and form encoder cable 70. Rotation of the motor shaft 192 results in the rotation of the tailpiece drive adapter 130 and the ultrasonic instrument 110 attached thereto about axis A-A. Rotation of the motor drive shaft 192 also results in the rotation of the inner contact 154. Ultrasonic signals from the ultrasonic generator 12 are transferred to the inner contact 154 by virtue of contact or "electrical communication" between the inner contact 154 and the outer contact 156. Those signals are transmitted to the ultrasonic transducer assembly 114 by conductors 151, 152. In other alternative embodiments, the slip ring assembly may employ use of conventional pogo pins that engage concentric ring contacts. Other slip ring arrangements could also be employed.

Various embodiments also include a distal nosepiece 160 that may be removably attached to the distal end 103 of the housing 102 by fasteners 161. See FIG. 5. One or more shim members 162 may be positioned between the distal end 103 and the nosepiece 160 to facilitate coaxial attachment between the housing 102 and the nosepiece 160. The nosepiece 160 may be fabricated from, for example, stainless steel or polycarbonate. In various embodiments, the distal end 202 of the blade 200 extends through a hollow coupler segment 210 that is journaled within an inner sheath seal 212. Inner sheath seal 212 may comprise, for example, polytetrafluoroethylene (PTFE"), and serve to establish a substantially fluid-tight and/or airtight seal between the coupler segment 210 and the nosepiece 160. Also in the embodiment of FIG. 4, an inner sheath 220 may be attached to the hollow coupler segment 210 by, for example, welding or the hollow coupler segment 210 may comprise an integral portion of the inner sheath 220. In one embodiment, a blade pin/torquing member 216 may extend transversely through the blade member 200 and the hollow coupler segment 210 to facilitate movement of the inner sheath 220 with the blade member 200. One or more vented silicone bushings 214 may be journaled around the blade 200 to acoustically isolate the blade 200 from the inner sheath 220. The blade member 200 may have a proximal end 201 that is internally threaded and adapted to removably engage a threaded portion of the coupler 126. To facilitate tightening of the blade 200 to the coupler 126, a tightening hole 108 (FIG. 2) may be provided through the housing 102 to enable a tool (e.g., Allen wrench) to be inserted therethrough into a hole 131 in the tail piece drive adapter 130 to prevent the rotation of the ultrasonic surgical instrument 110 and coupler 126 attached thereto. Once the blade 200 has been screwed onto the coupler 126, the user may remove the Allen wrench or other tool from holes 108, 131 and insert a threaded plug (not shown) into hole 108 to prevent fluids/debris from entering the housing 102 therethrough.

Figure 4:
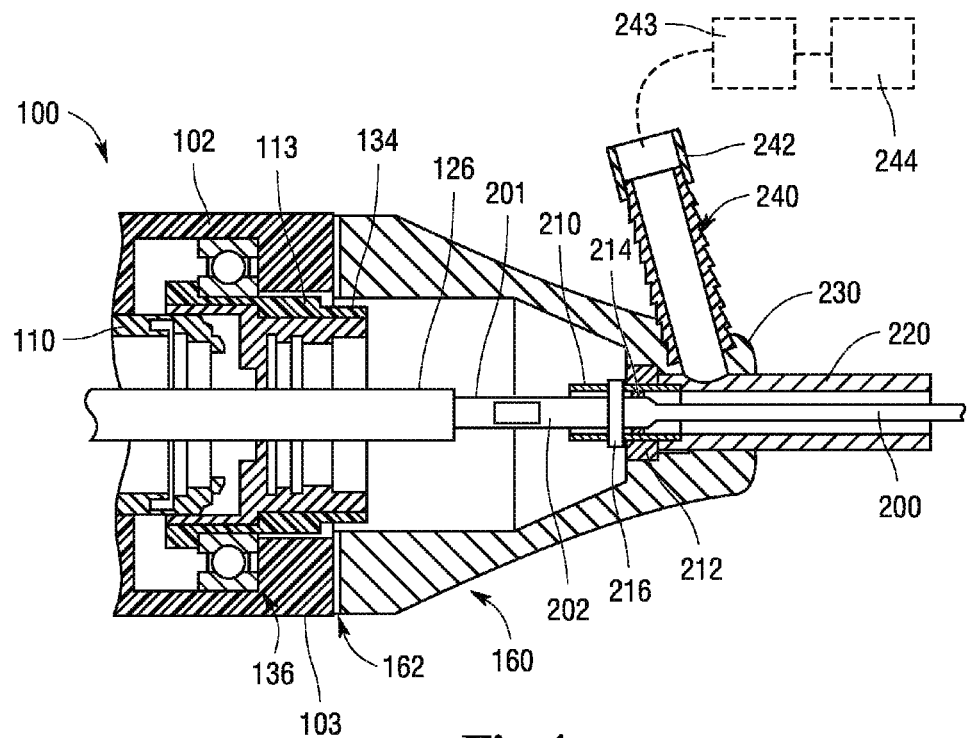
FIG. 4 is a cross-sectional view of a portion of a non-limiting nosepiece embodiment.
Figure 5:
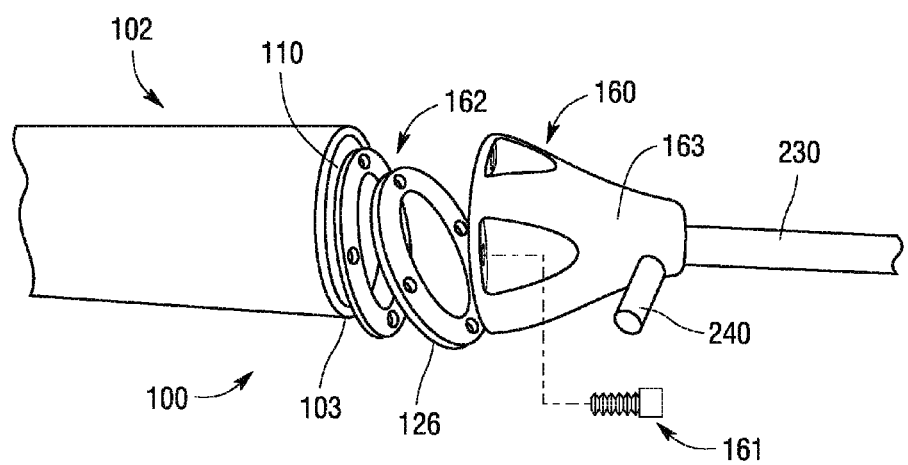
FIG. 5 is a partial exploded assembly view of a non-limiting nosepiece embodiment.

Also in various embodiments, an outer sheath 230 may be coaxially aligned with the inner sheath 220 and blade member 200 and be attached to a distal end 163 of nosepiece 160 by, for example, welding, brazing, overmolding or pressfit. As can be seen in FIG. 4, a suction port 240 may be attached to the nosepiece 160 to communicate with the hollow outer sheath 230. A flexible tube 242 may be attached to the suction port 240 and communicate with a collection receptacle 243 that is coupled to a source of vacuum, generally depicted as 244. Thus, the outer sheath 230 forms a suction path extending around the inner sheath 220 that begins at a distal tip of the outer sheath 230 and goes out through the suction port 240. Those of ordinary skill in the art will appreciate that alternate suction paths are also possible. In addition, in alternative embodiments, the inner sheath 220 is omitted.

Various embodiments of the surgical system 10 provide the ability to selectively apply ultrasonic axial motion to the blade 200 and gross rotational motion to the blade 200 as well. If desired, the clinician may simply activate the ultrasonic transducer assembly 114 without activating the motor 190. In such cases, the instrument 100 may be used in ultrasonic mode simply as an ultrasonic instrument. Frequency ranges for longitudinal ultrasonic motion may be on the order of, for example, 30-80 kHz. Similarly, the clinician may desire to active the motor 190 without activating the ultrasonic transducer assembly 114. Thus, gross rotational motion will be applied to the blade 200 in the rotation mode, without the application of longitudinal ultrasonic motion thereto. Gross rotational speeds may be, for example, on the order of 1-6000 rpm. In other applications, the clinician may desire to use the instrument 100 in the ultrasonics and rotational modes wherein the blade 200 will experience longitudinal ultrasonic motion from the transducer assembly 114 and gross rotational motion from the motor. Oscillatory motion of, for example, 2 to 10 revolutions per cycle (720 to 3600 degrees) or continuous unidirectional rotation may be achieved. Those of ordinary skill in the art will readily appreciate that various embodiments of the surgical system 10 may be effectively employed in connection with arthroscopic as well as other surgical applications.

At least one non-limiting embodiment may further include a control arrangement 170 on the housing 102. See FIG. 2. The control arrangement 170 may communicate with the control module 24 by multi-conductor cable 171. The control arrangement 170 may include a first button 172 for activating/deactivating a "dual" mode that includes the "ultrasonic mode" and "rotational mode". In such arrangements, the control module 24 may be pre-programmed to provide a pre-set amount of gross rotational motion to the blade 200. The control arrangement 170 may further include a second button 174 for activating/deactivating the rotational mode without activating the ultrasonics mode to thereby cut without hemostasis. The control arrangement 170 may also include a third button 176 for activating/deactivating a "coagulation mode" wherein the motor 190 drives to a pre-set rotational orientation and then "parks" or deactivates, thereby exposing the ultrasonic blade surface at the distal end of the outer sheath 240 as will be discussed in further detail below. Also in this mode, the ultrasonic transducer assembly 114 may be powered to provide spot coagulation or in an alternative embodiment, the clinician may simply activate a spot coagulation button 77 which activates the ultrasonic transducer assembly 114 for a preset time period of, for example, five seconds. The control arrangement may further include a button 178 to switch between ultrasonics and rotational modes. In accordance with various non-limiting embodiments, any combinations of the aforementioned functions/modes may be combined and controlled by one or more buttons without departing from the spirit and scope of the various non-limiting embodiments disclosed herein as well as their equivalent structures.

Those of ordinary skill in the art will understand that the housing member 102 and the mounting adapters 130 and 134 may be configured to operably support various different types and shapes of ultrasonic handpieces therein that may be independently used apart from the surgical instrument 100. Thus, the control system 20 and instrument 100 may be provided in "kit form" without the ultrasonic handpiece 110 to enable the purchaser to install their existing ultrasonic handpiece therein without departing from the spirit and scope of the various non-limiting embodiments disclosed herein as well as their respective equivalent structures.

Figure 6:
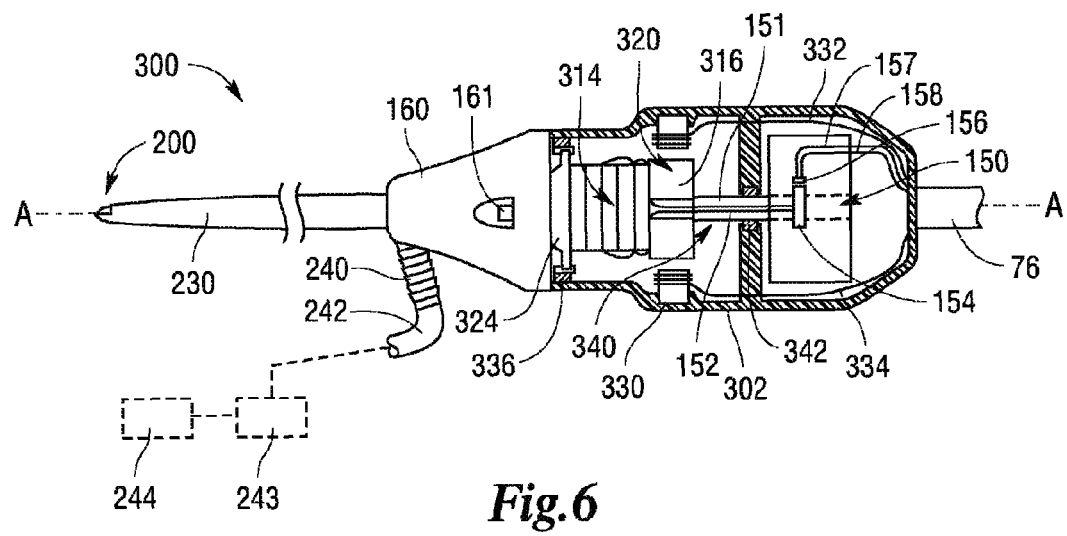
FIG. 6 is a partial cross-sectional view of a non-limiting embodiment of a surgical instrument handpiece.
Figure 7:
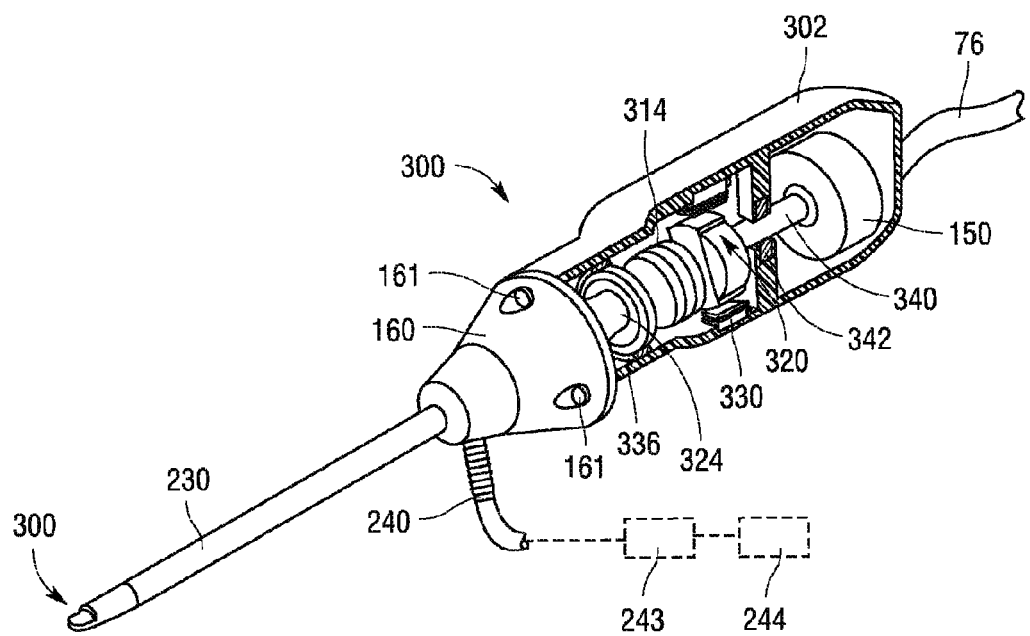
FIG. 7 is a perspective view of the non-limiting surgical instrument handpiece embodiment of FIG. 6.

FIGS. 6 and 7 illustrate another surgical instrument 300 wherein like numbers previously used to describe the various embodiments discussed above are used to designate like components. In these embodiments, the surgical instrument 300 includes a housing 302 that houses a transducer assembly 314 that is attached to an ultrasonic horn 324. The ultrasonic horn 324 may be coupled to the proximal end 201 of the blade 200 in the manner described above. The ultrasonic horn 324 may be rotatably supported within the housing 302 by a distal bearing 336. A nosepiece 160 may be attached to the housing 302 by fasteners 161 in the manner described above.

In this embodiment, the ultrasonic transducer assembly 314 has magnets 316 embedded or otherwise attached thereto to form an integral motor rotor, generally designated as 320. A motor stator ring 330 is mounted within the housing 302 as shown. Conductors 332, 334 are attached to the motor stator ring 330 and pass through the common sheath 76 to be attached to the motor cable 33 in the control system 20 as described above. A hollow shaft 340 extends through the motor rotor 320 to form a passage for conductors 151, 152. Conductors 151, 152 are coupled to the ultrasonic transducer assembly 314 and an inner contact 154. The inner contact 154 is attached to a portion of the hollow shaft 340 that rotatably extends into a slip ring assembly 150 that is also supported within the housing 302. The hollow shaft 340 is rotatably supported within the housing 302 by a proximal bearing 342. The slip ring assembly 150 is fixed (i.e., non-rotatable) within the housing 302 and includes a fixed outer contact 156 that is coupled to conductors 157, 158 that form generator cable 14 as was described above. When power is supplied to the motor stator 330, the rotor 320 and the integral ultrasonic transducer 314 are caused to rotate about axis A-A. Ultrasonic signals from the ultrasonic generator 12 are transferred to the inner contact 154 by virtue of rotating contact or electrical communication between the inner contact 154 and the outer contact 156. Those signals are transmitted to the ultrasonic transducer assembly 314 by conductors 151, 152. The surgical instrument 300 may include a control arrangement of the type described above and be used in the various modes described above. A suction may be applied between the blade 200 and outer sheath 230 through port 240. A collection receptacle 243 and source of suction 240 may be attached to the port 240 by tube 242. The distal end of the blade is exposed through a window in the distal end of the outer sheath 230 to expose the blade to tissue as will be further discussed below.

Figure 8:
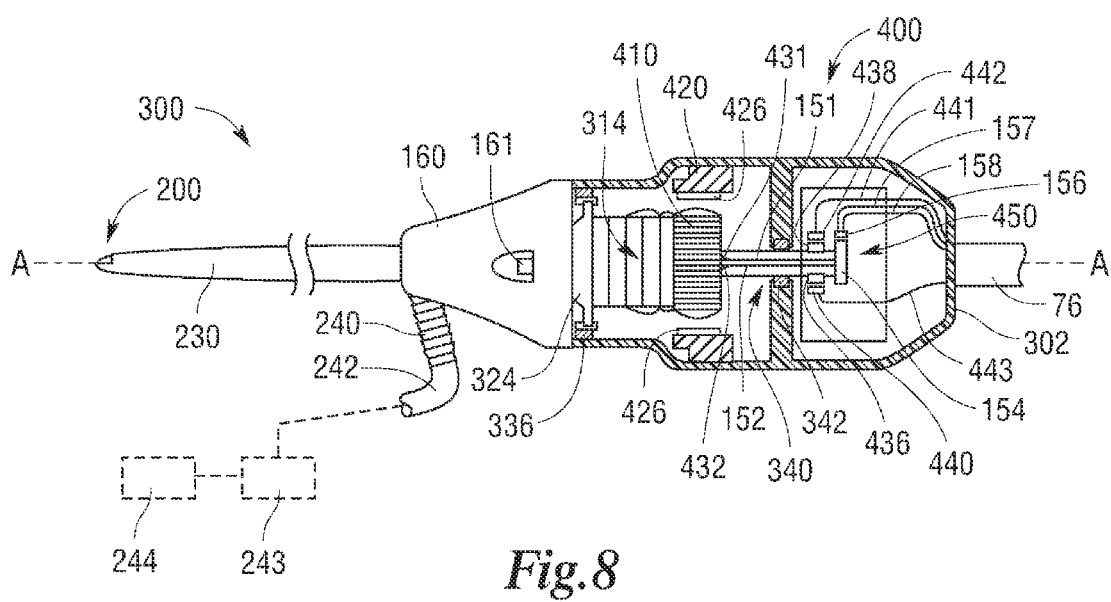
FIG. 8 is a partial cross-sectional view of another non-limiting surgical instrument handpiece embodiment.

FIG. 8 illustrates another surgical instrument 400 wherein like numbers previously used to describe the various embodiments discussed above are used to designate like components. In these embodiments, the surgical instrument 400 includes a housing 302 that houses an ultrasonic transducer assembly 314 that is attached to an ultrasonic horn 324. The ultrasonic horn 324 may be coupled to the proximal end 201 of the blade 200 in the manner described above. The ultrasonic horn 324 may be rotatably supported within the housing 302 by a distal bearing 336. A nosepiece 160 may be attached to the housing 302 in the manner described above.

In this embodiment, a brushed motor 410 is integrally attached to the ultrasonic transducer assembly 314. As used herein "integrally attached" means directly attached to or otherwise formed with the ultrasonic transducer assembly 314 for travel therewith. The term "integrally attached" as used with reference to the attachment of the brushed motor 410 to the ultrasonic transducer assembly 314 does not encompass those configurations wherein the ultrasonic transducer assembly is attached to the motor via a driven shaft arrangement. Also in this embodiment, magnets 426 are provided in a stator ring 420 that is fixed within the housing 302. Conductors 432, 434 extend through a hollow shaft 340 that is attached to the brushed motor 410. The hollow shaft 340 is rotatably supported within the housing 302 by proximal bearing 342. The motor conductor 432 is attached to a first inner motor contact 436 and the motor conductor 434 is attached to a second inner motor contact 438. The first and second inner motor contacts 436, 438 are supported on the portion of the hollow shaft 340 that extends into a slip ring assembly, generally designated as 450. The slip ring assembly 450 is fixed (i.e., non-rotatable) within the housing 302 and includes a first outer motor contact 440 that is coupled to conductor 441 and a second outer motor contact 442 that is coupled to conductor 443. The conductors 441, 443 form motor cable 74 as was described above. When the clinician desires to apply gross rotational motion to the ultrasonic transducer assembly 314 and ultimately to the blade 200, the clinician causes power to be supplied to the brushed motor 410 from the motor drive 26.

Also in this embodiment, conductors 151, 152 are attached to the ultrasonic transducer assembly 314 and extend through the hollow shaft 340 to be coupled to inner transducer contact 154 that is attached to the hollow shaft 340. The slip ring assembly 450 includes a fixed outer transducer contact 156 that is coupled to conductors 157, 158 that form generator cable 14 as was described above. When power is supplied to the brushed motor 410, the motor 410, ultrasonic transducer assembly 314, and motor shaft 340 are caused to rotate about axis A-A. Ultrasonic signals from the ultrasonic generator 12 are transferred to the inner contact 154 by virtue of rotational sliding contact or electrical communication between the inner contact 154 and the outer contact 156. Those signals are transmitted to the ultrasonic transducer assembly 314 by conductors 151, 152. The surgical instrument 400 may include a control arrangement of the type described above and be used in the various modes described above. It will be understood that the instrument 400 may be used in rotation mode, ultrasonic mode, rotation and ultrasonic mode ("duel mode") or coagulation mode as described above. A suction may be applied between the blade 200 and outer sheath 230 through port 240. A collection receptacle 243 and source of suction 240 may be attached to the port 240 by tube 242. The distal end of the blade is exposed through a window in the distal end of the outer sheath 230 to expose the blade to tissue as will be further discussed below.

FIGS. 9-13 illustrate another surgical instrument 500 wherein like numbers previously used to describe the various embodiments discussed above are used to designate like components. In these embodiments, the surgical instrument 500 includes a housing 302 that houses a transducer assembly 530 that is attached to an ultrasonic horn 324. The ultrasonic horn 324 may be coupled to the proximal end 201 of the blade 200 in the manner described above. The ultrasonic horn 324 may be rotatably supported within the housing 302 by a distal bearing 336. A nosepiece 160 may be attached to the housing 302 in the manner described above.

This embodiment includes a motor 510 that may comprise a stepper motor of the type and construction described above and may have an encoder portion associated therewith that communicates with the control module 24 as was described above. The motor 510 may receive power from the motor drive 26 through conductors 511, 512 that comprise motor cable 74 that extends through the common sheath 76. The motor 510 has a hollow motor shaft 520 attached thereto that extends through a slip ring assembly 150. The hollow drive shaft 520 is rotatably supported within the housing 302 by a proximal bearing 342. The slip ring assembly 150 is fixed (i.e., non-rotatable) within the housing 302 and includes a fixed outer contact 156 that is coupled to conductors 157, 158 that form generator cable 14 as was described above. An inner contact 154 is mounted on the hollow drive shaft 520 and is in electrical contact or communication with outer contact 156. Conductors 151, 152 are attached to the inner contact 154 and extend through the hollow drive shaft 520 to be coupled to the ultrasonic transducer assembly 530.

Figure 9:
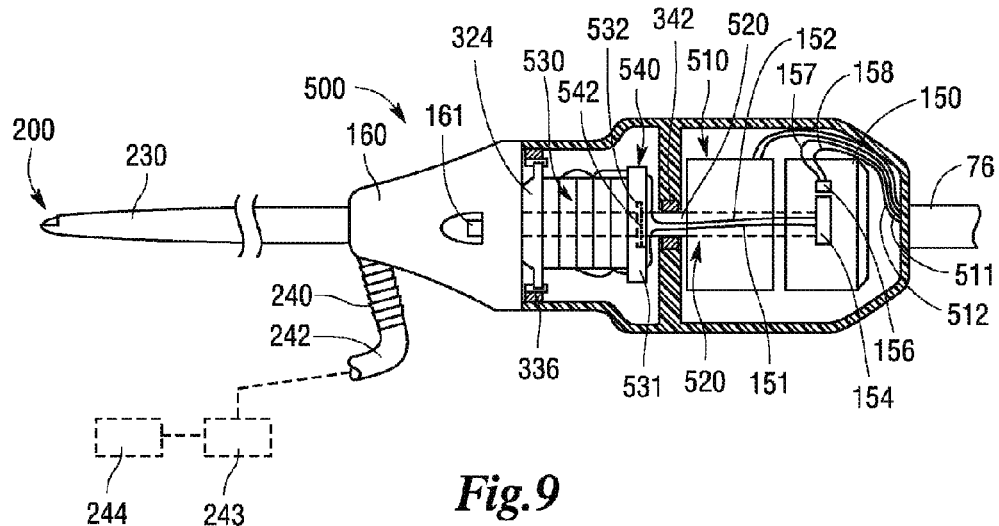
FIG. 9 is a partial cross-sectional view of another non-limiting surgical instrument handpiece embodiment.
Figure 10:
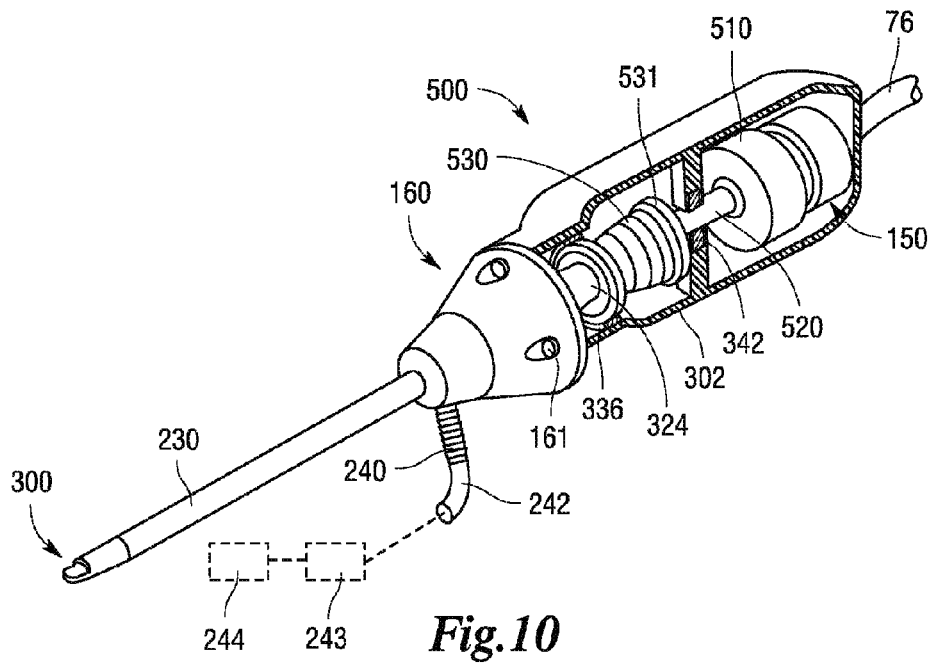
FIG. 10 is a perspective view of the surgical instrument handpiece embodiment depicted in FIG. 9.

In various embodiments, to facilitate ease of assembly and also to acoustically isolate the motor from the ultrasonic transducer assembly 530, the hollow drive shaft 520 may be detachably coupled to the ultrasonic transducer stack 530 by a coupling assembly, generally designated as 540. As can be seen in FIGS. 9, 11, and 12, the coupling assembly 540 may include a thin plate member 542 that is attached to a distal end 521 of the hollow drive shaft 520. The thin plate member 542 may be fabricated from a material that has a relatively low stiffness in the axial direction and a high stiffness in rotation. See FIG. 12. For example, the thin plate member 542 may be fabricated from 0.008 inch thick Aluminum 7075-T651 and be attached to the distal end 521 of the hollow drive shaft 520 by, for example, by a press fit or brazing. The coupling assembly 540 may further include a proximal end mass or flange portion 531 of the ultrasonic transducer assembly 530. The proximal end mass 531 may comprise, for example, a flange manufactured from stainless steel which is attached to the ultrasonic transducer assembly 530 by, for example, a bolted or other connection. As can be seen in FIG. 11, the end mass 531 has a hole 532 sized to receive the thin plate member 542 therein. In various embodiments, the thin plate member 542 may be sized to be pressed into the hole 532 such that rotation of the thin plate member 542 about axis A-A will cause the ultrasonic transducer assembly 530 to rotate about axis A-A. In other embodiments, a separate fastener plate (not shown) or snap rings (not shown) or snap features (not shown) may be provided to retain the thin plate member 542 in non-rotatable engagement with the end mass 531 of the ultrasonic transducer assembly 530. Such arrangements serve to minimize the transmission of acoustic vibrations to the motor from the ultrasonic transducer assembly.

FIGS. 14 and 15 illustrate an alternative thin plate member 542' that may be employed. In this embodiment, the thin plate member 542' has a plurality of radial notches 544 provided therein to form radial tabs 546. The hole 532 would be formed with notches (not shown) to accommodate the radial tabs 546 therein. Such arrangement may reduce the moment force applied to the shaft 520. By employing the thin plate members 542, 542' the amount of acoustic vibrations that are transferred from the ultrasonic transducer assembly 530 to the drive shaft 520 may be minimized.

When power is supplied to the motor 510, the drive shaft 520 rotates bout axis A-A which also causes the transducer assembly 530 to rotate about axis A-A. When the clinician desires to power the ultrasonic transducer assembly 530, power is supplied form the ultrasonic generator 12 to the fixed contact 156 in the slip ring assembly 150. Power is transmitted to the ultrasonic transducer assembly 530 by virtue of rotational sliding contact or electrical communication between the inner contact 154 and the outer contact 156. Those signals are transmitted to the ultrasonic transducer assembly 530 by conductors 151, 152. The surgical instrument 500 may include a control arrangement of the type described above and be used in the various modes described above. It will be understood that the instrument 400 may be used in rotation mode, ultrasonic mode, rotation and ultrasonic mode ("duel mode") or coagulation mode as described above. A suction may be applied between the blade 200 and outer sheath 230 through port 240. A collection receptacle 243 and source of suction 240 may be attached to the port 240 by tube 242. The distal end of the blade is exposed through a window in the distal end of the outer sheath 230 to expose the blade to tissue as will be further discussed below.

Figure 16:
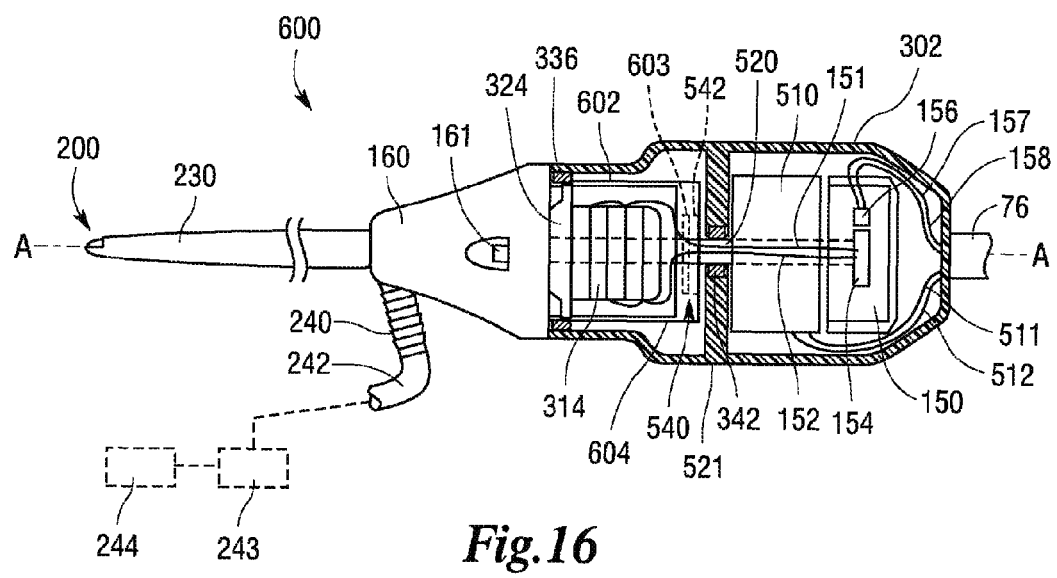
FIG. 16 is a partial cross-sectional view of another non-limiting surgical instrument handpiece embodiment.

FIG. 16 illustrates another surgical instrument 600 wherein like numbers previously used to describe the various embodiments discussed above are used to designate like components. In these embodiments, the surgical instrument 600 includes a housing 302 that houses a transducer assembly 314 that is attached to an ultrasonic horn 324. In this embodiment, the transducer assembly 314 and the ultrasonic horn 324 are attached to a PZT housing 602 that is rotatably supported within the housing 302 by a distal bearing 336. The ultrasonic horn 324 may be coupled to the proximal end of the blade 200 in the manner described above. A nosepiece 160 may be attached to the housing 302 by fasteners 161 in the manner described above.

This embodiment includes a motor 510 that may comprise a stepper motor of the type and construction described above. The motor 510 may have an encoder associated therewith that communicates with the control module 24 (FIG. 1) as was described above. The motor 510 may receive power from the motor drive 26 (FIG. 1) through conductors 511, 512 that comprise motor cable 74 that extends through the common sheath 76. The motor 510 has a hollow motor shaft 520 attached thereto that extends through a slip ring assembly 150. The hollow drive shaft 520 is rotatably supported within the housing 302 by a proximal bearing 342.

The slip ring assembly 150 is fixed (i.e., non-rotatable) within the housing 302 and includes a fixed outer contact 156 that is coupled to conductors 157, 158 that form generator cable 14 as was described above. An inner contact 154 is mounted on the rotatable hollow drive shaft 520 and is in electrical contact or communication with outer contact 156. Conductors 151, 152 are attached to the inner contact 154 and extend through the hollow drive shaft 520 to be coupled to the ultrasonic transducer assembly 314. In various embodiments, to facilitate ease of assembly and also acoustically isolate the motor 510 from the ultrasonic transducer assembly 314, the hollow drive shaft 520 may be detachably coupled to the PZT housing 602 by a coupling assembly, generally designated as 540. The coupling assembly 540 may include a thin plate member 542 that is attached to a distal end 521 of the hollow drive shaft 520. As discussed above, the thin plate member 542 may be fabricated from a material that has a relatively low stiffness in the axial direction and a high stiffness in rotation. The PZT housing 602 has a proximal end portion 604 that has a hole 603 sized to receive the thin plate member 542 therein. In various embodiments, the thin plate member 542 may be sized to be pressed into the hole 603 such that rotation of the thin plate member 542 about axis A-A will cause the PZT housing 602 and ultrasonic transducer assembly 314 and ultrasonic horn 324 to rotate about axis A-A. In other embodiments, a separate fastener plate (not shown) or snap rings (not shown) or snap features (not shown) may be provided to retain the thin plate member 542 in non-rotatable engagement with the proximal end portion 604 of the PZT housing 602. This embodiment could also employ the thin plate member 542' as was discussed above.

When power is supplied to the motor 510, the drive shaft 520 rotates about axis A-A which also causes the PZT housing 602 and ultrasonic transducer assembly 314 to rotate about axis A-A. When the clinician desires to power the ultrasonic transducer assembly 314, power is supplied from the ultrasonic generator 12 to the fixed contact 156 in the slip ring assembly 150. Power is transmitted to the ultrasonic transducer assembly 314 by virtue of rotational sliding contact or electrical communication between the inner contact 154 and the outer contact 156. Those signals are transmitted to the ultrasonic transducer assembly 314 by conductors 151, 152. The surgical instrument 500 may include a control arrangement of the type described above and be used in the various modes described above. It will be understood that the instrument 400 may be used in rotation mode, ultrasonic mode, rotation and ultrasonic mode ("duel mode") or coagulation mode as described above. A suction may be applied between the blade 200 and outer sheath 230 through port 240. A collection receptacle 243 and source of suction 240 may be attached to the port 240 by tube 242. The distal end of the blade is exposed through a window in the distal end of the outer sheath 230 to expose the blade to tissue as will be further discussed below.

In an effort to reduce the overall size of the housing 302 employed in each of the instruments 300, 400, 500, and 600, the ultrasonic transducer assemblies employed in each of those respective instruments could be replaced with a half wave transducer that is physically shorter in length.

Ultrasonic Blade and Sheath Embodiments

Current arthroscopic tools include punches, reciprocating shavers, and radio frequency (RF) powered devices. Mechanical devices such as punches and shavers tend to create minimal tissue damage, but can sometimes leave behind ragged cut lines which are not desirable. RF powered blades can leave behind smoother cut lines and also ablate large volumes of soft tissue. However, such devices can create more tissue damage than pure mechanical instruments. The various non-limiting surgical instruments embodiments described above provide a host of advantages over conventional RF powered surgical instruments as well as conventional mechanical shavers that employ a rotating tissue cutting member. As will be discussed in further detail below, additional advantages may be realized by employing the unique and novel blade and sheath configurations of various non-limiting embodiments.

Figure 19:
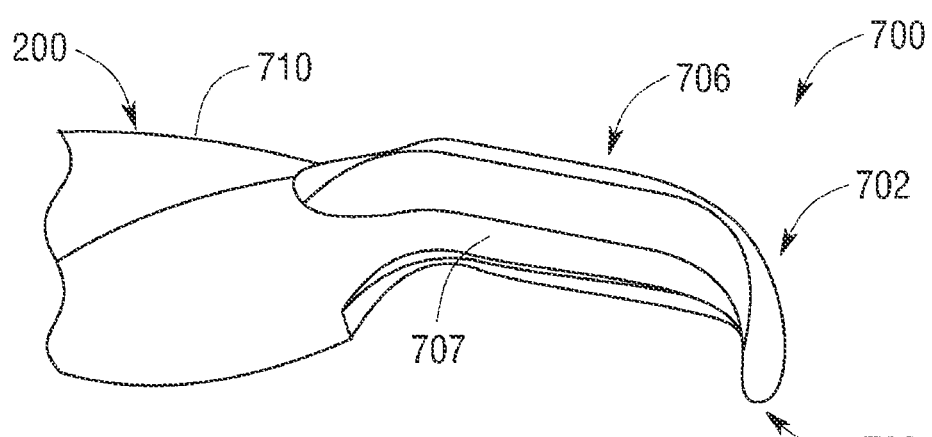
FIG. 19 is a partial bottom perspective view of the blade of FIGS. 17 and 18.
Figure 20:
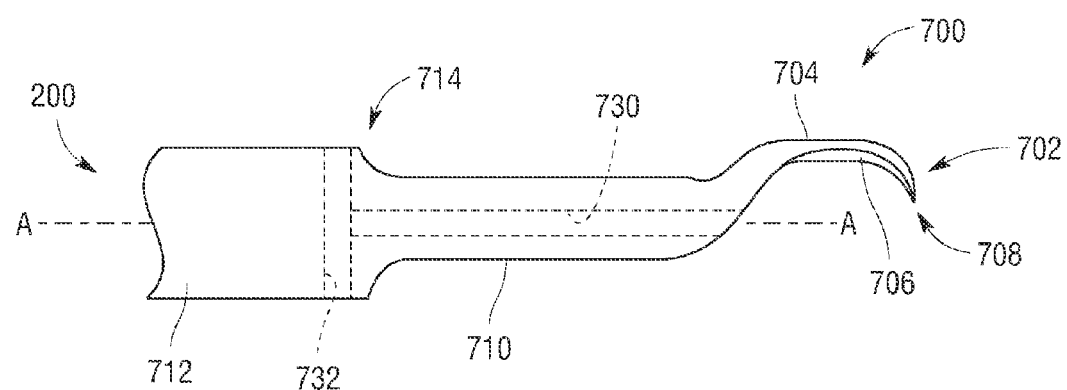
FIG. 20 is a side view of a portion of another non-limiting blade embodiment.

FIGS. 17-21 illustrate one form of blade 200 and outer sheath 230 that may be employed in connection with the various surgical instruments described above. As can be seen in those Figures, the blade 200 may have a distal end portion 700 and the outer sheath 230 may have a distal end portion 720. The blade 200 may be fabricated from, for example, titanium and the outer sheath 230 may be fabricated from, for example, Poly ether ether ketone ("PEEK"), Ultem®, or stainless steel. As was discussed above, the blade 200 may have a waveguide or proximal end portion that is configured to be threadably or otherwise attached to an ultrasonic horn 324 (FIGS. 6-10 and 16) in a known manner. The distal end portion 700 of the blade 200 may have a curved tip portion 702 formed thereon. The curved tip 702 may have an arcuate top segment 704 that has a cutting edge 706 formed on each lateral side 705. The cutting edges 706 may terminate distally in a common, substantially pointed distal end 708. The pointed distal end 708 may be relatively blunted or the pointed distal end 708 may have a relatively sharpened point. As can be seen in FIG. 20, the pointed distal end 708 may curve inwardly to about the central axis A-A of the blade. As can be seen in FIG. 19, in various embodiments, the cutting edges 706 may not intersect each other but may be separated by a center portion 707. As can be seen in FIG. 20, the blade 200 may have a reduced neck portion 710 that protrudes distally from a waveguide or proximal blade portion 712. A node 714 may be established at the area where the neck portion 710 protrudes from the proximal portion 712.

Figure 17:
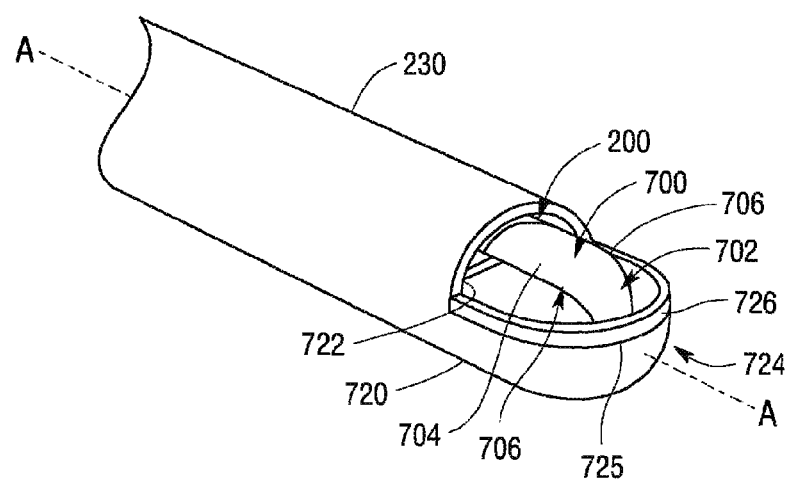
FIG. 17 is a partial perspective view of a non-limiting outer sheath and blade embodiment.
Figure 18:
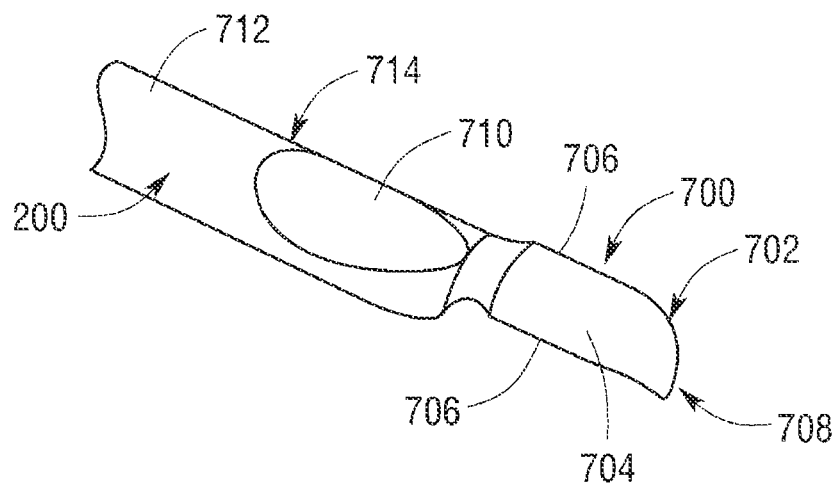
FIG. 18 is a partial perspective view of the non-limiting blade embodiment depicted in FIG. 17.

As can be seen in FIG. 17, the outer sheath 230 also has a distal end portion 720 that has a window or opening 722 formed therein to expose the distal end portion 700 of the blade 200. As can be further seen in FIG. 17, the outer sheath 230 may comprise a hollow cylinder that has a substantially blunted end 724. In various embodiments, the window 722 extends for one half of the circular cross-section of the sheath 230. Such window configuration forms an arcuate ledge 725 that extends around the blunted end 724. In various embodiments, the outer sheath 230 may be fabricated from, for example, Poly ether ether ketone ("PEEK"), Ultem®, or stainless steel. To prevent metal-to-metal contact between the cutting edges 706 on the distal end portion 700 of the blade 200 and the ledge 725, a polymer fender 726 may be attached by, for example, adhesive or a T-slot around the ledge 724. See FIG. 17. Fender 726 may be fabricated from, for example, Teflon®, silicone or other reduced or "low friction" material. The fender 726 may be sized to produce an interference fit of, for example, 0.005 inches with the cutting edges 706 and the pointed distal end 708.

In use, as the blade 200 is rotated about axis A-A within the outer sheath 230 and introduced to tissue, the tissue is drawn into the window 722 by means of the suction applied between the inner sheath 220 (FIG. 4), and the outer sheath 230 as was described above. The tissue drawn into the window 722 is then cut as the cutting edges 706 are rotated past the fender 726 and the cut tissue may pass between the inner sheath 220 and outer sheath 230 and out through the suction port 240 (FIGS. 4, 6-10, and 16) to the collection receptacle 243 (FIGS. 4, 6-10, and 16).

Figure 21:
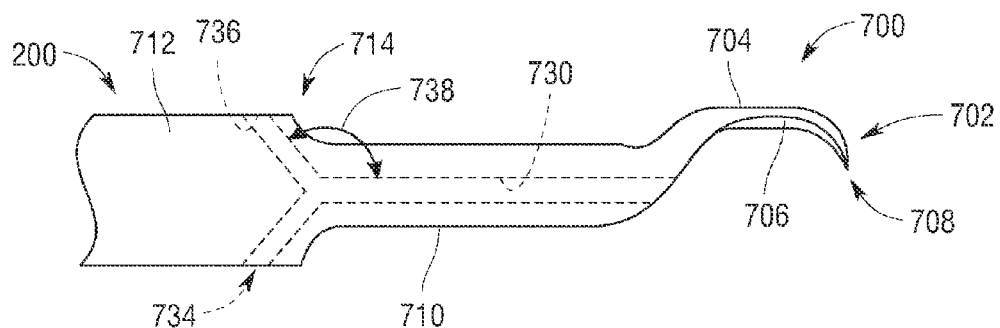
FIG. 21 is a side view of a portion of another non-limiting blade embodiment.

In another embodiment, an axial suction passage 730 may be provided through the neck portion 710 of the blade 200. See FIG. 20. The axial suction passage 730 may communicate with a transverse suction passage 732 in the area of node 714. Thus, the cut tissue may pass through the passages 730, 732 and out between the inner sheath 220 and outer sheath 230 and out through the suction port 240 (FIGS. 4, 6-10, and 16) to the collection receptacle 243 (FIGS. 4, 6-10, and 16). FIG. 21 depicts an alternative embodiment wherein two exit passages 734, 736 communicate with the axial passage 730 and extend at an angle therefrom. In various embodiments, the exit passages 734, 736 may extend from the axial passage 730 at an angle 738 of, for example, forty-five (45) degrees. Such arrangement may serve to reduce impedance and power losses during ultrasonic activation which might have otherwise resulted from water being drawn in through the window 722 in the outer sheath 230.

In use, the clinician may elect to rotate the blade 200 within the outer sheath 230 without applying ultrasonic motion thereto. The clinician may also elect to apply ultrasonic motion to the rotating blade or the clinician may wish apply ultrasonic motion to a parked (non-rotating) blade to use the portion of the blade exposed in the window 722 to coagulate tissue.

Figure 22:
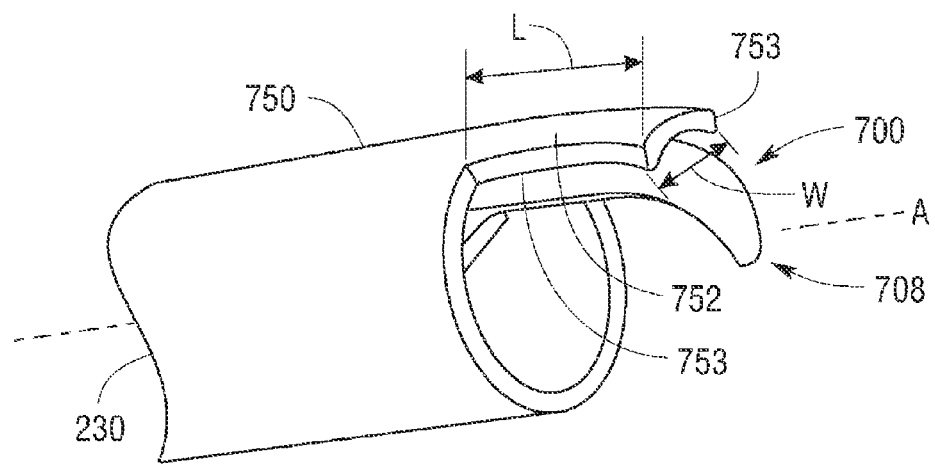
FIG. 22 is a partial perspective view of a distal end of another non-limiting outer sheath and blade arrangement.

FIG. 22 illustrates use of blade 200 in connection with an outer sheath 230 that has a distal end portion 750 that includes a distally protruding nose segment 752. In various embodiments, the nose segment 752 may have an arcuate width "W" that comprises approximately ten (10) to thirty (30) percent of the circumference of the distal end portion 750 of the outer sheath 230. The nose segment 752 may protrude distally from the end of the distal end portion 750 of the sheath 230 a length "L" that may be approximately 0.25 inches, for example. In alternative embodiments, a low friction fender or guard (not shown) may be applied to the sides 753 of the nose segment 752 if desired. These embodiments may operate in a similar manner to the previous embodiment. However, this embodiment has the added ability to cut tissue with the exposed tip. As with the other embodiments, the clinician may apply gross rotational motion to the blade 200 without ultrasonic motion or with ultrasonic motion. In another alternative method of use, the exposed tip 708 and partially exposed cutting edges 706 may be used to cut tissue when the blade is not being rotated or vibrated.

Figure 23:
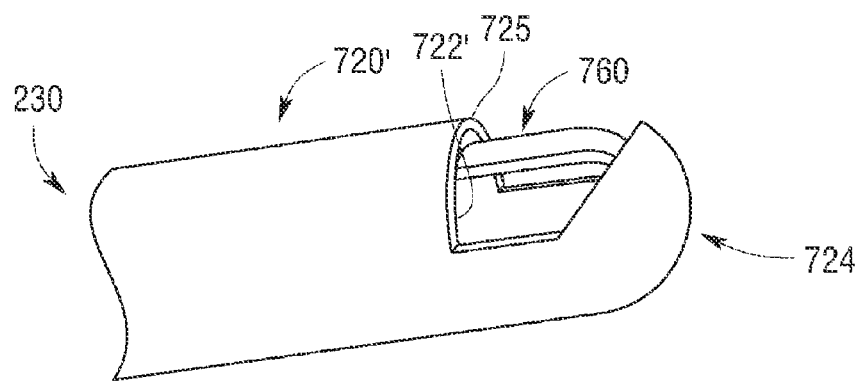
FIG. 23 is a partial perspective view of a distal end of another non-limiting outer sheath and blade arrangement.
Figure 23A:
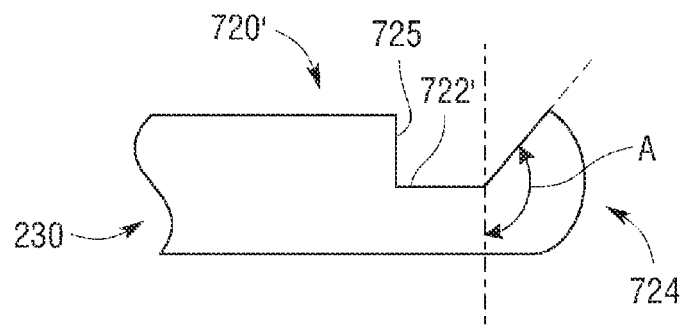
FIG. 23A is a side view of a portion of the non-limiting outer sheath embodiment depicted in FIG. 23.
Figure 24:
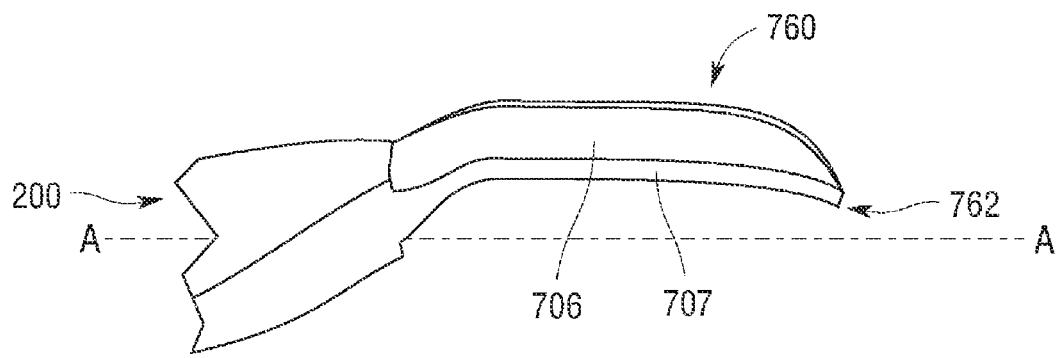
FIG. 24 is a side view of a portion of another non-limiting blade embodiment.

FIGS. 23-24 illustrate another non-limiting blade and outer sheath embodiment. In this embodiment, the blade 200 has a distal end portion 760 that is substantially similar to the distal end portion 700 of the blade configuration described above. However, the distal blade portion 760 does not hook inwardly to the same degree such that the blade tip 762 does not intersect the central axis A-A. See FIG. 24. As can be seen in FIG. 23, the window 722' in the distal end portion 720 of the outer sheath 230 does not extend the entire distance from an end wall 725 to the blunt tip 724. Thus, in this embodiment, the blunt tip 724 comprises a nose that extends more than 90° but less than 180° (i.e., angle "A" in FIG. 23A is greater than 90° but less than 180°).

Figure 25:
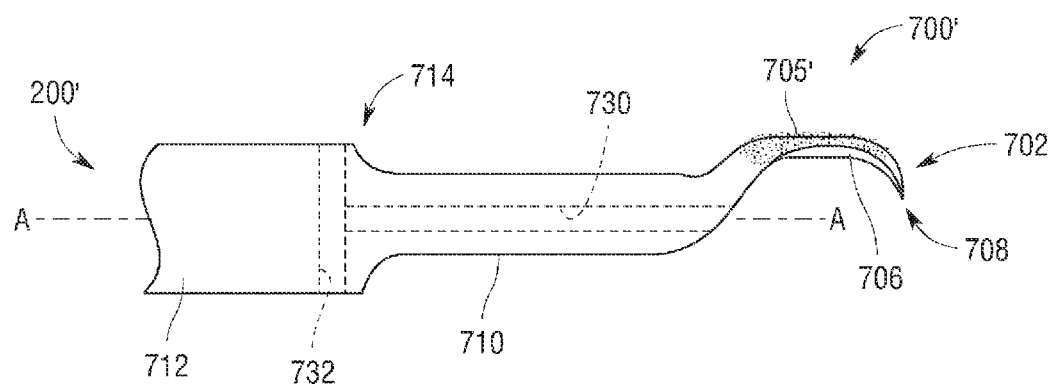
FIG. 25 is a side view of a portion of another non-limiting blade embodiment.
Figure 26:
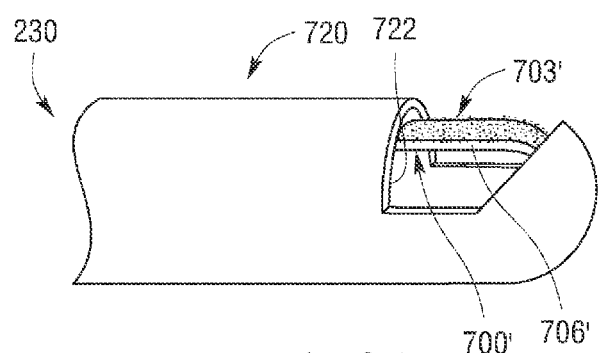
FIG. 26 is a partial perspective view the non-limiting blade embodiment of FIG. 25 within a distal end of another non-limiting outer sheath embodiment.
Figure 27:
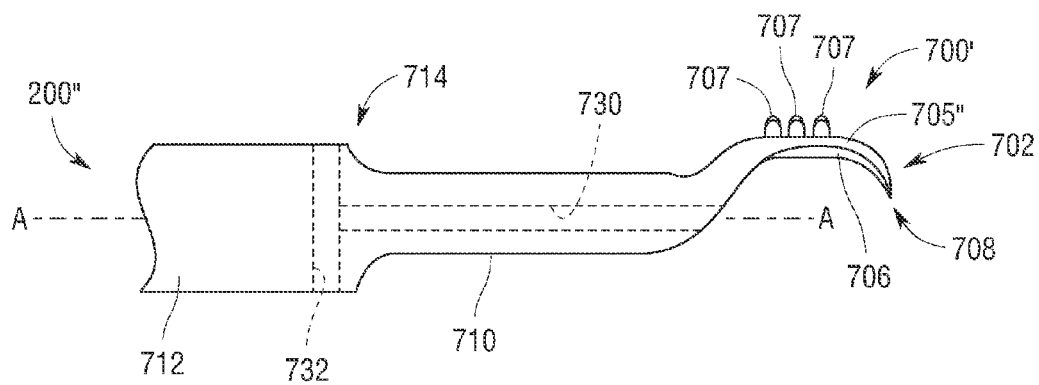
FIG. 27 is a side view of a portion of another non-limiting blade embodiment.
Figure 28:
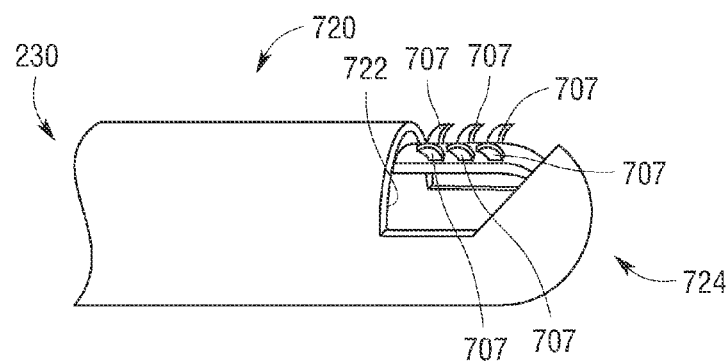
FIG. 28 is a partial perspective view the non-limiting blade embodiment of FIG. 27 within a distal end of another non-limiting outer sheath embodiment.
Figure 29:
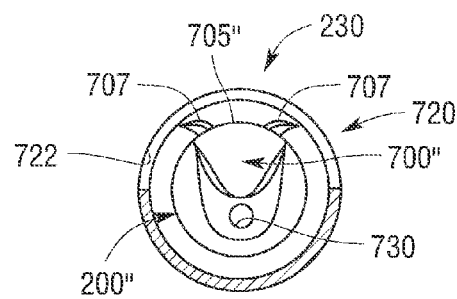
FIG. 29 is a partial cross-sectional end view of the non-limiting blade and outer sheath embodiments of FIG. 28.

FIGS. 25 and 26 depict another non-limiting blade embodiment. In this embodiment, the blade 200' may be substantially similar to blade 200 or any of the other blades described herein. In this embodiment, the distal end 700' has a roughened upper surface 705'. Such roughened surface 705' creates higher friction forces between the distal end portion 700' of the blade 200' and the tissue to draw the tissue into the window 722' in the distal end portion 720 of the outer sheath 230 (FIG. 26). By pulling more tissue into the window 722, the leading cutting edge 706' of the blade 200' may have a higher likelihood of cutting the tissue cleanly. In various embodiments, for example, the roughened surface may be formed by knurling or the upper surface may be coated with a hard material such as diamond or the like FIGS. 27-29 illustrate another non-limiting blade embodiment. In this embodiment, the blade 200" may be substantially similar to blade 200 described herein. In this embodiment, the distal end 700" has a series of radially extending cutting teeth 707 protruding outward from upper surface 705" for pulling and cutting tissue as the blade 200" is rotated within the outer sheath 230.

FIGS. 30, 31, and 32A-D illustrate another non-limiting blade and outer sheath embodiment. During use of various instruments that employ a rotatable blade within an outer sheath, it has been experienced that the tissue may get "kicked out" of the sheath window as the blade rotates therein. This can lead to reduced cutting speeds as tissue is not adequately captured and held between the cutting edges. The blade 800 of this embodiment addresses such potential shortcomings.

Figure 30:
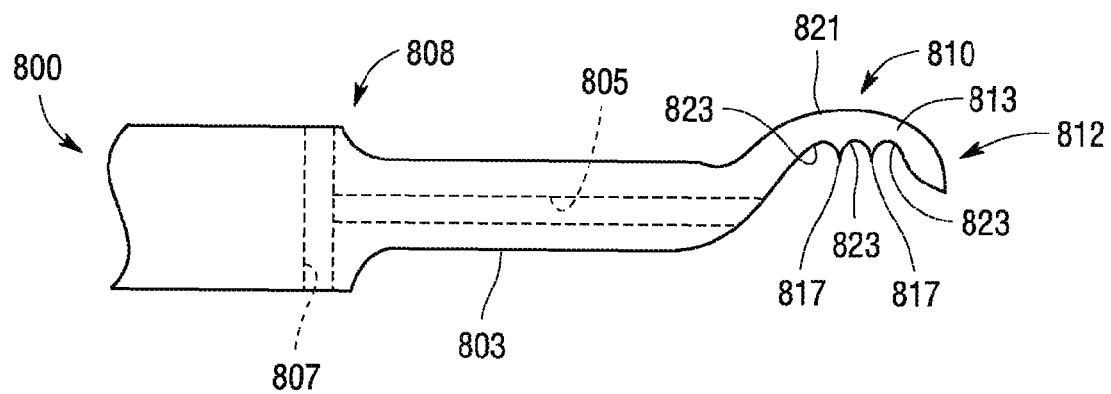
FIG. 30 is a side view of a portion of another non-limiting blade embodiment.
Figure 31:
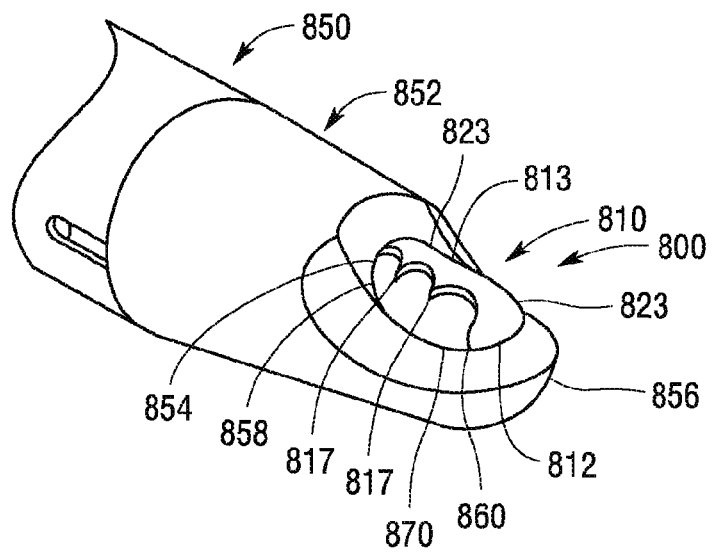
FIG. 31 is a partial perspective view of the non-limiting blade embodiment of FIG. 30 within a distal end of another non-limiting outer sheath embodiment.

As can be seen in FIG. 30, the blade 800 may be substantially the same as blade 200 except for the differences noted herein. In particular, the blade 800 may include a neck portion 803 that that terminates in a distal end portion 810. The distal end portion 810 may have a somewhat curved tip 812. A series of teeth 817 may be provided on at least one lateral side 813 or 815 of the distal end portion 810. In the embodiment depicted in FIGS. 32A-D, teeth 817 and 819 are formed on lateral sides 813, 815, respectively, of the distal end portion 810. The distal end portion 810 further has a somewhat domed top portion 821. In the embodiment shown in FIGS. 30-32D, the teeth 817 comprise relatively sharp points that define a series of arcuate openings 823 therebetween. Teeth 819 also comprise relatively sharp points that have a series of arcuate openings 825 therebetween. As shown in FIG. 30, an axial suction passage 805 may be provided through the neck portion 803 of the blade 800. The axial suction passage 805 may communicate with a transverse suction passage 807 in the area of node 808. Thus, the cut tissue may pass through the passages 805, 807 and out between the inner sheath (not shown) and outer sheath 850 and out through a suction port to a collection receptacle in the manner described hereinabove. Other suction path arrangements may also be successfully employed.

The outer sheath 850 may be substantially similar to the outer sheath 230 described above and have a distal sheath tip 852 attached thereto that has a window or opening 854 formed therein to expose the distal end portion 810 of the blade 800. See FIG. 31. The outer sheath 850 may comprise a hollow cylinder fabricated from for example, stainless steel. In various embodiments, the window 854 extends for approximately one half of the circular cross-section of the sheath 850 and forms a blade opening 858 therein. The distal sheath tip 852 may be fabricated from metal such as, for example, stainless steel such that a relatively sharp cutting edge 860 extends around the blade opening 858. For the purpose of explanation, the sharp cutting edge 860 has a first lateral cutting edge portion 862 and a second lateral cutting edge portion 864.

Figure 32A:
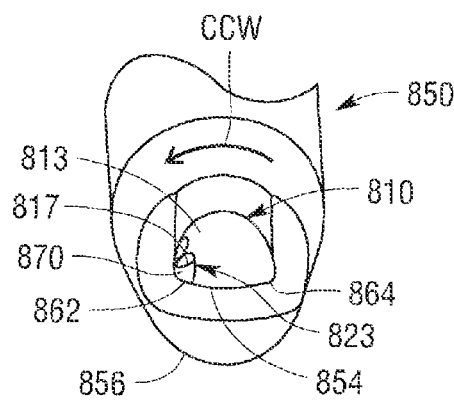
FIG. 32A illustrates a first rotational position of the non-limiting blade embodiment of FIGS. 30 and 31 within the outer sheath embodiment of FIG. 31.
Figure 32B:
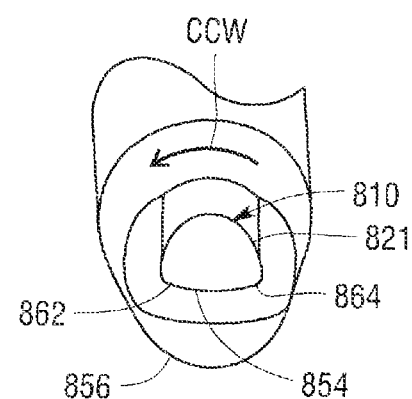
FIG. 32B illustrates a second rotational position of the non-limiting blade embodiment of FIGS. 30 and 31 within the outer sheath embodiment of FIG. 31.
Figure 32C:
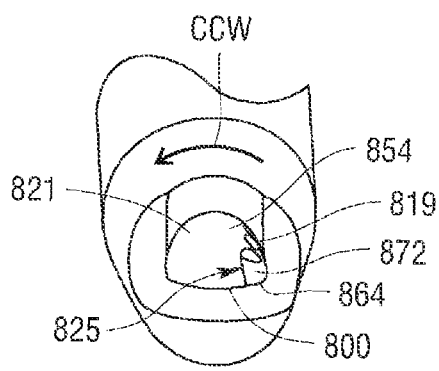
FIG. 32C illustrates a third rotational position of the blade embodiment of FIGS. 30 and 31 within the outer sheath embodiment of FIG. 31.
Figure 32D:
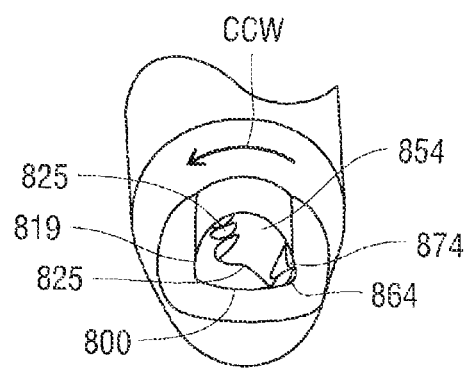
FIG. 32D illustrates a fourth rotational position of the blade embodiment of FIGS. 30 and 31 within the outer sheath embodiment of FIG. 31.

FIGS. 32A-D illustrate a sequential rotation of the blade 800 within the outer sheath 850. Turning to FIG. 32A first, the blade 800 is shown being rotated in a counter clockwise "CCW" direction. As shown in that Figure, the cutting teeth 817 on the first lateral side 813 of the blade 800 are positioned to shear tissue (not shown) between the teeth 817 and the first lateral cutting edge portion 862 of the cutting edge 860. When in that position, the arcuate openings 823 between the teeth 817 are exposed to collectively form a first lateral suction path 870 between the blade 800 and the distal sheath tip 852 to enable the tissue to be drawn therein by the suction being applied through the suction passage 805 (FIG. 30). As the rotational sequence continues, the domed upper portion 821 of the blade 800 covers the opening 854 in the distal sheath tip 852 such that there are no exposed suction paths for tissue to enter into the opening 854. As the blade continues through its rotation, FIG. 32C illustrates that the arcuate openings 825 between teeth 819 collectively form a second lateral suction path 872 between the second lateral cutting edge portion 864 and the blade 800 to enable tissue to be drawn therein. As the blade 800 continues to rotate in the CCW direction, a third suction path 874 is exposed to enable tissue to be further drawn into opening 854. Thus, such arrangement permits a sequential opening of suction paths from one lateral side of the blade opening 858 to the other to facilitate better tissue cutting. In use, the clinician may elect to rotate the blade 800 within the outer sheath 850 without applying ultrasonic motion thereto. The clinician may also elect to apply ultrasonic motion to the rotating blade or the clinician may wish apply ultrasonic motion to a parked (non-rotating) blade to use the portion of the blade exposed in the opening 854 to coagulate tissue.

Figure 33:
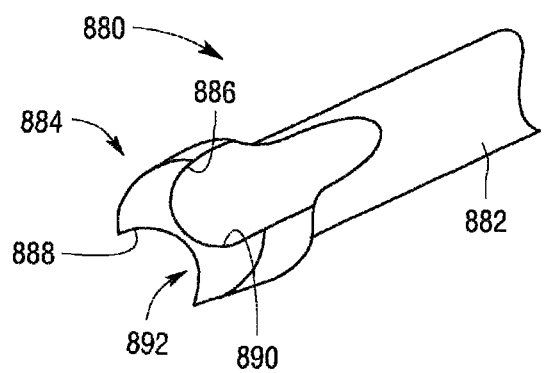
FIG. 33 is a perspective view of a portion of another non-limiting blade embodiment.
Figure 34:
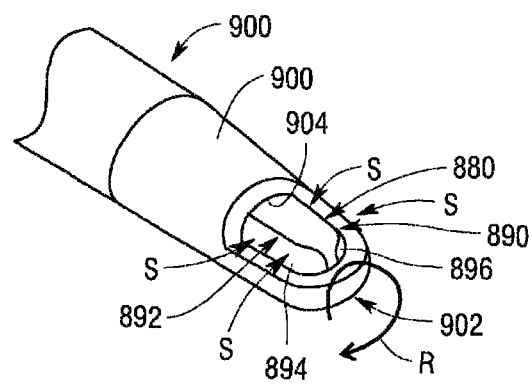
FIG. 34 is a partial perspective view of the blade embodiment of FIG. 33 within a non-limiting outer sheath embodiment.

FIGS. 33 and 34 illustrate another blade embodiment 880 that may be substantially the same as blade 200 except for the differences noted below. In particular, the blade 880 may include a waveguide or proximal portion 882 that that terminates in a distal tissue cutting portion 884. The proximal portion 882 of the blade 880 may be configured to be threadably or otherwise attached to an ultrasonic horn of any of the various embodiments discussed above. The distal tissue cutting portion 884 may have opposed arcuate channels 886, 888 formed therein. The first arcuate channel 886 may define a first cutting edge 890 and the second arcuate channel 888 may define a second cutting edge 892. This blade embodiment may be used in connection with any of the outer sheath configurations described above. In the depicted embodiment, hollow outer sheath 900 is employed which may be similar to sheath 230 for example and include a distal sheath tip 901 that has rounded or blunted nose portion 902 and a window 904. The hollow outer sheath 900 may be fabricated from, for example, stainless steel and the distal sheath tip 901 may be fabricated from metal such as, for example, stainless steel. The window 904 forms an arcuate cutting edge 906 that cooperates with the cutting edges 890, 892 on the blade 880 to shear off tissue as the blade 880 is rotated within the outer sheath 900 in the various manners described above. In at least one embodiment, the proximal portion 882 of blade 880 may be sized relative to the hollow outer sheath 900 such that a clearance is provided therebetween to enable a suction to be applied thereto in the manner described above, for example.

Figure 34A:
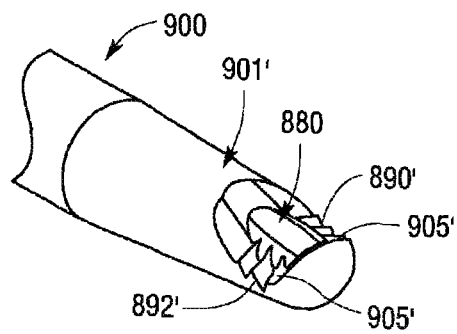
FIG. 34A is a partial perspective view of another non-limiting blade and outer sheath embodiment.

As can be seen in FIG. 34, as the blade 880 rotates (represented by arrow "R") the arcuate channels 886, 886 define openings 894, 896 between the distal end 884 of the blade 880 and the walls of the distal sheath tip 901 to enable tissue to be drawn therein by the suction (represented by arrows "S") applied to the area between the inner wall of the outer sheath 900 and the neck 882 of the blade 800. It will also be appreciated that the blade 880 may be rotated in a counter clockwise or clockwise direction or be selectively oscillated between such rotational directions and still effectively cut tissue drawn therein. FIG. 34A depicts an alternative sheath tip embodiment 901' that is fabricated from a metal material such as, for example, stainless steel that has a series of serrated cutting teeth 905' formed on each cutting edge 890', 892'.

Figure 35:
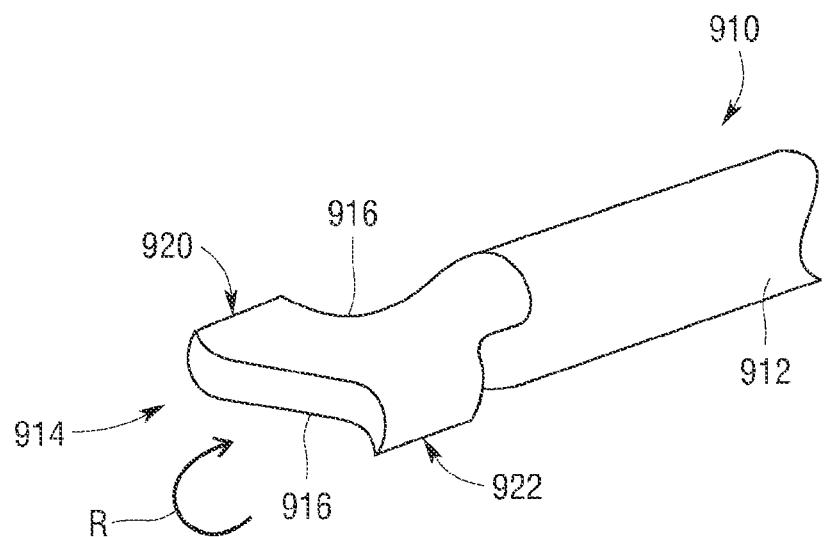
FIG. 35 is a perspective view of a portion of another non-limiting blade embodiment.

FIG. 35 depicts another blade embodiment 910 that may be substantially the same as blade 200 except for the differences noted below. In particular, the blade 910 may include a waveguide or proximal portion 912 that that terminates in a distal tissue cutting portion 914. The proximal portion 912 of the blade 910 may be configured to be threadably or otherwise attached to an ultrasonic horn of any of the various embodiments discussed above. The distal tissue cutting portion 914 may have opposed channels 916 formed therein that cooperate to define a first cutting edge 920 and a second cutting edge 922. This blade embodiment may be used in connection with any of the various outer sheath configurations described above and is designed to only rotate in a single direction "R" for tissue cutting purposes. As with the above-described embodiment, the arcuate channels 916 define openings between the tissue cutting portion 914 of the blade 910 and the inner walls of the distal sheath tip to enable tissue to be drawn therein as suction is applied to the area between the proximal portion 912 an the inner wall of the outer sheath.

Figure 36:
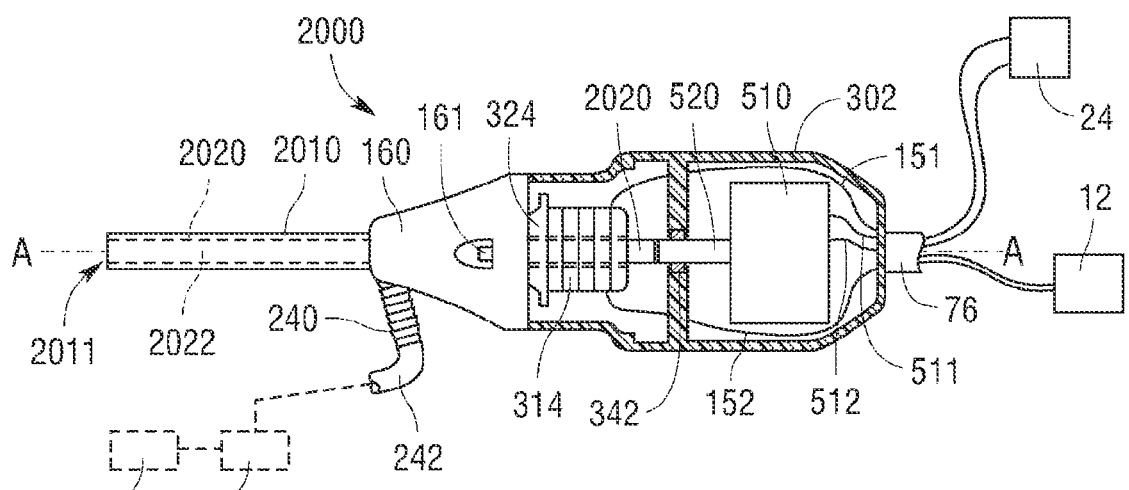
FIG. 36 is a partial cross-sectional view of another non-limiting ultrasonic surgical instrument embodiment.

FIG. 36 illustrates another surgical instrument 2000 wherein like numbers previously used to describe the various embodiments discussed above are used to designate like components. In these embodiments, the surgical instrument 2000 includes a housing 302 that houses an ultrasonic transducer assembly 314 that is attached to an ultrasonic horn 324. In this embodiment, the ultrasonic transducer assembly 314 and the ultrasonic horn 324 may be non-rotatably supported within the housing 302 in a known manner. Electrical control signals may be supplied to the ultrasonic transducer assembly 314 from an ultrasonic generator 12 by conductors 151, 152. Activation of the ultrasonic generator 12 will cause the ultrasonic transducer assembly 314 to apply ultrasonic motion to the ultrasonic horn 324. In this embodiment, a hollow outer sheath 2010 is coupled to the ultrasonic horn 324 for receiving ultrasonic motion therefrom. For example, in various embodiments, the outer sheath 2010 may be coupled to the ultrasonic horn 324 by a threaded connection or other suitable fastening arrangement.

This embodiment includes a rotatable blade 2020 that is rotatably supported within the outer sheath 2010 and is coupled to a motor 510 supported within the housing 302. The motor 510 may, for example, comprise a stepper motor of the type and construction described above. The motor 510 may have an encoder associated therewith that communicates with a control module 24 (FIG. 1) as was described above. The blade 2020 may have a hollow distal portion 2022 and a solid proximal portion 2024. See FIG. 36A. The solid proximal portion 2024 may be attached to the motor drive shaft 520 by a threaded or other suitable connection. The motor drive shaft 520 may be rotatably supported within the housing 302 by a proximal bearing 342. When control signals are supplied to the motor 510, the drive shaft 520 rotates about axis A-A which also causes the blade 2020 to rotate about axis A-A within the outer sheath 2010.

Figure 36A:
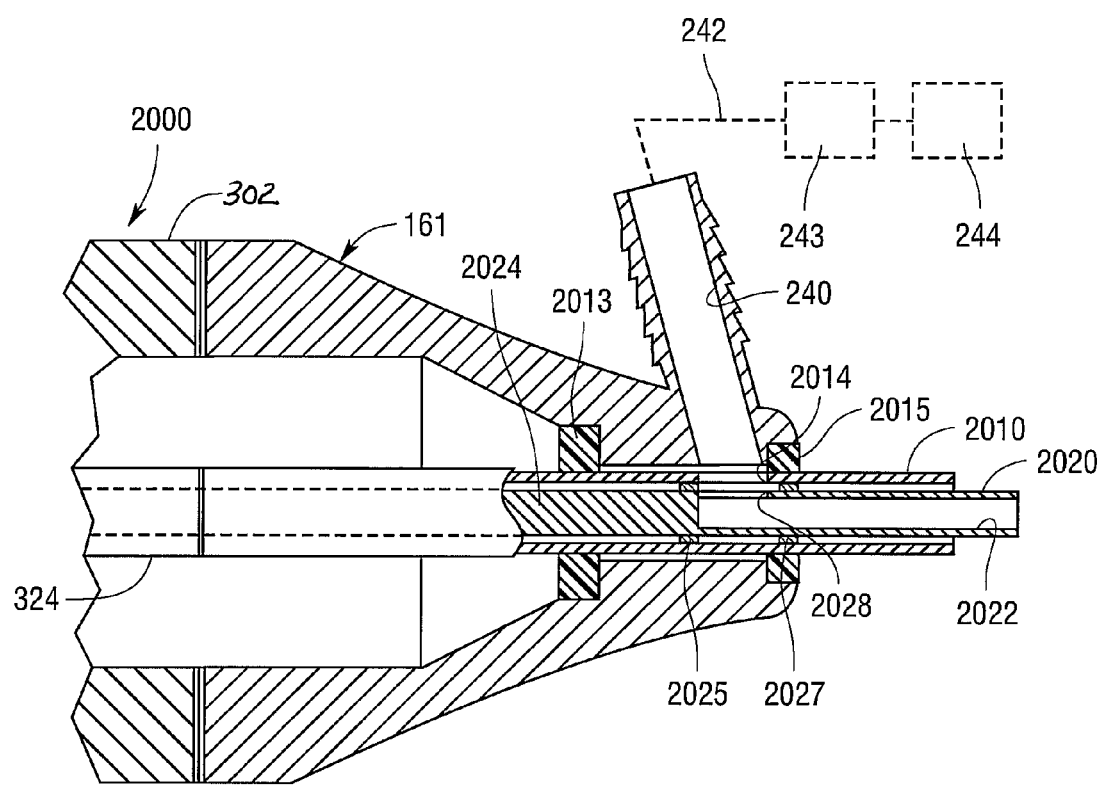
FIG. 36A is a partial cross-sectional view of a nosepiece portion of another non-limiting surgical instrument embodiment of the present invention.

As can be further seen in FIG. 36A, the hollow outer sheath 2010 is supported within a hollow nosepiece 160 that has a suction port 240 therein. A flexible tube 242 may be attached to the suction port 240 and communicate with a collection receptacle 243 that is coupled to a source of suction, generally depicted as 244. The hollow sheath 2010 may be supported within the nosepiece 160 by a proximal seal 2013 and a distal seal 2015 which are located on each side of the suction port 240 as shown in FIG. 36A and which serve to establish fluid tight seals therebetween. The hollow sheath 2010 is provided with at least one proximal sheath opening 2014 in registration with the suction port 240 between the proximal seal 2013 and the distal seal 2015. In addition, the hollow distal portion 2022 of the blade 2020 is rotatably supported within the hollow sheath 2010 by at least a proximal blade seal 2025 and a distal blade seal 2027. At least one blade discharge port 2028 may be provided through the hollow portion 2022 of the blade 2020 between the proximal blade seal 2025 and the distal blade seal 2027 to discharge into the at least one proximal sheath opening 2014.

Figure 37:
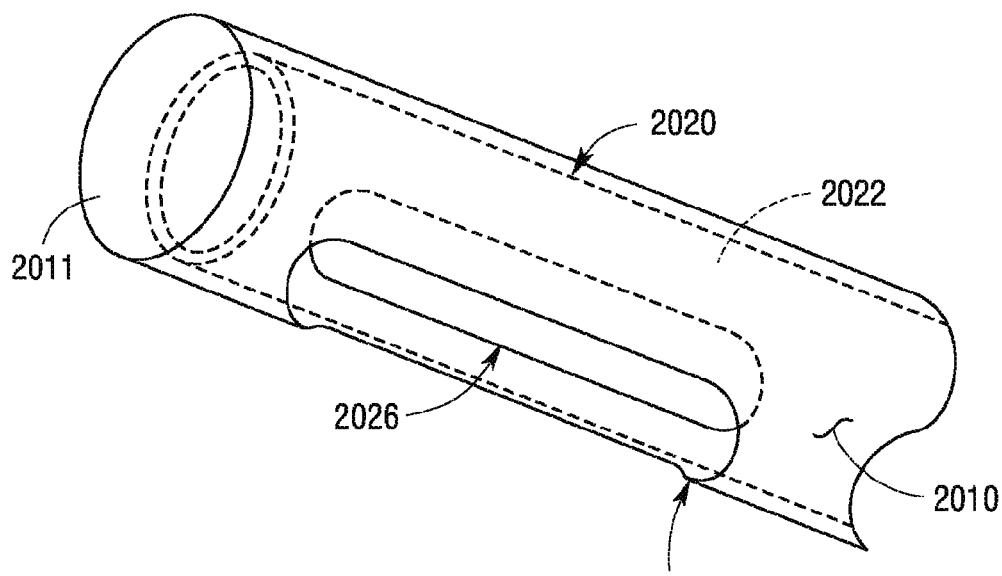
FIG. 37 is a partial perspective view of a distal end of the non-limiting outer sheath and blade arrangement of FIG. 36.
Figure 38:
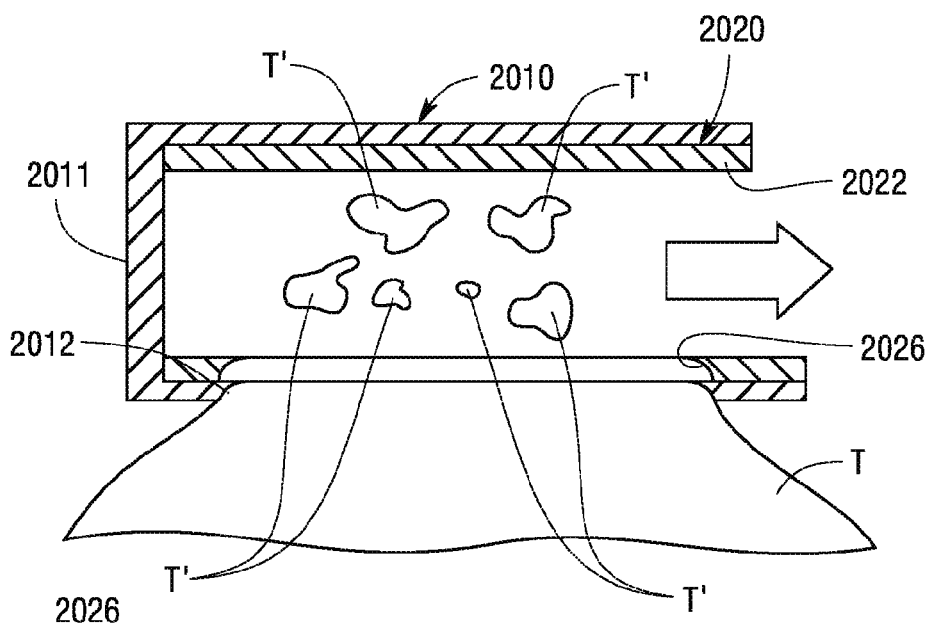
FIG. 38 is a cross-sectional view of distal portions of the outer sheath and blade embodiments depicted in FIG. 37 cutting tissue.

Also in various embodiments, a distal end portion 2011 of the hollow outer sheath is closed and at least one opening or window 2012 is provided therein to expose a distal tissue cutting portion 2025 of the blade 2020. In at least one embodiment window 2012 comprises an elongated slot and the distal tissue cutting portion also comprises an elongated slot 2026 in the blade 2020 (FIGS. 37 and 38). Thus, suction may be applied from the suction source 244 into the hollow portion of blade 2020 through the port 240, the proximal sheath opening 2014 and the blade discharge port 2028. As the distal openings 2026, 2012 coincide, tissue "T" may be drawn into the hollow distal portion 2022 of blade 2020 as shown in FIG. 38. The severed portions of tissue "1" may pass through the hollow distal portion 2022 of blade 2020 and out through openings 2028, 2014 and into the collection receptacle 243.

In use, the clinician may activate the rotating blade 2020 to cut and evacuate tissue. When a bleeder is encountered, the clinician may activate the ultrasonic transducer assembly 314 to send ultrasonic motions to the outer sheath 2010 for coagulation purposes. For example, spinal fusion surgeries require the removal of disc material due to a variety of disease states. Often times this material is toughened and requires quite a bit of force with conventional instrumentation to break up the disc and remove its fragments. Once the disc material is removed, the end plates must be scraped to reveal fresh surfaces to promote fusion of the plates to the cage. The plates must also be shaped to provide a good fit with the type of cage being used. Conventional instrumentation generally requires high forces from the surgeon very close to critical structures. In other embodiments, the motor may be coupled to rotate the ultrasonic transducer assembly and the blade may be attached to the ultrasonic transducer assembly as was described above so that the blade rotates and may have ultrasonic motion applied thereto.

Figure 39:
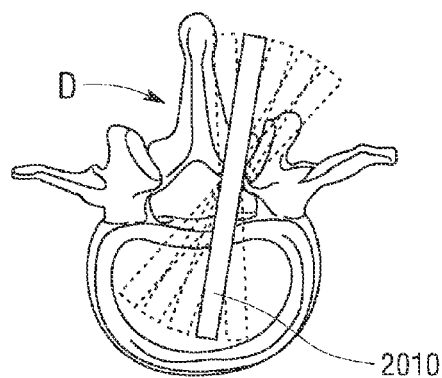
FIG. 39 illustrates use of the surgical instrument embodiment of FIG. 36 in connection with performing a discectomy.
Figure 40:
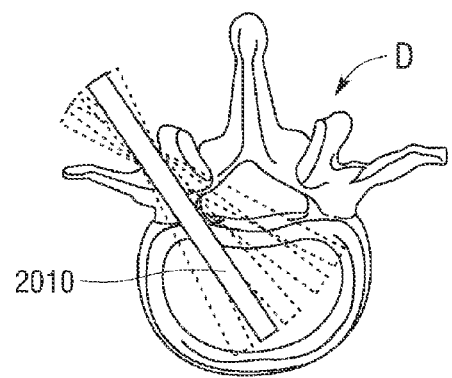
FIG. 40 depicts further use of the surgical instrument embodiment of FIG. 36 in connection with performing a discectomy.
Figure 41:
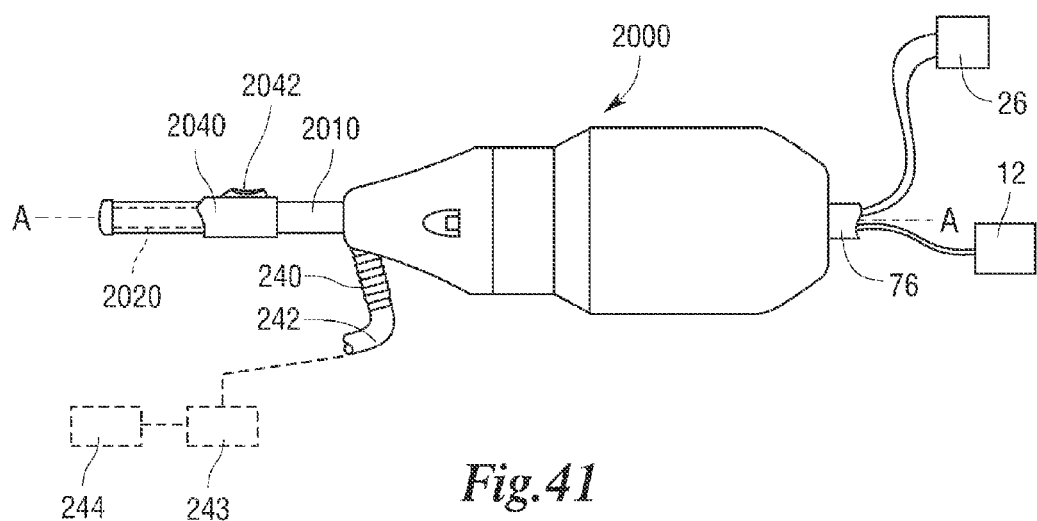
FIG. 41 is a side elevational view of the surgical instrument embodiment of FIG. 36 with a selectively retractable safety sheath mounted thereon.
Figure 44:
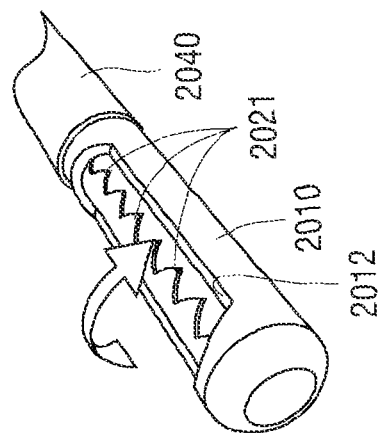
FIG. 44 is another partial perspective view of the retractable safety sheath embodiment illustrated in FIGS. 41-43 with the safety sheath retracted to an open position.
Figure 43:
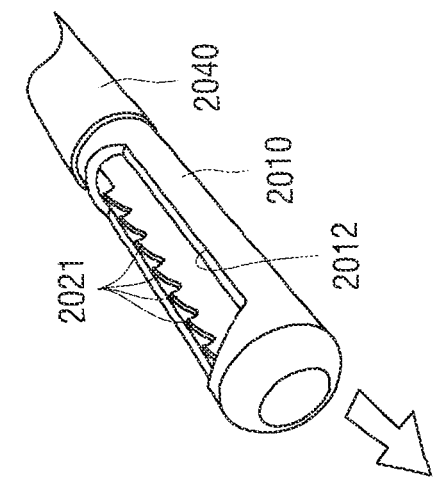
FIG. 43 is another partial perspective view of the retractable safety sheath embodiment illustrated in FIGS. 41 and 42 with the safety sheath retracted to an open position.
Figure 42:
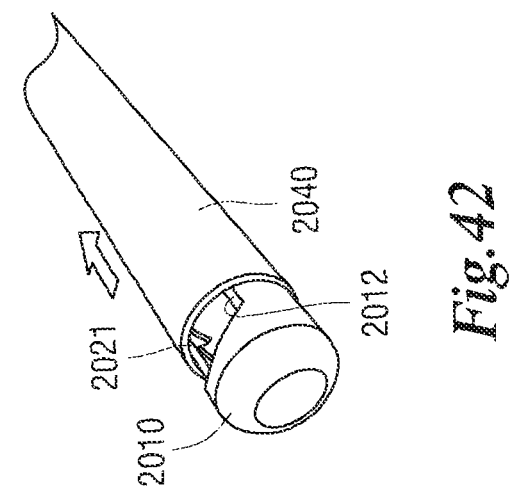
FIG. 42 is a partial perspective view of the retractable safety sheath embodiment illustrated in FIG. 41 starting to be retracted from a closed position.
Figure 45:
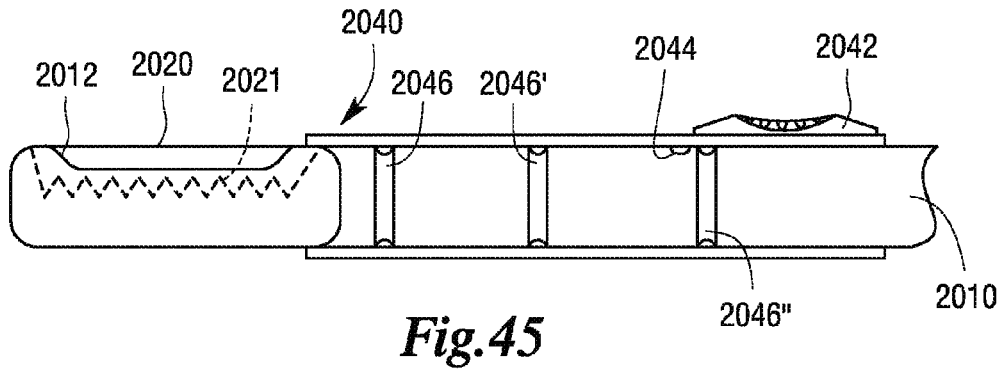
FIG. 45 is a side elevational view of a portion of the outer sheath and safety sheath embodiments illustrated in FIGS. 41-44 with the safety sheath shown in cross-section in an open position.
Figure 46:
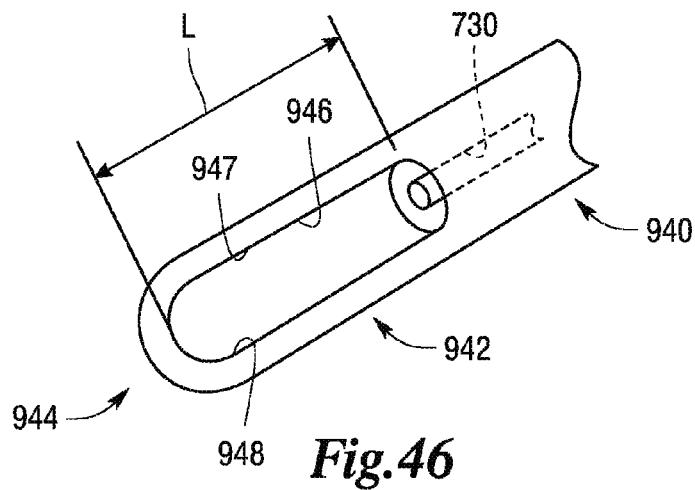
FIG. 46 is a perspective view of a portion of another non-limiting blade embodiment.

Use of the above-described surgical instrument 2000 may be particularly advantageous when performing, for example, a discectomy as shown in FIGS. 39 and 40. As can be seen in those drawings, the outer sheath 2010 may be inserted into the disc "D". The rotating blade 2020 may be used to shave off small pieces of disc and suction them out. Such arrangement eliminates the need for repeated insertion/removal of surgical tools. The device may also be employed to prepare the vertebrae endplates. In the embodiment depicted in FIGS. 41-45, the rotatable cutting blade 2020 has a series of serrated teeth 2021 formed on at least one side of the distal opening 2026 to further assist with the cutting of tissue drawn in through the opening 2012 in the outer sheath 2010. Also in this embodiment, a retractable safety shield 2040 is movably mounted on the outer sheath 2010 and is selectively movable from a closed position substantially covering the opening 2012 in the outer sheath 2010 to an open position exposing the opening 2012 (FIGS. 43 and 44). Such arrangement covers the teeth 2021 on the blade 2020 during insertion and removal of the outer sheath 2010 adjacent vital nerves and other critical tissues. To facilitate movement of the safety sheath 2040 on the outer sheath 2010, a thumb control tab 2042 (FIGS. 41 and 45) may be formed on the proximal end of the safety sheath 2040 to enable the clinician to apply sliding actuation forces thereto. In addition, in various embodiments, a retainer protrusion 2044 may be formed on the safety sheath 2040 to engage at least one detent or groove 2046 provided in the outer sheath 2010 to retain the safety sheath 2040 in a corresponding open or closed position. For example, one detent or groove 2046 may correspond to a closed position (wherein the safety sheath 2040 covers the opening 2012) and another detent or groove 2046' may correspond to a partially opened position (wherein a portion of the opening 2012 is exposed) and another detent or groove 2046" may correspond to a fully opened position (wherein the opening 2012 is fully exposed).

Figure 47:
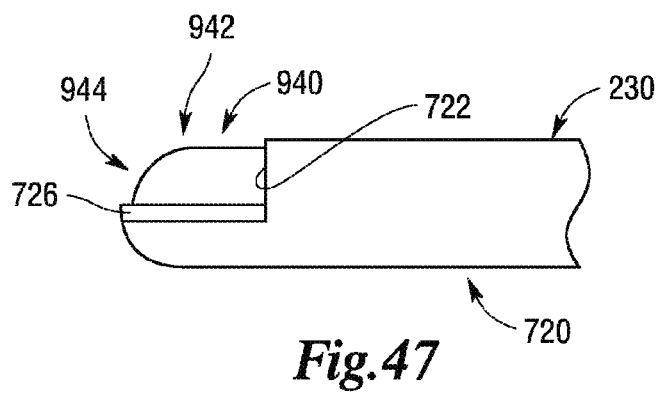
FIG. 47 is a side view of a portion of another hollow outer sheath and blade arrangement of another non-limiting embodiment.
Figure 48:
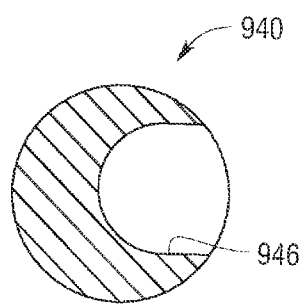
FIG. 48 is a cross-sectional view of another non-limiting blade embodiment.
Figure 49:
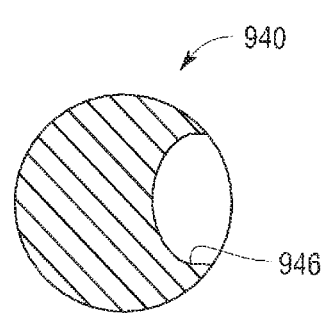
FIG. 49 is a cross-sectional view of another non-limiting blade embodiment.
Figure 50:
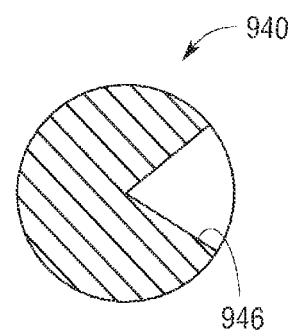
FIG. 50 is a cross-sectional view of another non-limiting blade embodiment.
Figure 51:
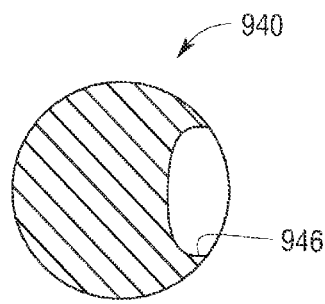
FIG. 51 is a cross-sectional view of another non-limiting blade embodiment.

FIGS. 46-51 illustrate a blade 940 that has a nearly straight distal tissue cutting portion 942. Such blade configuration may reduce potential impedance and power increases when the blade 940 is used in an aqueous environment when compared to the impedance and power requirements of various other blade configurations when used in that environment. That is, such relatively straighter blade designs may require less power to operate in an aqueous environment. The blade 940 may have a round or blunted distal end 944 and a groove 946 that forms cutting edges 947, 948 for cutting tissue when the blade 940 is used in connection with an outer sheath 230 as described above. The groove may have a length "L" of, for example, one (1) inch. The blade 942 may also have a suction passage 730 of the type and construction described above. As shown in FIG. 47, a low friction fender or pad 726 of the type and construction described above may be employed around the exposed distal end portion 720 of the outer sheath 230. FIGS. 48-51 depict alternative cross-sectional shapes of a blade 940 where differently shaped grooves 946 are employed.

Figure 53:
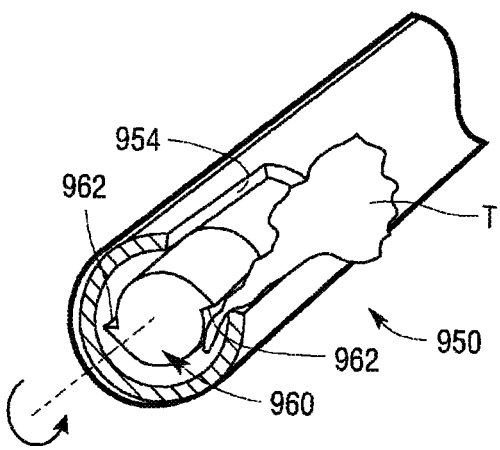
FIG. 53 is another partial cross-sectional view of the outer sheath and blade embodiment of FIG. 52 interacting with body tissue.
Figure 54:
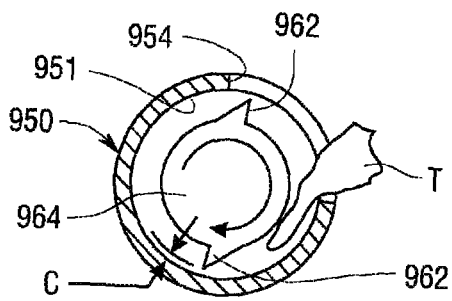
FIG. 54 is an end cross-sectional view of the outer sheath and blade arrangement depicted in FIGS. 52 and 53 interacting with body tissue.
Figure 55:
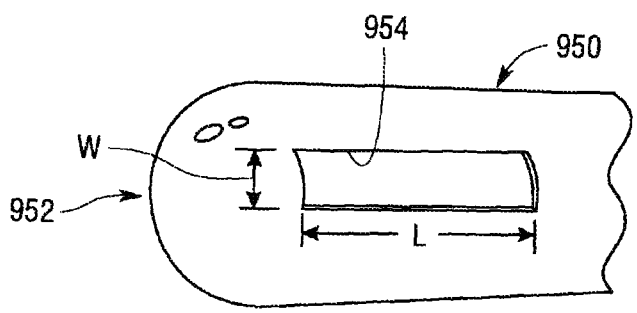
FIG. 55 is a partial perspective view of another non-limiting outer sheath embodiment.

FIGS. 52-55 depict another non-limiting blade and sheath embodiment. This embodiment employs a hollow outer sheath 950 that may be attached to the nosepiece or the ultrasonic transducer assembly of any of the surgical instruments described above by any suitable fastening method or connection arrangement. As can be seen in FIG. 55, the outer sheath 950 has a closed rounded or blunted nose portion 952 and an elongated rectangular-shaped window or opening 954. In one embodiment, for example, the rectangular-shaped window 954 has a width "W" that is approximately one-fourth of the circumference of the hollow outer sheath 950 and a length of approximately 0.25 inches. The sheath 950 may be fabricated from, for example, stainless steel.

Figure 52:
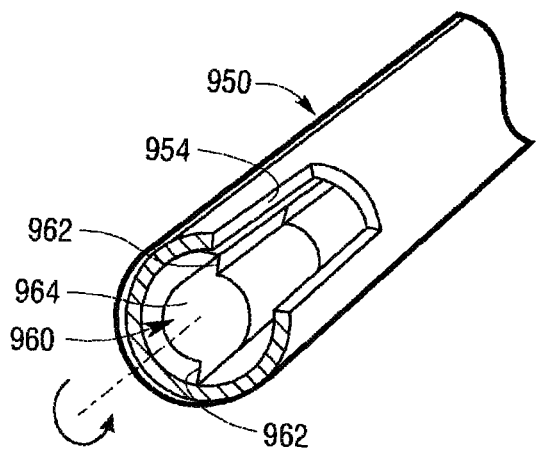
FIG. 52 is a partial cross-sectional view of another non-limiting outer sheath and blade embodiment.

This embodiment also employs a blade 960 that can be used in connection with any of the surgical instrument embodiments described above or others. For example, a waveguide or proximal portion of the blade may be configured for attachment to the instrument's ultrasonic horn or motor drive shaft by a threaded or other connection. As can be seen in FIGS. 52-54, the blade 960 has a pair of radially-opposed sharpened cutting edges 962 formed thereon that serve to cut tissue "T" that is drawn into the window 954 of the outer sheath 950. In various embodiments, the blade 960 may be fabricated from, for example, Titanium and be sized relative to the outer sheath 950 such that a clearance "C" is provided between the inner wall 951 of the outer sheath 950 and the tips of the radially opposed sharpened cutting edges 962. See FIG. 54. In some embodiments, for example, the clearance "C" may be approximately 0.001 inches. In this embodiment, the blade 960 may be fabricated from, for example, Titanium and have a flattened distal end 964. In use, when gross rotary motion is applied to the blade 960 in any of the various manners described above and suction is applied within the hollow outer sheath 950, the tissue "T" is drawn in through the window 954 and trapped between the blade 960 and the inner wall 951 of the outer sheath 950. This action isolates the tissue "T" long enough to cut when, for example, the device is employed in an aqueous environment as will be discussed in further detail below. In some embodiments, the cutting edges 962 may be serrated. In other embodiments the cutting edges 962 are not serrated.

Figure 56:
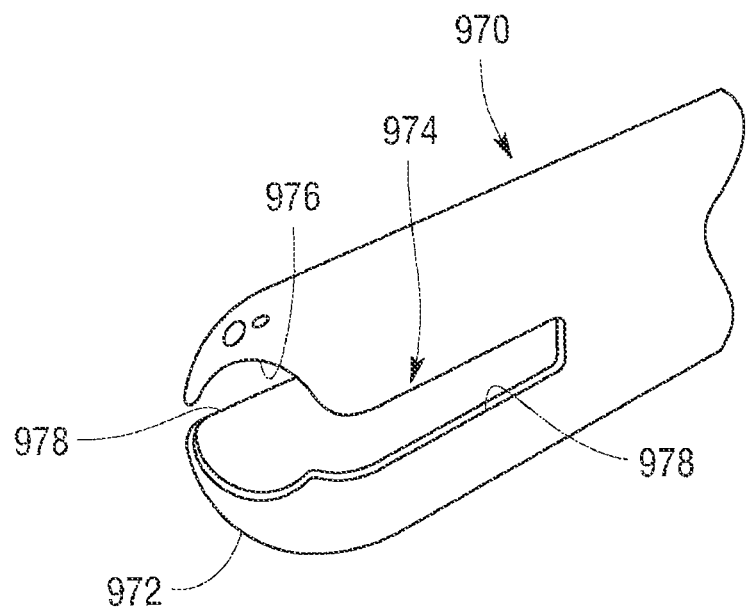
FIG. 56 is a partial perspective view of another non-limiting outer sheath embodiment.
Figure 57:
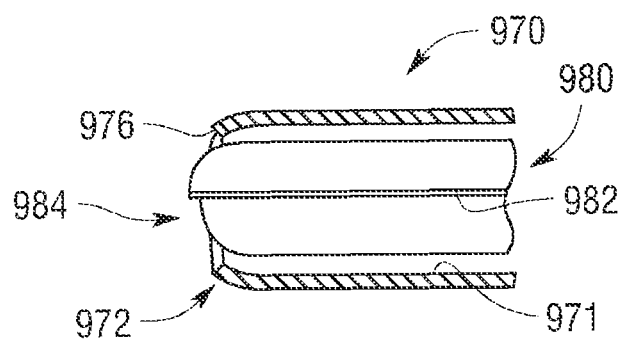
FIG. 57 is a partial cross-sectional view of the outer sheath embodiment of FIG. 56 supporting another non-limiting blade embodiment.

FIG. 57 depicts another non-limiting blade and sheath embodiment. This embodiment employs a hollow outer sheath 970 that may be attached to the nosepiece or ultrasonic transducer assembly of any of the various instruments described above. As can be seen in FIG. 56, the outer sheath 970 has a rounded or blunted nose portion 972 and an elongated window or opening 974 that forms a blade access hole 976 in the nose portion 972 and two radially-opposed lateral window portions 978. In one embodiment, for example, wherein the outer diameter of the outer sheath 970 is approximately 0.157 inches, the diameter of the blade access hole 976 may be approximately 0.125 inches. The lateral window portions 978 may each have a width "W" of approximately 0.090 inches and a length "L" of approximately 0.25 inches. Other window sizes/configurations may be employed. The sheath 970 may be fabricated from, for example, stainless steel.

This embodiment also employs a blade 980 that has a waveguide or proximal portion that is configured for attachment to the ultrasonic horn or motor drive shaft of any of the various surgical instrument embodiments described above 324 by a threaded or other suitable connection. In various embodiments, the blade 980 may be substantially the same as blade 960 described above (with radially-opposed sharpened cutting edges 982), except that blade 980 has a rounded/substantially blunted distal tip portion 984 that protrudes out through the blade access hole 976 in the outer sheath 970. See FIG. 57. In various embodiments, the blade 980 may be fabricated from, for example, Titanium and be sized relative to the outer sheath 970 such that a clearance is provided between the inner wall 971 of the outer sheath 970 and the tips of the radially opposed sharpened cutting edges 962. In some embodiments, for example, the clearance may be approximately 0.001 inches. In use, when gross rotary motion is applied to the blade 980 in any of the various manners described above and suction is applied within the hollow outer sheath 970, the tissue is drawn in through the window portions 978 and trapped between the blade 980 and the inner wall 971 of the outer sheath 970. This action isolates the tissue long enough to cut when, for example, the device is employed in an aqueous environment as will be discussed in further detail below. Also, in this embodiment, when the blade 980 is ultrasonically powered, the clinician can use the exposed distal tip portion 984 for spot ablation of fibrous tissue or for spot coagulation purposes. In some embodiments, the cutting edges 982 may be serrated. In other embodiments the cutting edges 982 are not serrated.

Figure 58:
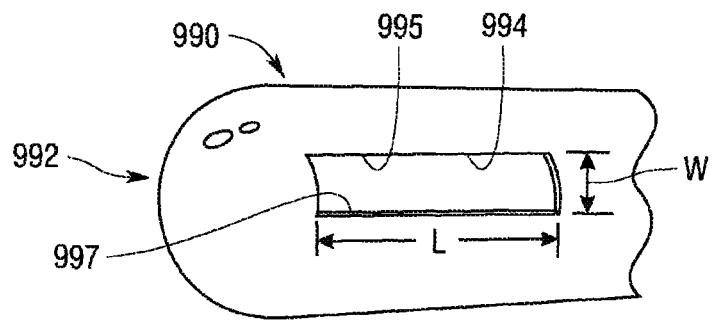
FIG. 58 is a partial perspective view of another non-limiting outer sheath embodiment.
Figure 59:
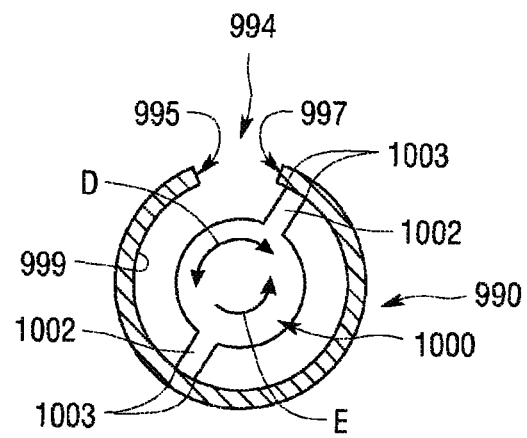
FIG. 59 is a cross-sectional view of another non-limiting outer sheath and blade embodiment.
Figure 60:
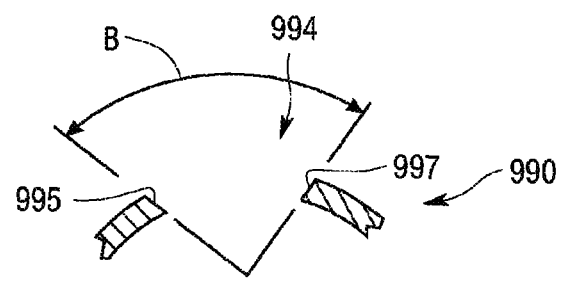
FIG. 60 illustrates an angle between the cutting edges formed on a non-limiting outer sheath embodiment.

FIG. 59 depicts another non-limiting blade and sheath embodiment. This embodiment employs a hollow outer sheath 990 that may be attached to the nosepiece or ultrasonic transducer assembly of any of the above-described surgical instruments by any suitable fastening method or connection arrangement. As can be seen in FIG. 58, the outer sheath 990 has a closed rounded or blunted nose portion 992 and an elongated rectangular-shaped window or opening 994. In one embodiment, for example, the rectangular-shaped window 994 has a width "W" that is approximately 0.100 inches and a length of approximately 0.25 inches. The sheath 990 may be fabricated from, for example, a polyamide or similar material that does not result in the heating of a blade 1000 from contact therewith. The window 994 may be defined by sharp edges 995, 997. As can be seen in FIG. 60, edges 995, 997 may be provided with an angle "B" therebetween. In some embodiments, angle "B" may be approximately 110 degrees.

These embodiments also employ a blade 1000 that has a waveguide or proximal portion that is configured for attachment to the ultrasonic horn or motor drive shaft of any of the above-described surgical instruments or others by a threaded or other suitable connection arrangement. As can be seen in FIG. 59, the blade 1000 may have a pair of radially-opposed sharpened cutting portions 1002 formed thereon that serve to cut tissue that is drawn into the window 994 in the outer sheath 990. In various embodiments, the blade 1000 may be fabricated from, for example, Titanium. The cutting portions 1002 of the blade 1000 may have sharp cutting corners 1003 formed thereon. In some embodiments, the cutting corners 1003 may be serrated. In other embodiments the cutting corners 1003 are not serrated. The cutting portions 1002 may be sized relative to the outer sheath 990 to establish a tissue shearing action between the cutting corners 1003 and the sharp edges 995, 996 of the window opening 994 as the blade 1000 is rotated or oscillated back and forth within the outer sheath 990. The blade 1000 may be sized relative to the outer sheath 990 to create a slip fit therebetween that otherwise prevents tissue from becoming trapped between those two components. The blade 990 could rotate back and forth (arrow "D") or rotate in a single direction (arrow "E") and if desire be ultrasonically activated as well as was discussed above. See FIG. 59. In use, when gross rotary motion is applied to the blade 1000 in any of the various manners described above and suction is applied within the hollow outer sheath 990, the tissue "T" is drawn in through the window 994 and trapped between the blade 1000 and the inner wall 999 of the outer sheath 990. This action isolates the tissue long enough to cut when, for example, the device is employed in an aqueous environment as will be discussed in further detail below.

Figure 61:
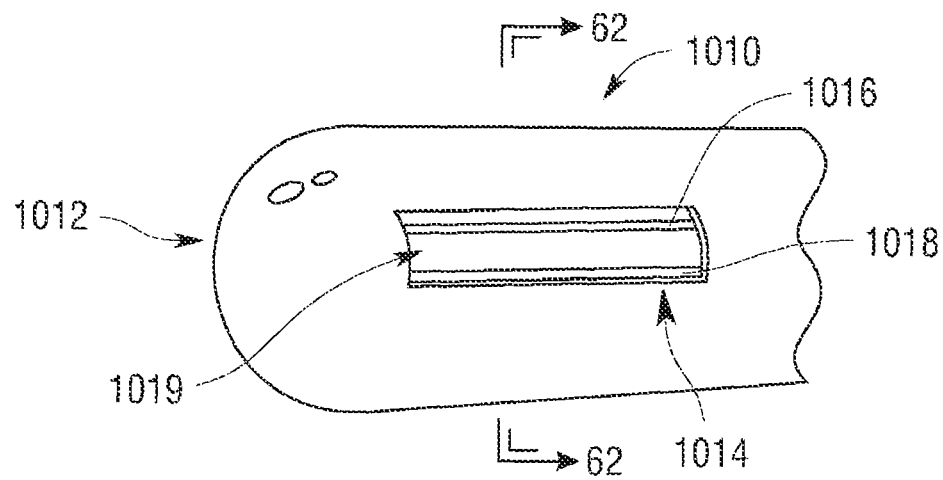
FIG. 61 is a perspective view of another non-limiting outer sheath embodiment.
Figure 62:
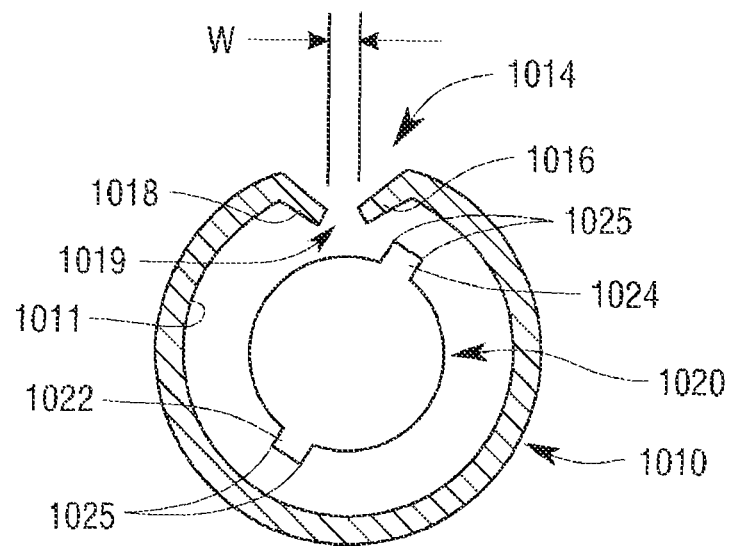
FIG. 62 is a cross-sectional view of the outer sheath and blade embodiment of FIG. 61.

FIG. 62 depicts another non-limiting blade and sheath embodiment. This embodiment employs a hollow outer sheath 1010 that may be attached to the nosepiece or ultrasonic transducer assembly of any of the above described surgical instruments by any suitable fastening method or connection arrangement. As can be seen in FIG. 61, the outer sheath 1010 may have a closed rounded or blunted nose portion 1012 and an elongated rectangular-shaped window or opening 1014. In one embodiment, for example, the window 1014 has a first coined or depressed edge 1016 and a second coined or depressed edge 1018 to define an opening 1019 that may have a width W" that is approximately 0.100 inches. Window 1014 may have a length of approximately 0.25 inches. The sheath 1010 may be fabricated from, for example, stainless steel These embodiments also employ a blade 1020 that has a waveguide or proximal portion that is configured for attachment to the ultrasonic horn or motor drive shaft of any of the above-described surgical instruments or others by a threaded or other suitable connection. As can be seen in FIG. 62, the blade 1020 may have a pair of radially-opposed sharpened cutting portions 1022, 1024 formed thereon. The blade 1020 may be fabricated from, for example, Titanium and have relative sharp cutting corners 1025 formed on each cutting portions 1022, 1024. In some embodiments, the cutting corners 1025 may be serrated. In other embodiments the cutting corners 1025 are not serrated. The cutting portions 1022, 1024 may be sized relative to the outer sheath 1010 to establish a tissue shearing action between the depressed edges 1016, 1018 and the cutting corners 1025 as the blade 1020 is rotated or oscillated within the outer sheath 1010. Such arrangement forms a relatively small localized area to lessen contact issues between the blade and the outer sheath by also facilitates a scissoring effect on the tissue. In use, when gross rotary motion is applied to the blade 1020 in any of the various manners described above and suction is applied within the hollow outer sheath 1010, the tissue is drawn in through the opening 1019 and trapped between the blade 1020 and the inner wall 1011 of the outer sheath 1010. This action isolates the tissue long enough to cut when, for example, the device is employed in an aqueous environment as will be discussed in further detail below.

Figure 63:
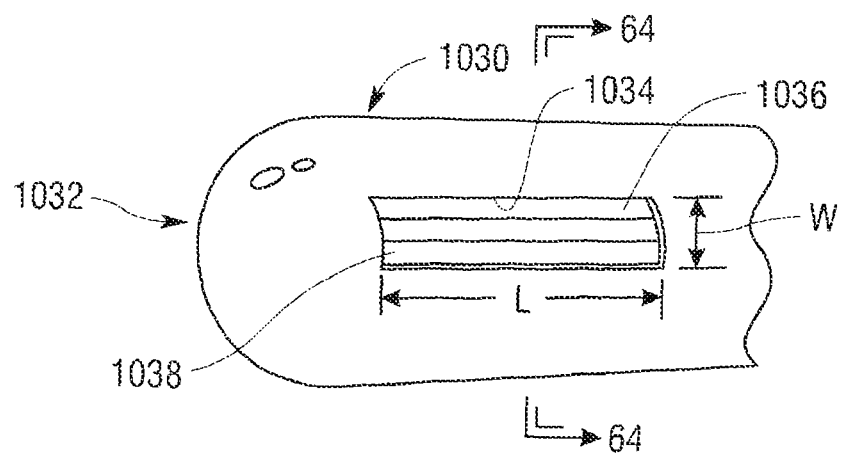
FIG. 63 is a perspective view of another non-limiting outer sheath embodiment.
Figure 64:
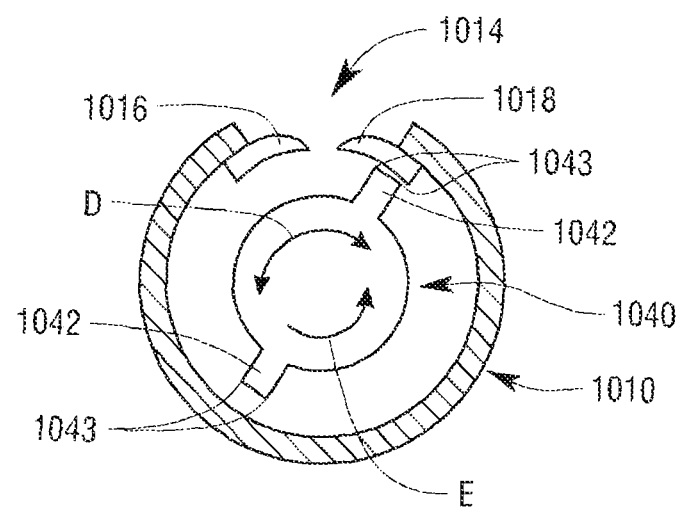
FIG. 64 is a cross-sectional view of the outer sheath and blade embodiment of FIG. 63.

FIG. 64 depicts another non-limiting blade and sheath embodiment. This embodiment employs a hollow outer sheath 1030 that may be attached to the nosepiece or ultrasonic transducer assembly of any of the above-described surgical instruments. As can be seen in FIG. 63, the outer sheath 1030 may have a closed rounded or blunted nose portion 1032 and an elongated rectangular-shaped window or opening 1034. This embodiment may further include a pair of sharpened cutting inserts 1036, 1038. The cutting inserts 1036, 1038 may be fabricated from, for example, hardened stainless steel and be attached within the hollow sheath 1030 by, for example, welding. Window 1034 may have a width W" that is approximately 0.100 inches and a length of approximately 0.25 inches. The sheath 1030 may be fabricated from, for example, stainless steel.

These embodiments also employ a blade 1040 that has a waveguide or proximal portion that is configured for attachment to the ultrasonic horn or motor drive shaft of any of the surgical instruments described herein or others by a threaded or other suitable connection. As can be seen in FIG. 64, the blade 1040 has a pair of radially-opposed cutting portions 1042 formed thereon that have relatively sharp cutting corners 1043. In some embodiments, the cutting corners 1043 may be serrated. In other embodiments the cutting corners 1043 are not serrated. In various embodiments, the blade 1040 may be fabricated from, for example, Titanium and be sized relative to the cutting inserts 1036, 1038 to establish a tissue shearing action between the sharp cutting corners 1043 and the cutting portions 1042 as the blade 1020 is rotated or oscillated within the hollow outer sheath 1030. The outer diameter of the blade 1020 is smaller than the inner diameter of the outer sheath 1030 to provide clearance for the blade 1040 during operation. The only instance of contact would be between the cutting portions 1042 of the blade 1040 and the inserts 1036, 1038 along the window opening 1034 wherein the tissue is pulled in by the suction.

Figure 65:
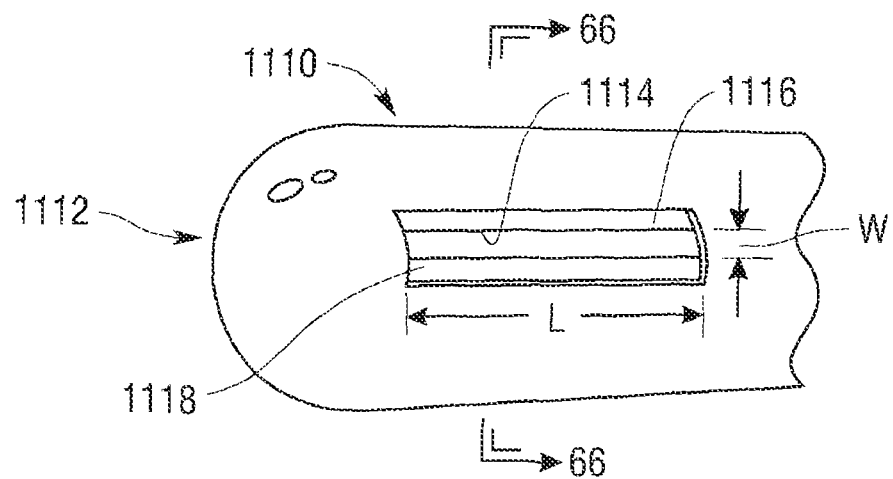
FIG. 65 is a perspective view of another non-limiting outer sheath embodiment.
Figure 66:
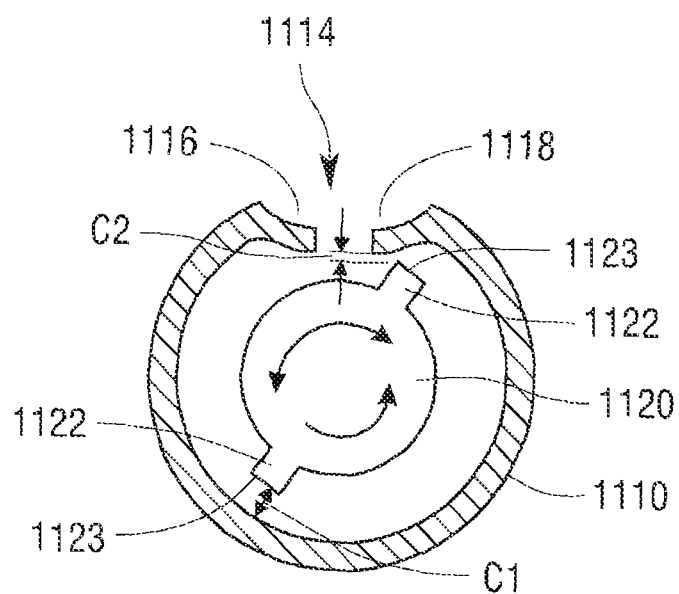
FIG. 66 is a cross-sectional view of the outer sheath and blade embodiment of FIG. 65.

FIG. 66 depicts another non-limiting blade and sheath embodiment. This embodiment employs a hollow outer sheath 1110 that may be attached to the nosepiece or ultrasonic transducer assembly of any of the surgical instruments described above by any suitable fastening method or connection arrangement. As can be seen in FIG. 65, the outer sheath 1110 may have a closed rounded or blunted nose portion 1112 and an elongated rectangular-shaped window or opening 1114. In this embodiment, the lateral edge portions 1116, 1118 of the window 1114 are coined or depressed inward. Window 1014 may have a width W" that is approximately 0.10 inches and a length of approximately 0.25 inches.

These embodiments also employ a blade 1120 that has a waveguide or proximal portion that is configured for attachment to the ultrasonic horn or motor drive shaft of any of the surgical instrument embodiments described above or others by a threaded or other suitable connection arrangement. As can be seen in FIG. 66, the blade 1120 has a pair of radially-opposed cutting portions 1122 formed thereon that have relatively sharp cutting corners 1023. In some embodiments, the cutting corners 1023 may be serrated. In other embodiments the cutting corners 1023 are not serrated. In various embodiments, the blade 1020 may be fabricated from, for example, Titanium and be sized relative to the depressed edges 1116, 1118 to establish a tissue shearing action between the sharp cutting corners 1023 and the cutting portions 1122 as the blade 1120 is rotated or oscillated. Such arrangement defines a larger clearance C1 between the cutting portions 1122 of the blade 1120 and the inner wall 1111 of the sheath 1110. To form a tissue shearing action between the lateral edges 1116, 1118 and the cutting portions 1122, a clearance C2 that is less than C1 is provided.

Figure 67:
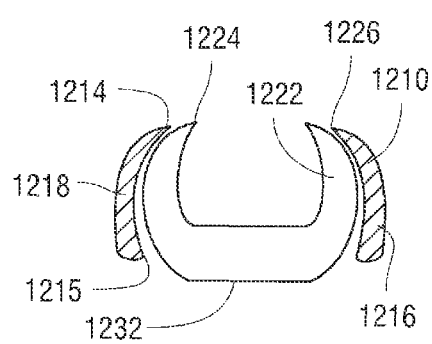
FIG. 67 is a cross-sectional end view of another non-limiting outer sheath and blade arrangement.
Figure 68:
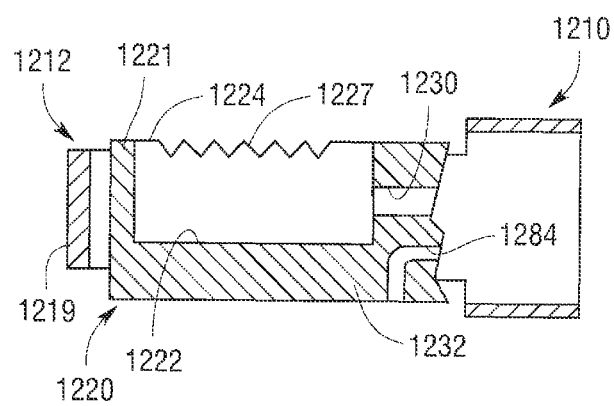
FIG. 68 is a partial side cross-sectional view of the outer sheath and blade arrangement of FIG. 67.
Figure 69:
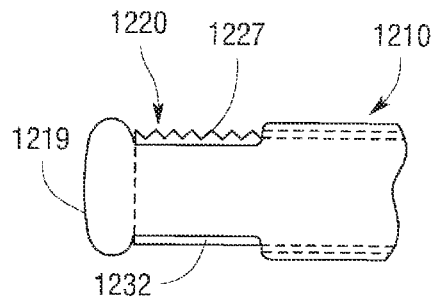
FIG. 69 is a partial side view of a distal end portion of the outer sheath and blade arrangement of FIGS. 67 and 68.

FIGS. 67-69 depict another non-limiting blade and sheath embodiment. This embodiment employs a hollow outer sheath 1210 that may be attached to the nosepiece or ultrasonic transducer assembly of any of the surgical instruments described above. The hollow outer sheath 1210 has a distal nose portion 1212 that includes an upper opening 1214 and a lower opening 1215 that serve to define arcuate lateral side portions 1216, 1218. The distal nose portion 1212 may further have a closed end 1219 that extends between the lateral side portions 1216, 1218.

This embodiment further comprises a blade 1220 that has a waveguide or proximal portion that is configured for attachment to the ultrasonic transducer assembly of any of the surgical instruments described above. The blade 1220 further has a distal end portion 1221 that has a cavity 1222 that serves to define a pair of arcuate cutting portions 1224, 1226 that extend above the arcuate lateral side portions 1216, 1218 of the hollow sheath 1210. One, both or neither of the cutting portions 1224, 1226 may have serrated teeth 1227. In the embodiment depicted in FIG. 67, the cavity 1222 has a cross-sectional shape that roughly resembles a flat bottom "C". However, the cavity 1222 may have other cross-sectional shapes. At least one suction passage 1230 may be provided through the blade 1220 as shown. The suction passage may communicate with a source of suction (not shown).

In various embodiments, the blade 1220 may be fabricated from, for example, Titanium and be sized relative to the distal nose portion 1212 of the hollow sheath 1210 such that the bottom portion 1232 of the blade 1220 extends downward beyond the lateral sides 1216, 1218 of the nose portion 1212. Likewise, the cutting edges of the arcuate side portions 1224, 1226 extend above the lateral sides 1216, 1218 as shown in FIG. 67. The exposed bottom portion 1232 of the blade 1220 may be used, for example, to coagulate tissue, while the cutting edges 1224, 1226 may be used to cut and sever tissue.

Figure 70:
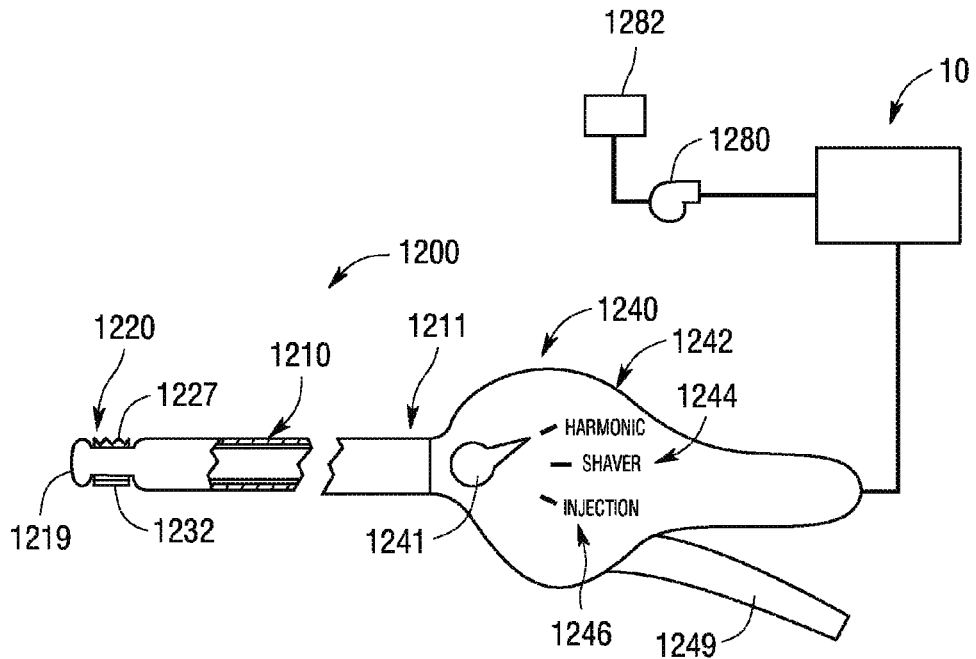
FIG. 70 is a side view of a non-limiting handpiece housing embodiment attached to the outer sheath and blade arrangement of FIGS. 67-69.
Figure 71:
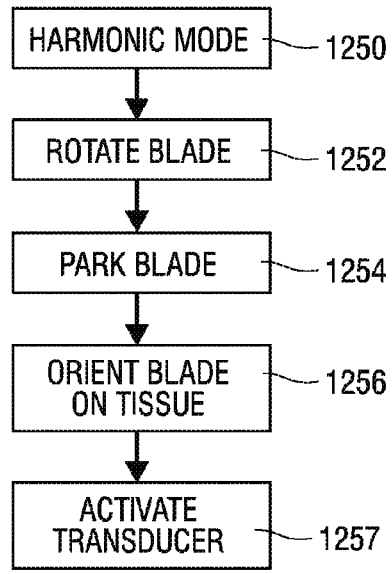
FIG. 71 depicts a method of using the surgical instrument embodiment of FIG. 70.

The proximal end 1211 of the hollow sheath 1210 protrudes from a handle housing 1240 as shown in FIG. 70. The handle housing 1240 houses an ultrasonic transducer assembly, a motor, and a slip ring assembly as was described above and is coupled to a control system 10. The handle housing 1240 may include a selector switch 1241 which enables the clinician to switch between a first "ultrasonic" mode 1242, a second "shaver" mode 1244, and a third "injection" mode 1246. The switching mechanism 1241 communicates with the control system 10 to automatically orient the blade 1220 in a desired rotational orientation. For example, to employ the device 1200 in the ultrasonic mode 1242, the clinician switches the selector switch 1241 to the ultrasonic mode position 1242 (depicted as action 1250 in FIG. 71). When in the first ultrasonic configuration 1242, the motor will rotate the blade 1220 to the position shown in FIGS. 67 and 68 (depicted as action 1252 in FIG. 71) and then park it in that position to expose the bottom portion 1232 of the blade 1220 through the hollow sheath 1210 (depicted as action 1254 in FIG. 71). When in that position, the ultrasonic transducer assembly is activated to enable the bottom portion 1232 to be used to achieve hemostasis (depicted as action 1257 in FIG. 71). More particularly, when in the ultrasonic mode 1242, the clinician may orient the bottom portion 1232 against the tissue that is bleeding and then apply firm pressure to the tissue (depicted as action 1256 in FIG. 71) with the exposed portion 1232 of the blade 1220. The clinician then activates the ultrasonic transducer assembly to achieve hemostasis (depicted as action 1258 in FIG. 71). In alternative embodiments, the device 1200 may be provided with a series of switches/buttons as was described above that communicate with a control system such that activation of one switch may initiate rotation. Activation of another switch may initiate rotatable oscillation and activation of another switch may, in cooperation with the control system rotate the blade to the ultrasonic position and park it and thereafter activate the ultrasonic transducer assembly or in still other embodiments, the ultrasonic transducer assembly may be activated by yet another separate switch. All of such alternative arrangements are within the scope of the various non-limiting embodiments disclosed herein and their respective equivalent structures.

Figure 72:
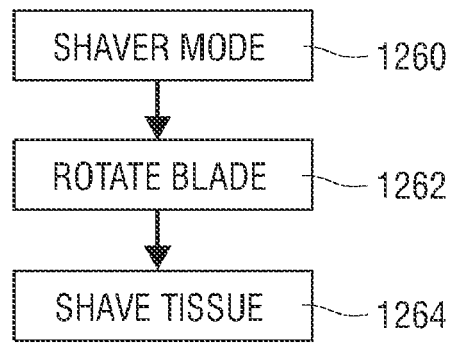
FIG. 72 depicts another method of using the surgical instrument embodiment of FIG. 70.

FIG. 72 illustrates use of the device 1200 when in the shaver mode 1244. In particular, the selector switch 1241 is moved to the shaver position 1242 (depicted as action 1260 in FIG. 72). When in that position, the motor continuously rotates the blade 1220 within the hollow outer sheath 1210 (depicted as action 1262 in FIG. 72). In other embodiments, the motor may rotatably oscillate the blade 1220 back and forth within the outer sheath 1210 or in other embodiments, the selector switch may be movable to yet another position wherein the rotatable oscillation is initiated. In either case, the clinician may then contact tissue with the rotating or oscillating blade (1220) to cause the tissue to be shaved and evacuated through the suction passage 1230 (depicted as action 1264 in FIG. 72).

Figure 73:
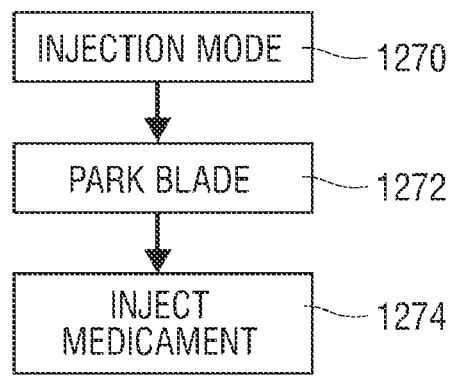
FIG. 73 depicts another method of using the surgical instrument embodiment of FIG. 70.

FIG. 73 illustrates use of the device 1200 when in the injection mode 1246. In particular, the selector switch 1241 is moved to the injection position 1246 (depicted as action 1270 in FIG. 73). When in that position, the blade 1220 is retained in a parked position (depicted as action 1272 in FIG. 73). The clinician may then orient the blade in a desired position and then inject the desired medicament (depicted as action 1274 in FIG. 73). One form of medicament that may be injected for example may comprise a cell generating drug sold under the trademark "Carticel". However, other drugs and medicaments could be employed. The injection action may be accomplished by orienting the blade 1220 to a position within the outer sheath 1210 such that a medicament passage 1284 extending through the blade 1220 is exposed through the outer sheath 1210 to enable medicament to be advantageously applied to the adjacent site. The medicament may then be injected by activating a pump 1280 that communicates with a source of the medicament 1282. See FIG. 70. In various embodiments, the device 1200 may have an injection trigger 1249 that communicates with the pump 1280 such that activation of the injection trigger 1249 will cause the pump 1280 to inject the medicament out through the passage 1284 (FIG. 68). In alternative embodiments, the medicament may be manually injected by, for example, a syringe into a port (not shown) that communicates with medicament passage 1284 in blade 1220.

FIGS. 74-77 depict another non-limiting surgical instrument embodiment 1300. The device 1300 may include any one of the handpiece devices 300, 400, 500 described above. For example, the device 1300 may include a handpiece 300 that incorporates the difference noted below. The handpiece 300 includes a blade 200 that has a waveguide or proximal portion that is coupled to an ultrasonic transducer assembly that, when activated, applies ultrasonic motion to the blade 200. The blade 200 may also be rotated by the motor arrangement contained within the handpiece 300 as described above. The blade 200 may extend through an inner sheath 1320 that protrudes from the handpiece 300. The blade 200 is free to be selectively vibrated and rotated within the inner sheath 1320. One or more seal members 1322 may be provided between the blade 200 and the inner sheath 1320 to prevent fluids and tissue from entering the area between the inner sheath 1320 and the blade 200. The seal members 1322 may be fabricated from, for example, silastic silicone.

Figure 76:
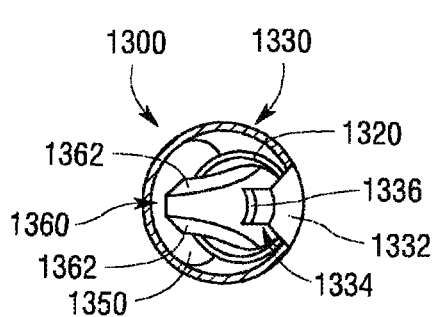
FIG. 76 is an end view of the outer sheath and blade arrangement of FIG. 75.
Figure 77:
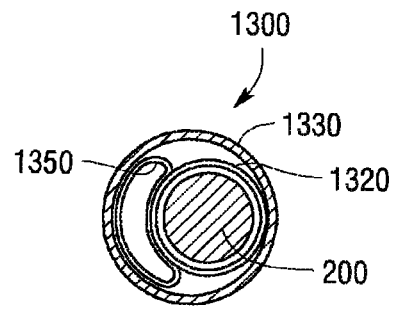
FIG. 77 is a cross-sectional end view of the sheath and blade arrangement of FIGS. 75 and 76.

The device 1300 may further include an outer sheath 1330 that is movably received on the inner sheath 1320. The outer sheath 1330 may be sized relative to the inner sheath 1320 such that a suction tube 1350 may extend between a portion of the inner sheath 1320 and a portion of the outer sheath 1330. The suction tube 1350 may communicate with a source of suction generally depicted as 1352. See FIG. 74. As can be seen in FIGS. 74-77, the outer sheath 1330 may include a swing arm portion 1332 that protrudes distally from a distal end portion 1331 of the outer sheath 1330. The swing arm 1332 may be relatively straight (FIG. 75) or it may have a slightly curved distal end 1334 (FIG. 76). As can be seen in FIG. 76, the distal end 1334 may have a sharpened cutting surface 1336 thereon. As can also be seen in FIGS. 74-76, in some embodiments, the blade 200 may have a curved blade tip 1360 that has a pair of lateral cutting edges 1362 formed thereon. In other embodiments, the blade tip 1360 may be straight. In some embodiments, the blade 200 may be rotated in the various manners discussed above. In other embodiments, the blade 200 may not rotate. In such embodiments, for example, the clinician may choose not to activate the motor for rotating the blade or the handpiece may comprise a handpiece that does not include a motor for rotating the blade.

Figure 74:
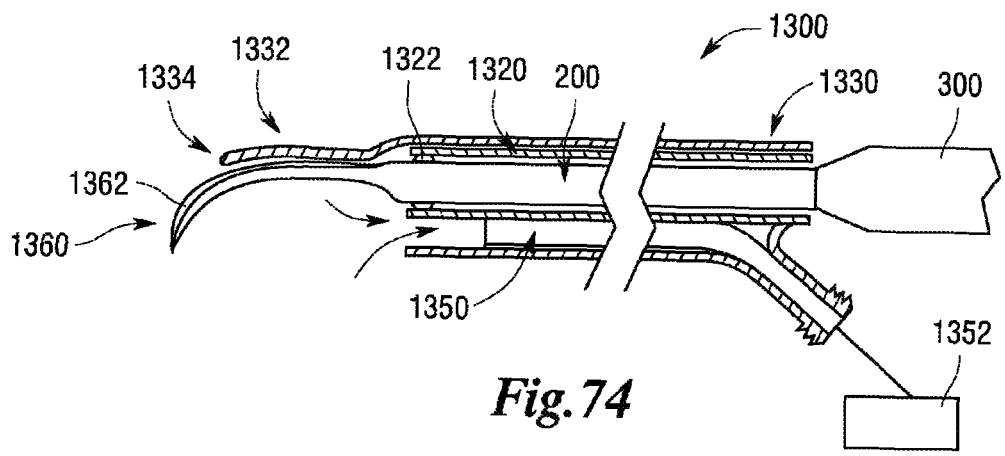
FIG. 74 is a partial side cross-sectional view of another non-limiting surgical instrument embodiment.
Figure 75:
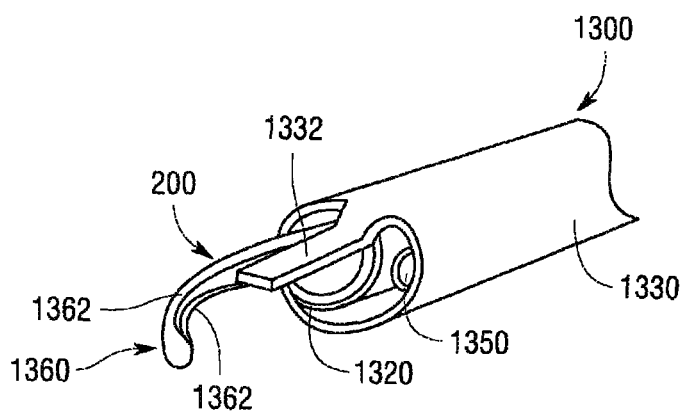
FIG. 75 is a perspective view of a portion of the outer sheath and blade arrangement employed with the surgical instrument embodiment depicted in FIG. 74.

In use, the swing arm portion 1332 may cover portions of the distal end 1360 of the blade 200. In one mode of use, the outer sheath 1330 is retained in position wherein the swing arm portion 1332 covers the back side of the blade 200 as shown in FIG. 74. Such arrangement leaves the curved blade tip 1360 exposed. When in such position, for example, the curved blade tip 1360 could be employed to transect tissue, such as the meniscus. In a second mode of operation, the swing arm portion 1332 is moving.

In the embodiment depicted in FIGS. 74-77, a suction tube 1350 is employed to draw loose tissue towards the blade tip 1360 and also remove small sections of transected tissue during cutting. In other embodiments, suction could occur in the annular space between the sheaths 1320, 1330. In still other embodiments, the blade 200 may have a suction path (not shown) extending therethrough which ultimately communicates with a source of suction as was described above. Such suction path would most likely exit the blade 200 at the node at the proximal end. In still other embodiments, no suction is employed.

In some embodiments, the swing arm portion 1332 may be permanently retained in position against the blade 200. In still other embodiments, a lubricious or low friction pad (not shown) may be mounted to the swing arm portion 1332 such that the pad contacts the blade 200. In other embodiments, a 0.002"-0.010" clearance may be provided between the swing arm portion 1332 and the blade 200. In other embodiments, the swing arm portion 1332 extends around the length of the curved portion of the blade 200 so that the entire blade 200 is covered from the back side.

The various non-limiting embodiments described hereinabove may be effectively employed in a connection with a variety of different surgical applications and are particularly well-suited for cutting and coagulating tissue in the aqueous environment of arthroscopic surgery. In such applications, however, if fluid passes between the blade or waveguide and the inner sheath, the fluid may enter the housing and damage the components therein. Various sealing arrangements are known for use with ultrasonically powered surgical instruments. For example, U.S. Pat. Nos. 5,935,144 and 5,944,737, the disclosures of which are each herein incorporated by reference in their respective entireties, each disclose various sealing arrangement for use with ultrasonic surgical instruments in the traditional environment of laparoscopic surgery and open surgery (i.e., non-aqueous environments). However, various non-limiting embodiments discussed below employ improved sealing arrangements that may be better suited for use in aqueous environments.

Figure 78:
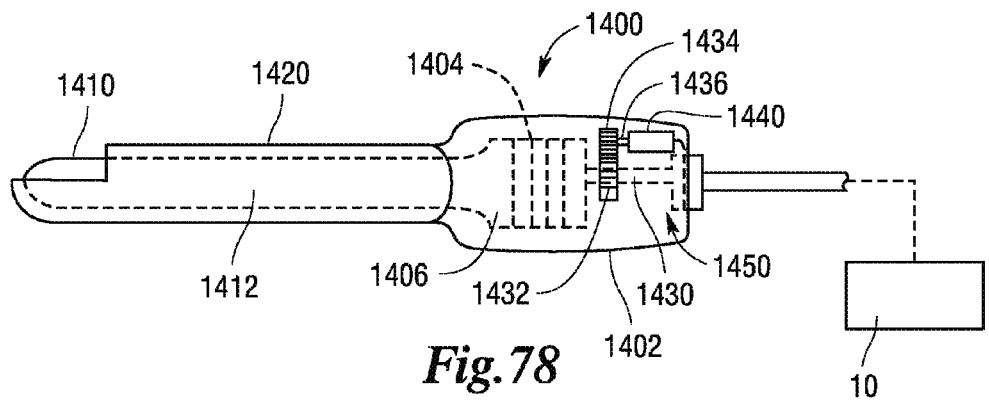
FIG. 78 is a side view of another non-limiting ultrasonic surgical instrument embodiment.

More particularly and with reference to FIG. 78, there is shown an ultrasonic device 1400 that includes a housing 1402 that rotatably supports an ultrasonic transducer assembly 1404 therein. For example, the ultrasonic transducer assembly 1404 may be rotatably supported within the housing 1402 by a series of bearings (not shown). An ultrasonic horn 1406 may be coupled to the ultrasonic transducer assembly 1404 and an ultrasonic implement 1410 is attached thereto by conventional means which may typically comprise a threaded arrangement. As used herein, the term "ultrasonic implement" may encompass any one of the blade and cutting member embodiments described herein. The portion of the ultrasonic implement 1410 that is coupled to the ultrasonic horn 1406 may be referred to as a waveguide portion 1412. The waveguide 1412 may comprise an integral portion of the ultrasonic implement 1410 or it may comprise a separate component attached thereto by, for example, a threaded connection. In the embodiment depicted in FIG. 78, the ultrasonic implement 1410 extends through a hollow outer sheath 1420. The outer sheath 1420 and the distal end of the ultrasonic implement 1410 may be configured in any one of the various blade and sheath configurations described hereinabove as well as others.

As can also be seen in FIG. 78, a proximal shaft 1430 is attached to the ultrasonic transducer assembly 1404. Attached to the proximal shaft 1430 is a driven gear 1432 that is in meshing engagement with a drive gear 1434 coupled to an output shaft 1436 of a motor 1440. Ultrasonic electrical signals and the motor control signals may be supplied from the control system 10 through a slip ring assembly 1450 of the type and construction described above. The device 1400 may further comprise the various control button arrangements described above, so that the device may be used in a ultrasonic mode, a non-ultrasonic mode (e.g., rotational shaving mode) and a combination of such modes. Unlike the various instruments described above, the motor 1440 is not coaxially aligned with the ultrasonic transducer assembly.

Figure 79:
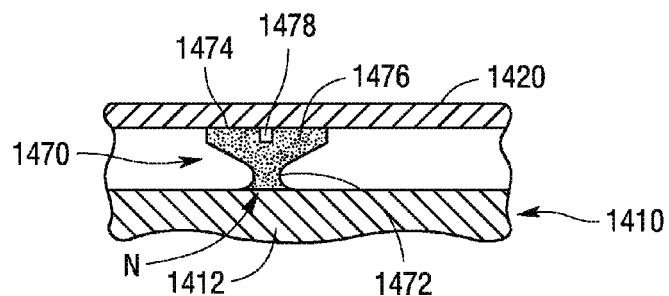
FIG. 79 is a partial cross-sectional view of a non-limiting seal embodiment between a hollow sheath and a waveguide portion of an ultrasonic implement embodiment.

FIG. 79 depicts a non-limiting embodiment of a seal assembly 1470 that may be employed between in the waveguide or proximal portion 1412 of the ultrasonic implement 1410 and the outer sheath 1420. The seal 1470 comprises an annular member that may be fabricated from silicon or other materials such as, for example, Ultem® and is over molded or otherwise sealingly attached to the waveguide 1412 at a node "N". The seal 1470 may have a first annular seal portion 1472 that is molded onto the waveguide 1412 at a node "N" and two axial seal portions 1474, 1476 that extend axially in opposite axial directions beyond the first annular seal portion 1472 and which are separated by a groove 1478. The groove 1478 may enable the two axial seal portions 1474, 1476 to somewhat flex relative to each other in sealing contact with the outer sheath 1420. The narrower first annular seal portion 1472 may avoid excessive heat build-up while providing a wider contact area wherein the seal 1470 contacts the outer sheath 1420.

Figure 80:
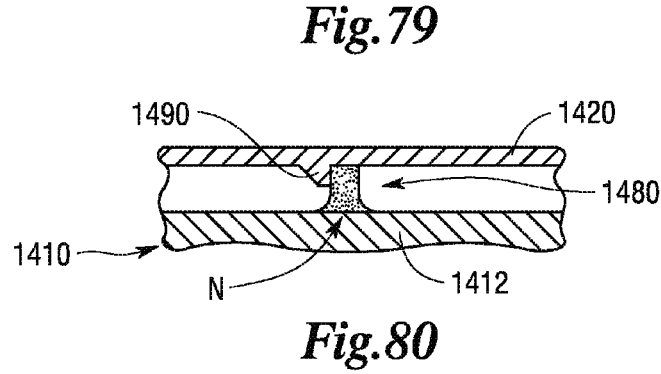
FIG. 80 is a partial cross-sectional view of another non-limiting seal embodiment between a hollow sheath and a waveguide portion of an ultrasonic implement embodiment.

FIG. 80 depicts a non-limiting embodiment of a seal 1480 that may be employed between in the waveguide or proximal portion 1412 of the ultrasonic implement 1410 and the outer sheath 1420. The seal 1480 comprises an annular member that may be fabricated from silicon or other materials, such as for example, Ultem® and is over molded or otherwise sealingly attached to the waveguide 1412 at a Node "N". The seal 1480 may be arranged to abut an inwardly-extending annular abutment ring 1490 formed on the outer sheath 1420. The seal 1480 is located distal with respect to the abutment ring 1490. When the fluid pressure builds up within the distal end of the outer sheath 1420, the seal 1480 is forced into the abutment ring 1490 thereby increasing the strength of the seal. The outer sheath 1420 may be fabricated from, for example, stainless steel.

Figure 81:
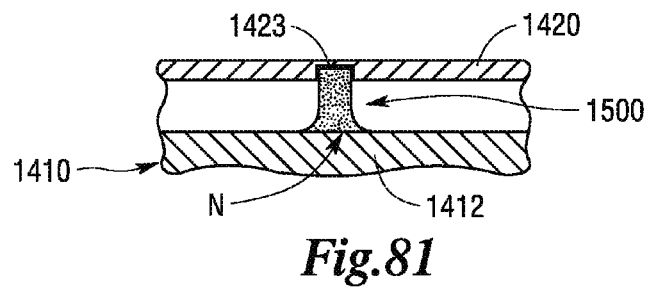
FIG. 81 is a partial cross-sectional view of another non-limiting seal embodiment between a hollow sheath and a waveguide portion of an ultrasonic implement embodiment.

FIG. 81 depicts a non-limiting embodiment of a seal 1500 that may be employed between in the waveguide portion 1412 of the blade 1410 and the outer sheath 1420. The seal 1500 comprises an annular member that may be fabricated from silicon or other materials, such as for example, Ultem® and is over molded or otherwise sealingly attached to the waveguide 1412 at a Node "N". The seal 1480 may be arranged to be received within an annular groove 1423 provided in the outer sheath 1420. The outer sheath 1420 may be fabricated from, for example, stainless steel.

Figure 82:
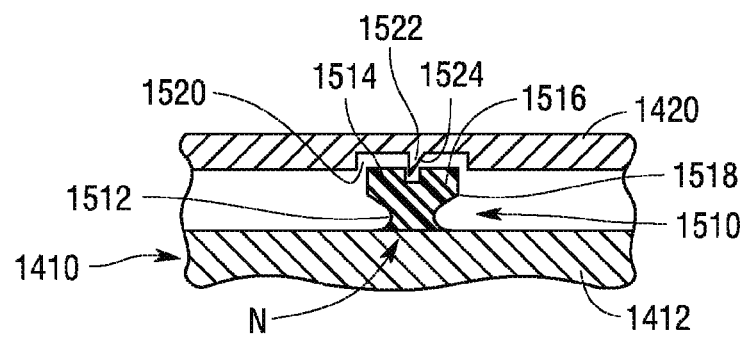
FIG. 82 is a partial cross-sectional view of another non-limiting seal embodiment between a hollow sheath and a waveguide portion of an ultrasonic implement embodiment.

FIG. 82 depicts a non-limiting embodiment of a seal 1510 that may be employed between in the waveguide or proximal portion 1412 of the ultrasonic implement 1410 and the outer sheath 1420. The seal 1510 comprises an annular member that may be fabricated from silicon or other materials such as, for example, Ultem® and is over molded or otherwise sealingly attached to the waveguide 1412 at a node "N". The seal 1510 may have an inner rim portion 1512 that is molded onto the waveguide 1412 at a node "N" and two axial seal portions 1514, 1516 that extend axially in opposite directions beyond the inner portion 1512 and which are separated by a groove 1518. The axial portions 1514, 1516 are sized to extend into a groove 1520 provided in the outer sheath 1420. As can be seen in FIG. 82, the groove 1520 has an inwardly protruding ring 1522 sized to extend into the groove 1518 in the seal 1510. In the illustrated embodiment, the ring 1522 has an angled ramp 1524 formed thereon that permits the seal 1510 to slide over it during assembly, then lock in place. The outer sheath 1420 may be fabricated from, for example, Ultem®.

Figure 83:
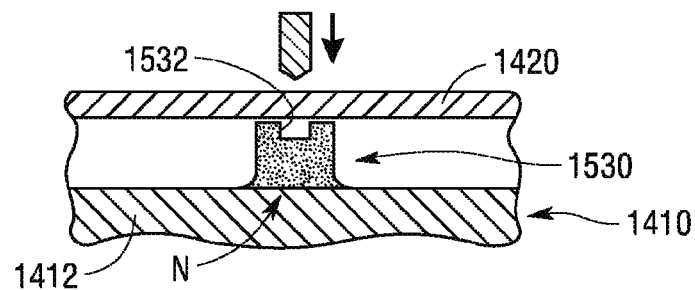
FIG. 83 is a partial cross-sectional view of another non-limiting seal embodiment between a hollow sheath and a waveguide portion of an ultrasonic implement embodiment, prior to being crimped in position.
Figure 84:
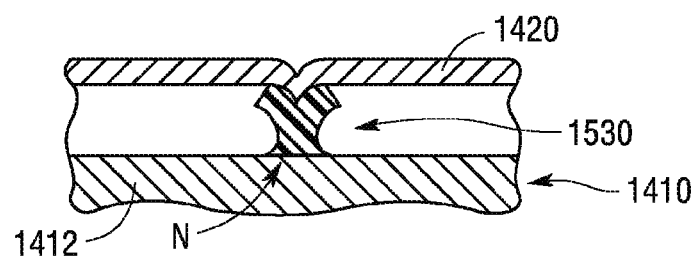
FIG. 84 is a partial cross-sectional view of the seal embodiment of FIG. 83 after being crimped in position.

FIGS. 83 and 84 depict a non-limiting embodiment of a seal 1530 that may be employed between in the waveguide or proximal portion 1412 of the ultrasonic implement 1410 and the outer sheath 1420. The seal 1530 comprises an annular member that may be fabricated from silicon or other materials such as, for example, Ultem® and is over molded or otherwise sealingly attached to the waveguide 1412 at a node "N".

The seal 1530 may have a groove 1532 therein as shown in FIG. 83. The outer sheath 1420 is then crimped to thereby crush the seal 1530 as shown in FIG. 84. The outer sheath 1420 could be crimped evenly all the way around the circumference, or it could be crimped in discrete locations. For example, four evenly spaced (e.g., at 90 degree intervals) crimps may be employed. In such embodiments, the outer sheath 1420 may be fabricated from, for example, stainless steel.

Figure 85:
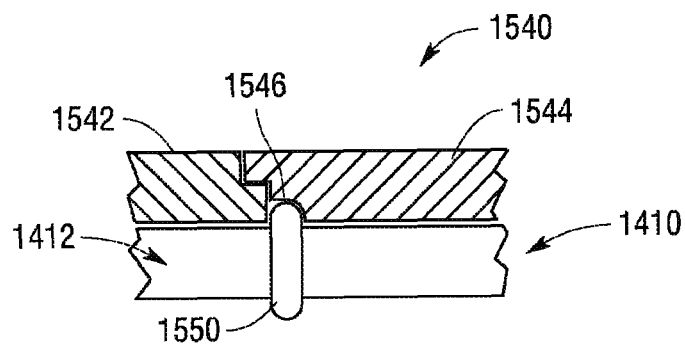
FIG. 85 is a partial cross-sectional view of another non-limiting seal embodiment between a two-piece hollow sheath and a waveguide portion of an ultrasonic implement embodiment.

FIG. 85 depicts a portion of an outer sheath 1540 that has a proximal axial portion 1542 and a distal axial section 1544 that are adapted to be interconnected together by, for example, welding, press fit, threading or snapping together. As can be seen in FIG. 85, the distal axial section 1544 has a groove portion 1546 sized to engage a portion of an annular seal 1550 that is over molded or otherwise sealingly installed on the waveguide or proximal portion 1412 of the ultrasonic implement 1410 at a node "N". Thus, when attached together, the proximal axial section 1542 and distal axial section 1544 serve to trap and compress a portion of the seal 1550 therebetween. In alternative embodiments, the groove portion 1546 may be provided in the proximal axial section 1542 or each section 1542, 1544 may have a groove segment therein that cooperate to accommodate the annular seal 1550 therein.

Figure 86:
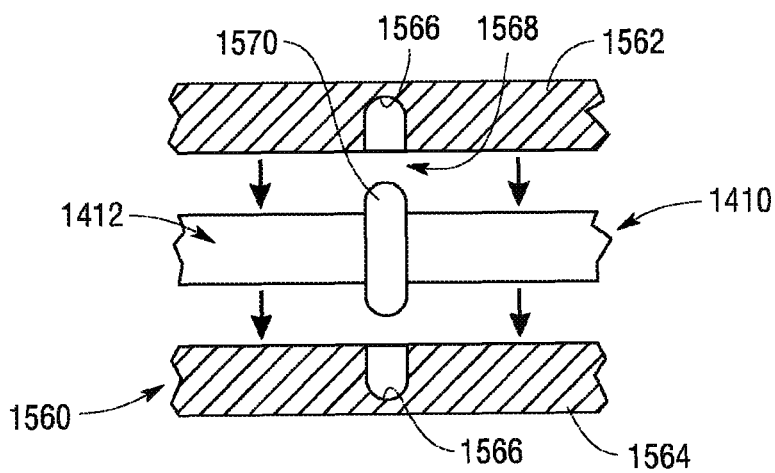
FIG. 86 is a partial cross-sectional exploded assembly view of another non-limiting seal embodiment between another two-piece hollow sheath and a waveguide portion of an ultrasonic implement embodiment.
Figure 87:
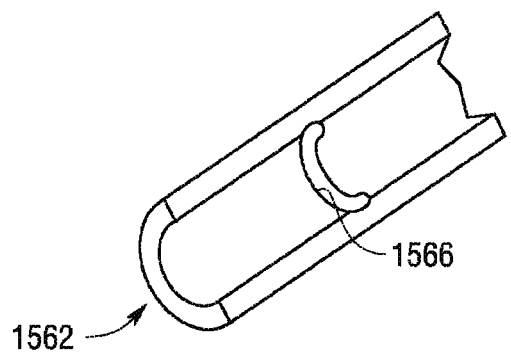
FIG. 87 is a partial perspective view of a portion of the two piece hollow sheath embodiment of FIG. 86.

FIG. 86 depicts a portion of an outer sheath, generally designated as 1560 that consists of two lateral halves 1562, 1564. Each lateral half 1562, 1564 has a semi-annular groove segment 1566 formed therein. See FIG. 87. The semi-annular groove segments 1566 form an annular groove 1568 sized to receive an annular seal 1570 that is over molded onto or otherwise attached to the waveguide or proximal portion 1412 when the lateral halves 1562, 1564 are joined together to form the hollow outer sheath 1560. By creating a two piece outer sheath 1560, the seal 1570 could have much greater interference with the outer sheath 1560, than it generally could have if the waveguide 1412 must be pushed down the outer sheath 1560 during the assembly process. The two outer sheath halves 1562, 1564 may be joined together by welding, snap fitting or other suitable methods. Thus, the seal 1570 may first be installed on the waveguide 1412. Thereafter, the two halves 1562, 1564 may be brought together around the wave guide 1412 such that the seal 1570 is trapped within the groove 1568. The halves 1562, 1564 are then fastened together in that position.

Figure 88:
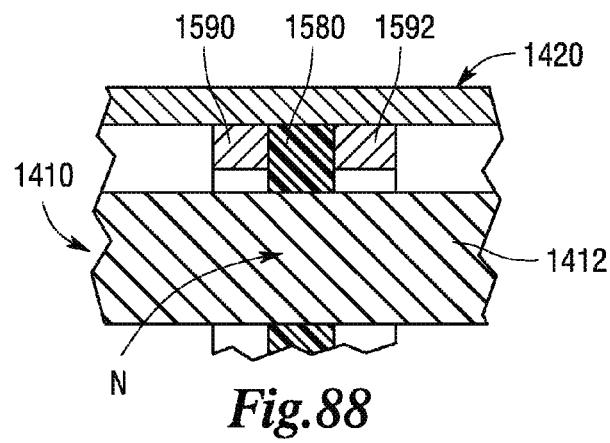
FIG. 88 is a partial cross-sectional view of another non-limiting seal embodiment between a hollow sheath and a waveguide portion of an ultrasonic implement embodiment.

FIG. 88 depicts a non-limiting embodiment of a seal 1580 that may be employed between in the waveguide portion 1412 of the ultrasonic implement and the outer sheath 1420. The seal 1580 comprises an annular member that may be fabricated from silicon or other materials such as, for example, Ultem® and is over molded or otherwise sealingly attached to the waveguide or proximal portion 1412 at a node "N". The seal 1580 may be held in place by a proximal ring 1590 and a distal ring 1592. The proximal ring 1590 may comprise an integral portion of the outer sheath 1420 or it could comprise a separate component that is pressed into the outer sheath 1420 or otherwise attached thereto. The distal ring 1592 may be glued, press fit or otherwise attached to the outer sheath 1420. The distal ring 1592, upon installation, may provide compression on the seal 1580. This would increase the force between the seal 1580 and the waveguide 1412, further decreasing fluid movement past the seal 1580. The rings 1590, 1592 may comprise split annular rings or rings with no splits therein. In addition, as can be seen in FIG. 88 the tings 1590, 1592 may be sized relative to the waveguide 1412 such that an amount of clearance "C" is provided therebetween.

Figure 89:
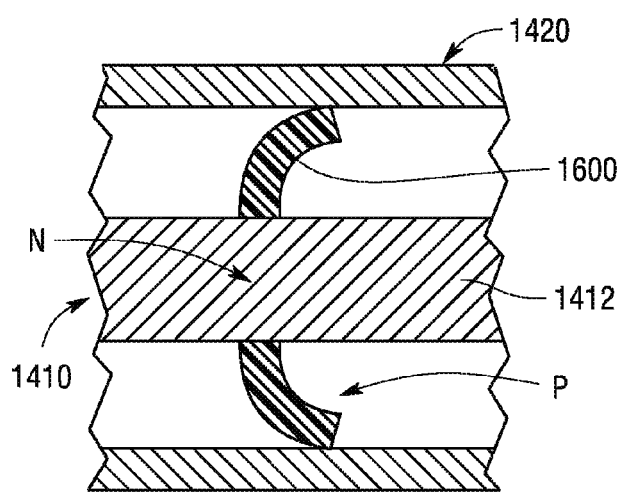
FIG. 89 is a partial cross-sectional view of another non-limiting seal embodiment between a hollow sheath and a waveguide portion of an ultrasonic implement embodiment.

FIG. 89 depicts a non-limiting embodiment of a seal 1600 that may be employed between in the waveguide or proximal portion 1412 of an ultrasonic implement 1410 and the outer sheath 1420. The seal 1600 comprises an annular member that may be fabricated from silicon or other materials such as, for example, Ultem® and is over molded or otherwise sealingly attached to the waveguide 1412 at a node "N". The seal 1600 may have an outer diameter that is greater than the inner diameter of the outer sheath 1420. The seal 1600 may further have a proximal side 1602 and a distal side 1604. When assembled, an outer portion of the proximal side 1602 of the seal 1600 sealingly contacts the inner wall 1421 of the outer sheath 1420. Thus, when fluid pressure "P" builds up on the distal side of the seal 1600, the seal 1600 is further urged into sealing contact with the outer sheath 1420, thereby creating a better seal between the waveguide 1412 and the outer sheath 1420.

Figure 90:
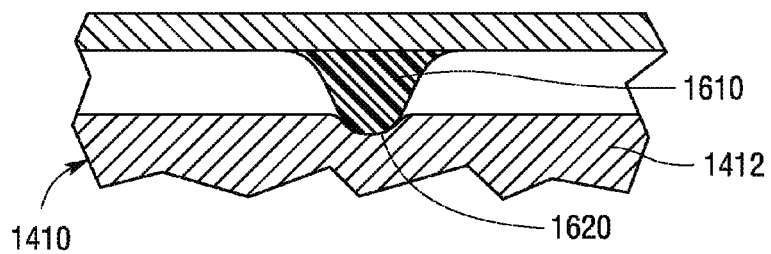
FIG. 90 is a partial cross-sectional view of another non-limiting seal embodiment between a hollow sheath and a waveguide portion of an ultrasonic implement embodiment.
Figure 91A:
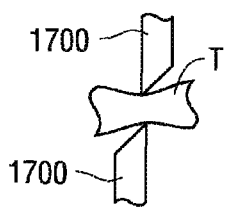
FIG. 91A is an illustration depicting an initial position of two cutting edge embodiments preparing to cut tough tissue.
Figure 91B:
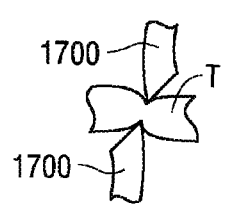
FIG. 91B is a second position of the cutting edges and tissue of FIG. 91A.
Figure 91C:
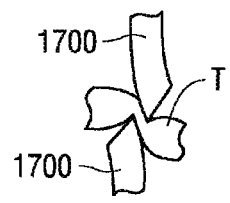
FIG. 91C is a third position of the cutting edges and tissue of FIGS. 91A-B.
Figure 91D:
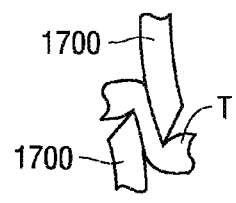
FIG. 91D is a fourth position of the cutting edges and tissue of FIGS. 91A-C.

FIG. 90 depicts a non-limiting embodiment of a seal 1610 that may be employed between in the waveguide or proximal portion 1412 of the blade and the outer sheath 1420. The seal 1610 comprises an annular member that may be fabricated from silicon or other materials such as, for example, Ultem® and is molded or otherwise attached to the outer sheath 1420 as shown. In this embodiment, an annular groove 1620 may be provided in the waveguide 1412 for receiving a portion of the seal 1610 therein. In alternative embodiments, no groove is provided. It will be further understood that the seals depicted in FIGS. 79-82 may likewise be attached to the outer sheath instead of the waveguide or proximal portion of the cutting blade or implement as illustrated without departing from the spirit and scope of the various non-limiting embodiments disclosed herein and their respective equivalents. In addition, it will be further understood that the various seal embodiments described herein may be effectively employed with any of the surgical instrument embodiments described above. That is, the various non-limiting seal arrangements disclosed herein and their respective equivalent structures may be effectively employed to achieve a seal between the ultrasonic blade or waveguide and the corresponding inner sheath. In those embodiments that employ an inner sheath and an outer sheath, but do not apply a suction therebetween, the various non-limiting seal arrangements disclosed herein and their respective equivalents may also be effectively employed to achieve a substantially fluid-tight seal between the inner and outer sheaths. In yet other non-limiting embodiments, the seal may be employed between an ultrasonic blade and an outer sheath wherein the ultrasonic blade does not engage in gross-rotational motion relative to the outer sheath. In such embodiments, the seal may be rigidly attached to the ultrasonic blade and the outer sheath. In still other non-limiting embodiments, the ultrasonic blade may oscillate within the outer sheath. For example the ultrasonic blade may oscillate through a 90 degree arc (45 degrees on each side of a central axis). In such embodiments, the seal may be rigidly attached to the outer sheath and ultrasonic blade by, for example, adhesive, crimping, etc. The seal material may comprise an elastic rubber material or the like that would accommodate twisting of the seal for a range of ±45 degrees. In such embodiments, the stretch experienced by the seal may help to return the blade to a neutral position of zero degrees (in alignment with the central axis).

Various of the above-described embodiments employ rotating blades that serve to shear off tissue between cutting edges formed on the blade and edges of the surrounding outer sheath. While such arrangements are very effective in cutting most tissues, tough tissue, such as tendon tissue for example, can be difficult to effectively cut because it can tend to "milk" between the blade and the outer sheath. Such problem is akin to problems encountered when scissors are used to cut through a tough material such as leather, for example. In short, the scissor blades separate and the material does not get cut. This phenomenon is graphically depicted in FIGS. 91A-D. As can be seen in those Figures, two cutting blades 1700 are employed to cut through tough tissue "T". As the blades 1700 move inward toward the tissue "T", the tissue "T" moves between the blades 1700 and causes them to separate.

Figure 92:
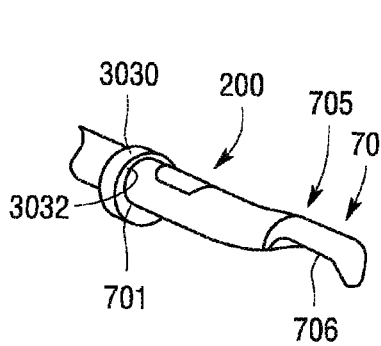
FIG. 92 is a perspective view of a portion of a non-limiting cutting blade and bushing embodiment.

In various blade and sheath embodiments disclosed herein, it may be advantageous to minimize the amount of clearance between the cutting portion of the outer sheath and the cutting edge(s) of the blades. For example, it may be desirable to maintain the amount of clearance between the cutting portion of the outer sheath and the cutting edge(s) on the blades within the range of 0.001" to 0.005". In other non-limiting embodiments, one cutting edge or portion is harder than the other cutting portion. For example, the cutting edge(s) on the blades may be harder than the cutting portion of the outer sheath or visa versa. The motor may then be activated with or without ultrasound to achieve a near zero clearance between the cutting edges/portion. In addition to such approaches or in place of such approaches, other embodiments may employ structure to bias at least a distal portion the blade in an "off-center" arrangement within the outer sheath while still facilitating the rotation of the blade therein. More particularly and with reference to FIGS. 92-93, there is shown a blade 200 of the type and construction described above, extending through an outer sheath assembly 3000. In the depicted embodiment, the outer sheath assembly 3000 is used in connection with a surgical instrument 3001 that may be constructed in any of the manners described above to selectively apply gross rotational motion to the blade 200 as well as to selectively apply ultrasonic motion thereto.

Figure 93:
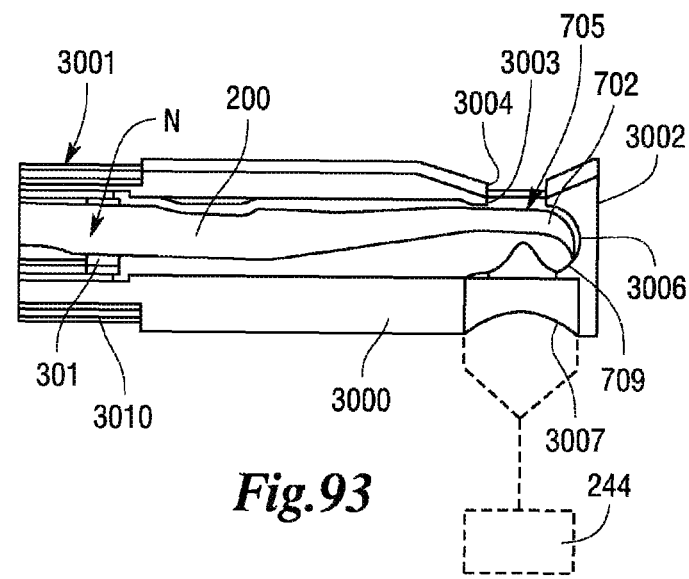
FIG. 93 is a cross-sectional view of a portion of the blade and bushing embodiment of FIG. 92 in a non-limiting surgical instrument embodiment.

In the embodiment depicted in FIG. 93, the blade 200 extends axially through an inner sheath 3020 that is mounted within a portion of the instrument housing 3010. The outer sheath assembly 3000 is attached to the instrument housing 3010 and has a distal tip portion 3002 that has a window or opening 3004 therein. As discussed above, the window 3004 enables tissue to be drawn into a tip cavity 3006 formed within the distal tip portion 3002. Suction may be applied to the tip cavity 3006 through a suction port 3007 in the distal tip portion 3002 of the outer sheath assembly 3000 that communicates with a source of suction 244. In these embodiments, the blade 200 is somewhat flexible and may be fabricated from, for example, Titanium. In addition, the waveguide portion or proximal portion of blade 200 extends through a bushing 3030 that is mounted within the inner sheath 3020 in the location of node "N". In various embodiments, the inner sheath 3020 may be fabricated from material that is substantially rigid and resists bending. For example, the inner sheath 3020 may be fabricated from Ultem or similar materials. The bushing 3030 may be fabricated from, for example Ultem® and be non-rotatably retained within the inner sheath 3020 by, for example, stainless steel.

Figure 92A:
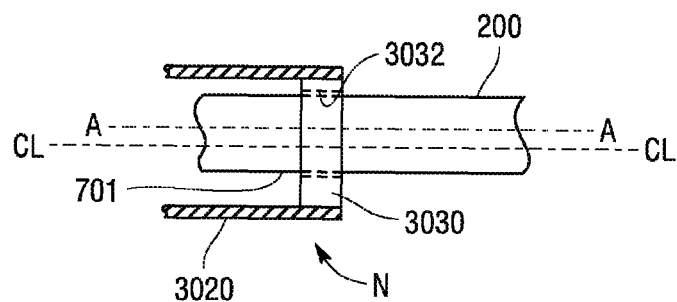
FIG. 92A is a partial cross-sectional view of a portion of the blade and bushing embodiment of FIG. 92 installed within an inner sheath of a non-limiting surgical instrument embodiment.

As can be seen in FIGS. 92A and 93, the waveguide or proximal portion 701 of blade 200 extends through a hole 3032 in the bushing 3030. The centerline CL-CL of the bushing hole 3032 is offset (i.e., not coaxial with) from the central axis A-A defined by the outer sheath 3000. The bushing hole 3032 is sized relative to the proximal portion 701 of the blade 200 to permit the proximal portion 701 to rotate freely therein, yet also serves to bias the distal end portion 700 of the blade 200 off the center axis A-A of the outer sheath 3000 such that the tissue cutting distal end 705 of the blade 200 is retained in rotatable contact with the cutting edge 3005 defined by the window opening 3004. In some embodiments, for example, the blade 200 may be biased off center a distance that can be as much as 0.030". Because the tissue cutting distal end 705 of the blade 200 is biased in such a manner, the distal end 705 resists forces encountered when cutting tough tissue which may otherwise cause cutting edges 706 on the distal end 705 to move away from the cutting edge 3005 of the window opening 3004.

Figure 94:
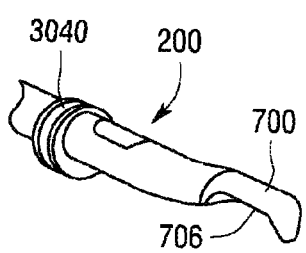
FIG. 94 is a perspective view of a portion of another non-limiting cutting blade and bushing embodiment.
Figure 95:
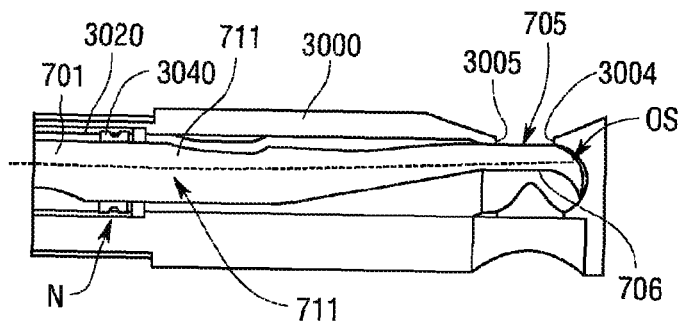
FIG. 95 is a cross-sectional view of a portion of the blade and bushing embodiment of FIG. 94 in a non-limiting surgical instrument embodiment.

FIGS. 94 and 95 illustrate another embodiment wherein a proximal portion 701 of the blade 200 coaxially extends through a bushing 3040 that may be fabricated from, for example, silastic silicone or Ultem® and be retained within the inner sheath 3020 by, for example, a slip fit. As with the above embodiment, the bushing 3040 may be located at the node "N" along the waveguide or proximal portion of the blade 200. However, in this embodiment, the distal portion 711 (i.e., the portion of the blade 200 that extends distally from the bushing 3040) is bent slightly to bias the tissue cutting distal end 705 of the blade 200 into the cutting edge 3005 of the window opening 3004. For example, the distal portion 711 of the blade 200 may be bent approximately 0.030 inches off-center (distance OS in FIG. 95). Such arrangement causes the tissue cutting distal end 705 of the blade 200 to resist forces when cutting tough tissue which may otherwise cause cutting edges 706 on the blade 200 to move away from the cutting edge 3005 of the window opening 3004.

Figure 96:
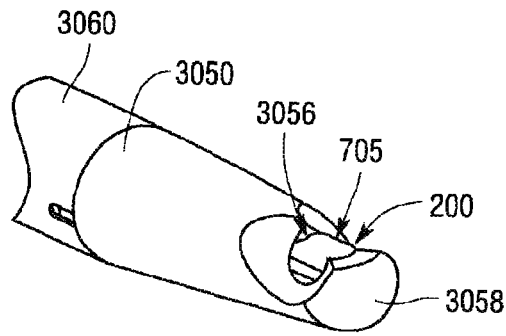
FIG. 96 is a partial perspective view of a portion of a non-limiting blade and outer sheath embodiment.
Figure 97:
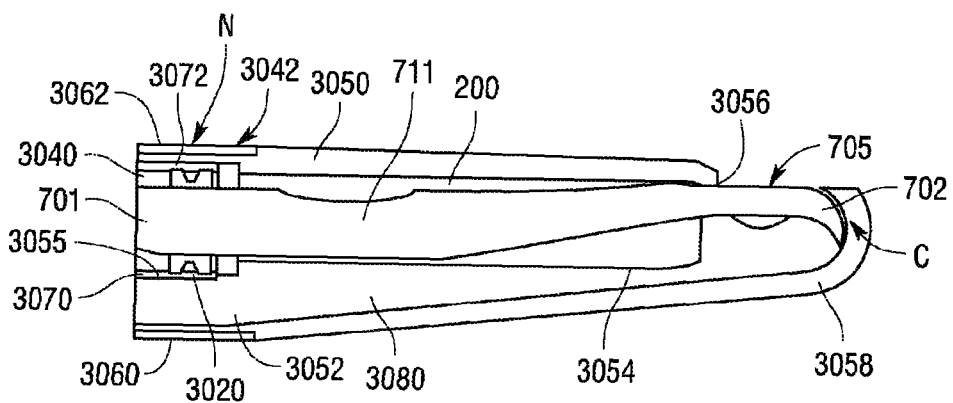
FIG. 97 is a cross-sectional view of the blade and outer sheath arrangement of FIG. 96.

FIGS. 96-97 depict another non-limiting outer sheath 3040 and blade 200 embodiment. In this embodiment, a distal outer sheath tip 3050 is employed. The distal outer sheath tip 3050 may be fabricated from metal such as, for example, stainless steel and have a proximal bearing portion 3052 that extends into an open distal end 3062 of the outer sheath 3060. The outer sheath 3060 may be fabricated from, for example, stainless steel and may be attached to the distal outer sheath tip 3050 by fasteners, adhesive, etc. The proximal end 3062 of the outer sheath 3060 is attached to a portion of an instrument housing as was described above. The instrument may comprise many of the various instrument embodiments described in detail above that supplies gross rotational motion to the blade 200 as well as ultrasonic motions thereto.

The waveguide or proximal portion 701 of the blade 200 may be attached to an ultrasonic horn (not shown) and extend through an inner sheath 3070 in the various manners described above. The proximal portion 701 of the blade 200 may be rotatably supported within the inner sheath 3070 by a bushing 3040 as was described above. A distal portion 711 of the blade 200 rotatably extends through a lumen 3054 in the distal outer sheath tip 3050. See FIG. 97. A window 3056 is formed in the distal outer sheath tip 3050 to expose the tissue cutting distal end 705 of the blade 200. As with various embodiments described above, the window 3056 may define at least one cutting edge 3057 that interacts with the rotating tissue cutting distal end 705 of blade 200 to cut tissue drawn into the window 3056. In this embodiment, the outer diameter "OD" of the tissue cutting distal end portion 705 of the blade 200 at the point wherein the distal end 705 of the blade 200 protrudes distally into the window opening 3056 is greater than the inner diameter "ID" of the lumen 3054. In some embodiments, for example, the inner lumen diameter "ID" may be approximately 0.140" and the blade "OD" may be approximately 0.150". Such arrangement results in an interference between the tissue cutting distal end 705 of the blade 200 and the distal outer sheath tip 3050. In such arrangement, the distal portion 711 of the blade 200 essentially comprises a cantilevered beam which results in the tissue cutting distal end 705 of the blade 200 being pushed downward (FIG. 97) by the distal outer sheath tip 3050.

In the embodiments depicted in FIGS. 92-97, it may be desirable to provide an amount of clearance between the distal end 3058 of the distal outer sheath tip 3050 and the curved tip portion 702 of the blade 200. This clearance "C" is illustrated in FIG. 97. Such clearance allows unimpeded ultrasonic motion of the blade 200. However, it may be desirable to minimize such clearance "C" to reduce suction loses around the curved tip portion 702 which may hamper the device's ability to cut tissue.

Figure 98:
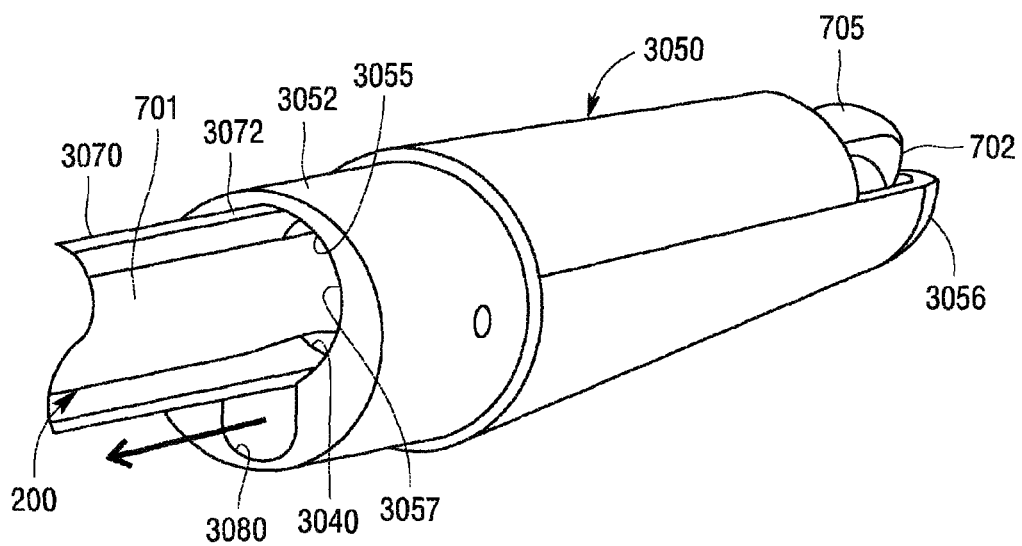
FIG. 98 is a partial rear perspective view of a portion of the outer sheath and blade arrangement of FIG. 97.
Figure 99:
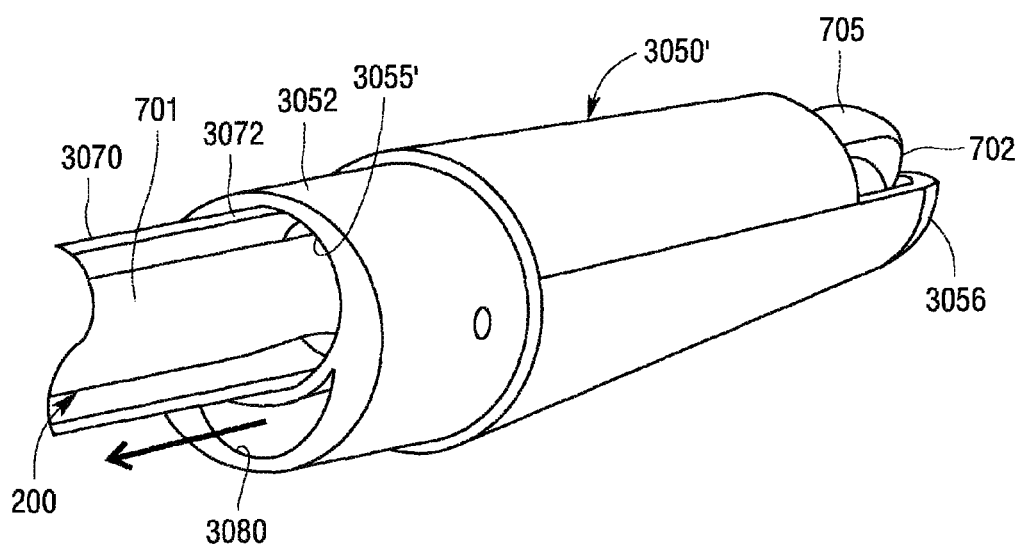
FIG. 99 is a partial rear perspective view of a portion of another non-limiting outer sheath and blade embodiment.

Also, to facilitate the drawing of tissue into the window opening 3056, suction must be applied within the distal outer sheath tip 3050 from a source of suction (not shown) in the various mariners described above. In this embodiment, for example, a suction path 3080 is provided in the distal outer sheath tip 3050 as shown in FIGS. 97 and 98. A seal 3090 is journaled on the distal portion 711 of the blade 200 to establish a fluid tight seal at a point wherein the distal portion 711 of the blade 200 exits the inner sheath 3070. See FIG. 97. Also in this embodiment, the distal end 3072 of the inner sheath 2070 extends into an opening 3055 in the bearing portion 3052 of the distal outer sheath tip 3050 to provide relative rigid support thereto. As can be seen in FIG. 98, the suction path 3080 forms a discontinuity in the inner sheath support surface 3057 defined by opening 3055. FIG. 99 depicts an alternative distal outer sheath tip 3050' wherein the suction path 3080' does not extend into the opening 3055' that supports the distal end 3072 of the inner sheath 3070.

Various ultrasonic surgical instruments that employ an outer sheath and rotatable cutting member arrangement also face the challenge of outer sheath and blade deformation due to heat and high contact forces between those two components. Deformation of the distal tip portion of the outer sheath can be reduced by changing the tip material to metal, but this can result in the undesirable effect of damaging the blade via galling, which can ultimately result in broken blades and extremely limited blade life. Such sheath tip blade galling damage can occur due to metal-to-metal contact between the blade and the sheath tip. This condition may be exacerbated when cutting tough tissues such as tendon and the like. As was discussed above, such tough tissues may bias the cutting edges away from each other and force the opposite cutting edge or face of the blade into contact with the sheath tip, thereby resulting in galling.

Figure 100:
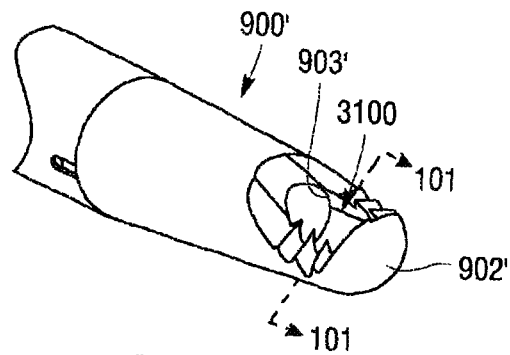
FIG. 100 is a partial perspective view of another non-limiting outer sheath embodiment.
Figure 101:
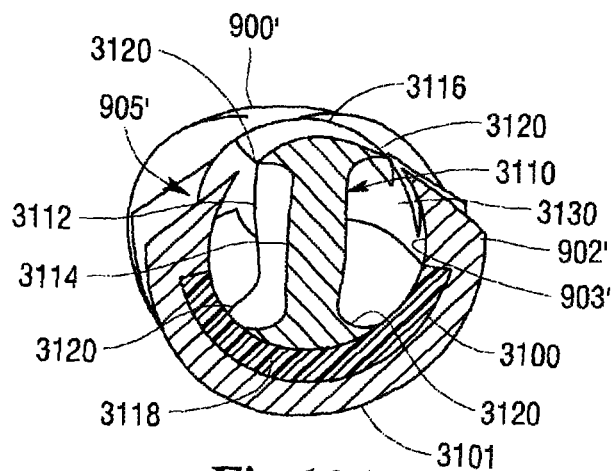
FIG. 101 is a cross-sectional end view of the outer sheath embodiment of FIG. 100 supporting a cutting blade embodiment therein.

Various non-limiting embodiments described herein and their respective equivalents may employ a thin friction-reducing material on the inner wall of the tip cavity formed within the distal tip portion of the outer sheath or, in alternative embodiments, a low friction or friction reducing pad may be affixed within the tip cavity to protect the blade. One exemplary embodiment is depicted in FIGS. 100 and 101. As can be seen in those Figures, the outer sheath 900' that was described above has a friction-reducing polymeric coating or pad 3100 therein. In various embodiments, the distal tip portion 902' of the sheath 900' may be fabricated from metal such as stainless steel and the friction reducing material or pad 3100 may be fabricated from, for example, polyimide, carbon-filled polyimide, Teflon®, Teflon-Ceramic, etc. In those embodiments in which a pad is employed, the pad may be affixed within the tip portion 902' by, for example, adhesive or a dovetail joint arrangement. The pad 3100 is preferably configured to match the corresponding geometry of the blade. For example, as shown in FIG. 101, a blade 3110 that may be substantially similar to blade 200 described above, has a distal end portion 3112 that has a central portion 3114 that separates two cutting faces 3116, 3118. The cutting faces 3116, 3118 have an arcuate shape and have cutting edges 3120 formed on each edge thereof. In that embodiment, the polymeric pad 3100 also has a similar arcuately shaped upper surface 3101. The advantage of this concept is that it maintains a hard metallic cutting edge (e.g., stainless steel), which is advantageous for cutting tough tissue. It also protects the broad cutting faces 3116, 3118 of the blade 200 when the pad 3100 is fabricated from softer materials that can otherwise support the forces applied to the blade. In addition or in the alternative, the inner wall 903' of the tip portion 902' may be coated with a friction-reducing coating 3130 of the type described above. The coating 3130 may comprise a separate component that is held in place via adhesive or it may comprise a deposition coating that is directly adhered to the inner surface 903' of the tip portion 902'. For example, a Teflon® material may be applied to portions of the inner wall 903' through vapor deposition. The portions of the tip 902' wherein the coating is not needed may be masked off using known masking techniques before exposing the tip 902' to the vapor deposition process.

Figure 102:
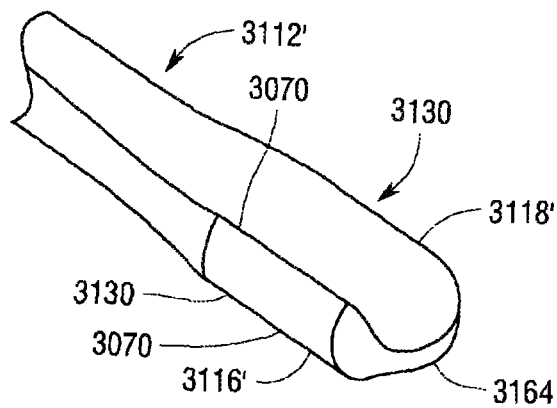
FIG. 102 is a perspective view of a portion of another non-limiting blade embodiment.

FIG. 102 depicts a tissue cutting blade end 3112' that may be coated with a relatively hard, low-friction material to increase surface hardness and reduce friction. In particular, as can be seen in that Figure, at least portions of the cutting faces 3116', 3118' are coated with the coating material 3130. In some embodiments, for example, the coating material may comprise coating materials such as Titanium Nitride, Diamond-Like coating, Chromium Nitride, Graphit iC™, etc. The blade 3060' may be employed in connection with an outer sheath tip that is fabricated from metal (e.g., stainless steel) in order to avoid blade galling and eventual blade breakage. In alternative embodiments, the entire distal tissue cutting end of the blade may be coated with the coating material 3130.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Sterilization can also be done by any number of ways known to those skilled in the art including beta or gamma radiation, ethylene oxide, and/or steam.

In various embodiments, an ultrasonic surgical instrument can be supplied to a surgeon with a waveguide and/or end effector already operably coupled with a transducer of the surgical instrument. In at least one such embodiment, the surgeon, or other clinician, can remove the ultrasonic surgical instrument from a sterilized package, plug the ultrasonic instrument into a generator, as outlined above, and use the ultrasonic instrument during a surgical procedure. Such a system can obviate the need for a surgeon, or other clinician, to assemble a waveguide and/or end effector to the ultrasonic surgical instrument. After the ultrasonic surgical instrument has been used, the surgeon, or other clinician, can place the ultrasonic instrument into a sealable package, wherein the package can be transported to a sterilization facility. At the sterilization facility, the ultrasonic instrument can be disinfected, wherein any expended parts can be discarded and replaced while any reusable parts can be sterilized and used once again. Thereafter, the ultrasonic instrument can be reassembled, tested, placed into a sterile package, and/or sterilized after being placed into a package. Once sterilized, the reprocessed ultrasonic surgical instrument can be used once again.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

All of the above U.S. patents and U.S. patent applications, and published U.S. patent applications referred to in this specification are incorporated herein by reference in their entirety, but only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ultrasonic surgical instrument, comprising:
 a housing;
 an ultrasonic transducer assembly supported within said housing;
 a blade coupled to said ultrasonic transducer assembly;
 a hollow sheath coupled to said housing and extending axially around a portion of said blade; and
 a seal assembly for establishing a seal between a portion of said blade and said hollow sheath, said seal assembly comprising:
  a first annular seal portion attached to said blade; and
  two axial seal portions extending axially beyond said first annular seal portion in opposite axial directions from said first annular seal portion and in flexible sealing contact with corresponding portions of an inner wall of said hollow sheath.

2. The ultrasonic surgical instrument of claim 1 further comprising an annular groove between said two axial seal portions.

3. The ultrasonic surgical instrument of claim 2 wherein a portion of said hollow sheath extends into said annular groove.

4. The ultrasonic surgical instrument of claim 2 wherein said two axial seal portions extend into a corresponding annular sheath groove formed in said hollow sheath.

5. The ultrasonic surgical instrument of claim 4 further comprising an inwardly protruding ring portion in said sheath groove, said inwardly protruding ring portion having an angled side portion formed thereon for sliding engagement with at least one of said axial seal portions during installation of said blade into said hollow sheath.

6. The ultrasonic surgical instrument of claim 1 wherein said first annular seal portion is attached to said blade at a node in said blade.

7. An ultrasonic surgical instrument, comprising:
   an ultrasonic transducer assembly;
   a blade coupled to said ultrasonic transducer assembly;
   a hollow sheath extending axially around a portion of said blade; and
   a seal assembly for establishing a seal between a portion of said blade and said hollow sheath, said seal assembly comprising:
      a first annular seal portion attached to said blade; and
      two axial seal portions extending axially beyond said first annular seal portion in opposite axial directions from said first annular seal portion and in flexible sealing contact with corresponding portions of an inner wall of said hollow sheath.

8. An ultrasonic surgical instrument, comprising:
   an ultrasonic transducer assembly;
   a blade coupled to said ultrasonic transducer assembly;
   a tubular member extending axially around a portion of said blade; and
   a seal assembly for establishing a seal between a portion of said blade and said tubular member, said seal assembly comprising:
      a first annular seal portion attached to said blade; and
      two axial seal portions extending axially beyond said first annular seal portion in opposite axial directions from said first annular seal portion and in flexible sealing contact with an inner wall of said tubular member.

* * * * *